US007049136B2

(12) United States Patent
Seed et al.

(10) Patent No.: US 7,049,136 B2
(45) Date of Patent: May 23, 2006

(54) REDIRECTION OF CELLULAR IMMUNITY BY RECEPTOR CHIMERAS

(75) Inventors: Brian Seed, Boston, MA (US); Charles Romeo, Belmont, MA (US); Waldemar Kolanus, Watertown, MA (US)

(73) Assignee: The General Hospital Corporation, Boston, MA (US)

( * ) Notice: Subject to any disclaimer, the term of this patent is extended or adjusted under 35 U.S.C. 154(b) by 810 days.

(21) Appl. No.: 09/243,008

(22) Filed: Feb. 2, 1999

(65) Prior Publication Data
US 2004/0005334 A1   Jan. 8, 2004

Related U.S. Application Data

(63) Continuation of application No. 08/394,176, filed on Feb. 24, 1995, now abandoned.

(51) Int. Cl.
  *C12N 5/02* (2006.01)
(52) U.S. Cl. ..................................... 435/325
(58) Field of Classification Search .............. 435/346, 435/325; 530/350; 424/195.11
  See application file for complete search history.

(56) References Cited

U.S. PATENT DOCUMENTS

| 4,690,915 A | 9/1987 | Rosenberg ..................... 514/2 |
| 4,946,778 A | 8/1990 | Ladner et al. |
| 5,091,513 A | 2/1992 | Huston et al. |
| 5,225,538 A | 7/1993 | Capon et al. |
| 5,336,603 A | 8/1994 | Capon et al. |
| 5,359,046 A * | 10/1994 | Capon et al. .............. 536/23.4 |
| 5,439,819 A | 8/1995 | Littman et al. |
| 5,504,000 A | 4/1996 | Littman et al. |
| 5,686,281 A | 11/1997 | Roberts .................... 435/172.3 |
| 5,712,149 A | 1/1998 | Roberts .................... 435/252.3 |

FOREIGN PATENT DOCUMENTS

| EP | 0 180 878 | 5/1986 |
| EP | 0 314 317 | 5/1989 |
| EP | 0 325 262 | 7/1989 |
| EP | 0 340 793 | 11/1989 |
| EP | 0 394 827 | 10/1990 |
| JP | 10-63394 | 3/1989 |
| NZ | 224379 | 12/1990 |
| WO | WO 86/01533 | 3/1986 |
| WO | WO88/01649 | 3/1988 |
| WO | WO 90/04640 | 5/1990 |
| WO | WO 90/11360 | 10/1990 |
| WO | WO 91/10736 | 7/1991 |
| WO | WO 92/10591 | 6/1992 |
| WO | WO 92/15322 | 9/1992 |
| WO | WO 93/19163 | 9/1993 |
| WO | WO 95/02686 | 1/1995 |
| WO | WO 95/21528 | 8/1995 |
| WO | WO 96/26265 | 8/1996 |

OTHER PUBLICATIONS

Johnston et al., Science, 260: 1286-1293, May 1993.*
Haynes, Science, 260: 1279-1285, May 1993.*
Harding et al., J. Exp. Med., 177: 1791-1796, Jun. 1993.*
Scwartz, Cell, 71: 1065-1068, Dec. 1992.*
Stancovski et al., "Targeting of T Lymphocytes to Neu/HER2—Expressing Cells Using Chimeric Single Chain Fv Receptors" *The Journal of Immunology* 151:6577-6582 (1993).
Bernard et al., "High-affinity interleukin 2 binding by an oncogenic hybrid interleukin 2-epidermal growth factor receptor molecule," Proc. Natl. Acad. Sci. USA 84:2125-2129 (1987).
Yarden et al., "Growth Factor Receptor Tyrosine Kinases," Ann. Rev. Biochem. 57:443-478 (1988).
Alexander et al., "Kinases and phosphatases in T-cell activation," Immunology Today 10:200-205 (1989).
Ashwell et al., "Genetic and Mutational Analysis of the T-Cell Antigen Receptor," Ann. Rev. Immunol. 8:139-167 (1990).
Verhoeyen et al., "Reshaping Human Antibodies: Grafting an Antilysozyme Activity," Science 259:1534-1536 (1988).
Marshall, Science 269:1050-1055 (1995).
Brown, Washington Post, A1 and A22 (Dec. 8, 1995).
Jones et al., Nature 323:346-349 (Sep. 25, 1986).
Suda et al., Blood 79(9):2288-2295 (May 1, 1992).
He et al., Blood 79(9):2296-2302 (May 1, 1992).
Nakumara et al., Exp. Hematology 21:236-242 (1993).
Alberola-Ila et al., J. Immunology 151(9):4423-4430 (Nov. 1, 1993).
Maggio et al., Proc. Natl. Acad. Sci. 90:3103-3107 (Apr. 1993).
Taniguchi et al., Journal of Biological Chem. 266:15790-15796 (1991).
Bachmann et al., Current Biology 6:320-326 (1994).
Coghlan et al., New Scientist 14-15 (Nov. 25, 1995).
Abraham and Veillette, Mol. Cell Biol. 10:5197-5206 (1990).
Appleby et al., Cell 70:751-763 (1992).
Balk and Terhorst, Immunol. Ser. 45:411-416 (1989).
Bell et al., Mol. Cell Biol. 12:5549-5554 (1992).
Bolen et al., Adv. Cancer Res. 57:103-149 (1991).
Burkhardt et al., Proc. Natl. Acad. Sci. USA 88:7410-7414 (1991).
Campbell and Sefton, Mol. Cell Bio. 12:2315-2321 (1992).
Campbell and Sefton, EMBO J. 9:2125-2131 (1990).

(Continued)

Primary Examiner—Patrick J. Nolan
(74) *Attorney, Agent, or Firm*—Clark & Elbing LLP

(57) ABSTRACT

Disclosed is a method of directing a cellular response in a mammal by expressing in a cell of the mammal a chimeric receptor which causes the cells to specifically recognize and destroy an infective agent, a cell infected with an infective agent, a tumor or cancerous cell, or an autoimmune-generated cell. Also disclosed are cells which express the chimeric receptors and DNA encoding the chimeric receptors.

13 Claims, 21 Drawing Sheets

OTHER PUBLICATIONS

Carter et al., Proc. Natl. Acad. Sci. USA 88:2745-2749 (1991).
Chan et al., Proc. Natl. Acad. Sci. USA 88:9166-9170 (1991).
Clark and Ledbetter, Adv. Cancer Res. 52:81-149 (1989).
Clark et al., Science 258:123-126 (1992).
Cooke et al., Cell 65:281-291 (1991).
Cooke and Perlmutter, New Biol. 1:66-74 (1989).
Davidson et al., J. Exp. Med. 175:1483-1492 (1992).
DeFranco, Eur. J. Biochem. 210:381-388 (1992).
Eiseman and Bolen, Nature 355:78-80 (1992).
Gassman et al., Eur. J. Immunol. 22:283-286 (1992).
Glaichenhaus et al., Cell 64:511-520 (1991).
Gold et al., Nature 345:810-813 (1990).
Goldsmith and Weiss 84:6879-6883 (1987).
Grant et al., Science 258:1903-1910 (1992).
Hatakeyama et al., Science 252:1523-1528 (1991).
Huang et al., J. Biol. Chem. 267:5467-5473 (1992).
Hutchcroft et al., Proc. Natl. Acad. Sci. USA 89:9107-9111 (1992).
Hutchcroft et al., J. Biol. Chem. 266:14846-14849 (1991).
Hutchcroft et al., J. Biol. Chem. 267:8613-8619 (1992).
Irving et al., J. Exp. Med. 177:1093-1103 (1993).
June et al., J. Immunol. 144:1591-1599 (1990).
June et al., Proc. Natl. Acad. Sci. USA 87:7722-7726 (1990).
Karnitz et al., Mol. Cell. Biol. 12:4521-4530 (1992).
Koga et al., Eur. J. Immunol. 16:1643-1646 (1986).
Kolanus et al., EMBO J. 11:4861-4868 (1992).
Kroczek et al., Nature 322:181-184 (1986).
Lane et al., J. Immunol. 146:715-722 (1991).
Letourneur and Klausner, Science 255:79-82 (1992).
Letourneur and Klausner, Proc. Natl. Acad. Sci. USA 88:8905-8909 (1991).
Li et al., Mol. Cell. Biol. 12:3176-3182 (1992).
Luo and Sefton, Mol. Cell. Biol. 12:4724-4732 (1992).
Muller et al., Mol. Cell. Biol. 12:5087-5093 (1992).
Mustelin et al., Science 247:1584-1587 (1990).
Nishibe et al., Science 250:1253-1256 (1990).
Park et al., J. Biol. Chem. 266:24237-24240 (1991).
Park et al., Proc. Natl. Acad. Sci. USA 88:5453-5456 (1991).
Pendergast et al., Cell 66:161-171 (1991).
Rudd et al., Proc. Natl. Acad. Sci USA 85:5190-5194 (1988).
Samelson et al., Proc. Natl. Acad. Sci USA 87:4358-4362 (1990).
Secrist et al., J. Biol. Chem. 268:5886-5893 (1993).
Secrist et al., J. Biol. Chem. 266:12135-12139 (1991).
Stanley et al., J. Immunol. 145:2189-2198 (1990).
Stefanova et al., Science 254:1016-1019 (1991).
Shaw et al., Cell 59:627-636 (1989).
Stein et al., Cell 70:741-750 (1992).
Straus and Weiss, Cell 70:585-593 (1992).
Sugie et al., Proc. Natl. Acad. Sci. USA 88:9132-9135 (1991).
Thomas and Samelson, J. Biol. Chem. 267:1231-1232 (1992).
Tsygankov et al., J. Biol. Chem. 267:18259-18262 (1992).
Turner et al., Cell 60:755-765 (1990).
Veillette et al., Cell 55:301-308 (1988).
Wange et al., J. Biol. Chem. 267:11685-11688 (1992).
Webb et al., Science 249:1295-1297 (1990).
Weiss et al., Annu. Rev. Genet. 25:487-510 (1991).
Wong et al., Oncogene 7:2401-2415 (1992).
Yamanashi et al., Science 251:192-194 (1991).
Yeh et al., J. Immunol. 138:91-97 (1987).
Yokoyama and Shevach, Year Immunol. 4:110-146 (1989).
Zioncheck et al., J. Biol. Chem. 263:19195-19202 (1988).
Zioncheck et al., J. Biol. Chem. 261:15637-15643 (1986).
Littman et al., Cell 40:237 (1985).
Kinet, Cell 57:351 (1989).
Riedel et al., Nature 324:68 (1986).
Riedel et al., EMBO J. 8:2943 (1989).
Accolla, J. Exp. Med. 157:1053-1058 (1983).
Anderson et al., Proc. Natl. Acad. Sci. USA 87:2274-2278 (1990).
Anderson et al., Nature 341:159-162 (1989).
Aruffo et al., Proc. Natl. Sci. USA 84:8573-8577 (1987).
Aruffo and Seed, EMBO J. 6:3313 (1987).
Ashorn et al., J. Virol. 64:2149 (1990).
Baniyash et al., J. Biol. Chem. 263:9874-9878 (1988).
Bauer et al., Proc. Natl. Acad. Sci. USA 88:3842 (1991).
Becker et al., Biochemistry 51:577-585 (1964).
Becker et al., Cell 58:911-921 (1989).
Berke et al., "T Lymphocte-Mediated Cytolysis—A Comprehensive Theory", The Mechanism of CTL-Mediated Cytolysis, Mechanisms of Cell Mediated Cytotoxicity pp. 57-73 (1992).
Berke, Immunological Rev. 72:5-42 (1983).
Berke, Immunology Today 12:396-399 (1991).
Berkhout et al., J. Biol. Chem. 263:8528-8536 (1988).
Blank et al., Nature 337:187-189 (1989).
Blumberg et al., J. Infectious Diseases 156:878-883 (1987).
Blumberg et al., J. Biol. Chem. 265:14036 (1990).
Boyle et al., Gene 65:123-128 (1988).
Breitmeyer et al., J. Immunol. 138:726 (1987).
Buonocore et al., Nature 345:625-628 (1990).
Byrn et al., Nature 344:667-670 (1990).
Capon et al., Nature 337:525-531 (1989).
Carr et al., J. Biol. Chem. 264:21286-21295 (1989).
Chakrabarti et al., Nature 320:535-537 (1986).
Chaudhary et al., Nature 335:369-372 (1988).
Chan et al, Cell 71:649-662 (1992).
Clark et al., "T Lymphocte-Mediated Cytolysis—A Comprehensive Theory", Lytic vs. Nonlytic Interactions of T Lymphocytes pp. 69-73.
Clayton et al., J. Exp. Med. 172:1243-1253 (1990).
Clayton et al., Proc. Natl. Acad. Sci. USA 88:5202 (1991).
Cline, Schweiz. med. Wschr. 116:1459-1464 (1986).
Dalgleish et al., Nature 312:763-767 (1984).
Deen et al., Nature 331:82-84 (1988).
Denny et al., Nature 320:549-551 (1986).
Doyle et al., Nature 330:256-259 (1987).
Earl et al., J. Virol. 64:2448-2451 (1990).
Falkner et al., J. Virol. 62:1849-1854 (1988).
Fanger et al., Immunology Today 10:92-99 (1989).
Fisher et al., Nature 331:76-78 (1988).
Fleit et al., Proc. Natl. Acad. Sci. USA 79:3275-3279 (1982).
Frank et al., Science 249:174-177 (1990).
Friedman et al., Nature 335:452-454 (1988).
Grynkiewicz et al., J. Biol. Chem. 260:3440-3450 (1985).
Gauen et al., Mol. Cell. Biol. 12:5438-5446 (1992).
Gay et al., Nature 328:626-629 (1987).
Goldstein et al., Immunol. Rev. 68:5-42 (1982).
Gorny et al., Proc. Natl. Acad. Sci. USA 86:1624 (1989).
Goverman et al., Cell 60:929-939 (1990).
Green et al., Cell 58:215-223 (1989).
Gross et al., Proc. Natl. Acad. Sci. USA 86:10024-10028 (1989).
Haynes, Science 260:1279-1293 (1993).

Hermanson et al., Proc. Natl. Acad. Sci. USA 85:6890-6894 (1988).
Hibbs et al., Science 246:1608-1611 (1989).
Hildreth et al., Science 244:1075-1078 (1989).
Hoffenbach et al., J. Immunol. 452-462 (1989).
Hussey et al., Nature 331:78-81 (1988).
Irving and Weiss, Cell 64: 891-901 (1991).
Jenkins et al., Immunological Reviews 95:113-135 (1987).
Jin et al., Proc. Natl. Acad. Sci. USA 87:3319-3323 (1990).
Johnston et al., Science 260:1286-1293 (1993).
Klatzmann et al., Nature 312:767-768 (1984).
Kolanus et al., Cell 74:1-20 (1993).
Kohler et al., Eur. J. Immunol. 6:511 (1976).
Kohler et al., Nature 256:495 (1975).
Kohler et al., Eur. J. Immunol. 6:292 (1976).
Krissansen et al., EMBO J. 5:1799-1808 (1986).
Kurosaki et al., Nature 342:805-807 (1989).
Kuster et al., J. Biol. Chem. 265:6448-6452 (1990).
Kuwana et al., Biochem. Biophy. Res. Comm. 149:960-968 (1987).
Lamarre et al., Science 245:743-746 (1989).
Lanier et al., Nature 342:803-805 (1989).
Lawson et al., J. Biol. Chem. 263:14812-14818 (1988).
Lifson et al., Nature 323:725-728 (1986).
Lifson et al., Science 241:712-716 (1988).
Maddon et al., Cell 47:333-348 (1986).
Malim et al., Cell 58:205-214 (1989).
Marasco et al., J. Clin. Invest. 90:1467 (1992).
McDougal et al., Science 231:382 (1986).
Mellman, Curr. Opin. Immunol. 1:16-25 (1988).
Mercep et al., Science 242:571-574 (1988).
Mercep et al., Science 246:1162-1165 (1989).
Miettinen et al., Cell 58:317-327 (1989).
Morley et al., J. Exp. Med. 168:1971-1978 (1988).
Oettgen et al., Nature 320:272-275 (1986).
Orloff et al., Nature 347:189-191 (1990).
Ohashi et al., Nature 316:606-609 (1985).
Ostergaard et al., J. Immunol. 139:3573-3579 (1987).
Perussia et al., J. Exp. Med. 170:73-86 (1989).
Potocnjak, et al., Science 215:1637 (1982).
Qiu et al., Science 248:732-735 (1990).
Ra et al., J. Biol. Chem. 264:15323-15327 (1989).
Ra et al., Nature 341:752-754 (1989).
Rabinovitch et al., J. Immunol. 137:952:961 (1986).
Ravetch et al., J. Exp. Med 170:481-497 (1989).
Ravetch and Kinet, Annu. Rev. Immunol. 9:457-492 (1991).
Reinherz and Schlossman, Cell 19:821-827 (1980).
Reinherz et al., Proc. Natl. Sci. USA 76:4061-4065 (1979).
Reth, Nature 338:383 (1989).
Rice et al., J. Virol. 47:529-539 (1983).
Romeo et al., Cell 64:1037-1046 (1991).
Romeo et al., Cold Spring Harbor Symposia on Quantitative Biology, LVII:117-125 (1992).
Romeo et al., Cell 68:889-897 (1992).
Rosenberg et al., New Eng. J. Med. 323:570-578 (1990).
Rosenberg, Scientific American 62-69 (1990).
Sakaguchi et al., EMBO J. 7:3457-3464 (1988).
Samelson et al., Cell 43:223-231 (1985).
Sancho et al., J. Biol. Chem. 264:20760 (1989).
Sattentau et al., Cell 52:631-633 (1988).
Schwartz et al., Science 248:1349-1356 (1990).
Schwartz et al., Cell 71:1065-1068 (1992).
Sharpira-Nahor et al., J. Immunol. 139:35-36 (1987).
Shen et al., Molecular Immunol. 26:959 (1989).
Sleckman et al., Nature 328:351-353 (1987).
Smith et al., Science 238:1704-1707 (1987).
Sodroski et al., Nature 322:470-477 (1986).
Sodroski et al., Nature 321:412-417 (1986).
Sussman et al., Cell 52:85-95 (1988).
Till et al., Science 242:1166-1168 (1988).
Tirosh et al., Cellular Immunology 95:113-123 (1985).
Traunecker et al., Nature 331:84-86 (1988).
Traunecker et al., Nature 339:68-70 (1989).
Trenn et al., Nature 330:72-74 (1987).
Wacholtz et al., J. Immunology 150:5338-5349 (1993).
Wands et al. Gastroenterology 80:225-232 (1981).
Watanabe et al., Nature 337:267-270 (1989).
Weiss et al., J. Immunol. 133:123-128 (1984).
Wegener et al., Cell 68:83-95 (1992).
Weiss et al., Nature 324:572-575 (1986).
Weiss et al., Cold Spring Harbor Symposia on Quantitiative Biology LVII:107-116 (1992).
Weiss et al., J. Exp. Med. 160:1284-1299 (1984).
Weissman et al., Proc. Natl. Acad. Sci. USA 85:9709-9713 (1988).
Weissman et al., Nature 324:480-482 (1986).
Weissman et al., Science 239:1018-1021 (1988).
Weissman et al., EMBO J. 8:3651-3656 (1989.
Yague et al., Cell 42:81-87 (1985).
Yoffe et al., Proc. Natl. Acad. Sci. USA 84:1429-1433 (1987).
Young et al., J. Exp. Med. 166:1884-1889 (1987).
Zettlmeissl et al., DNA and Cell Biology 9:347-353 (1990).
Trono et al., Cell 59:113-120 (1989).
Tunnacliffe et al., EMBO J. 6:2953-2957 (1987).
Unkeless et al., Annu. Rev. Immunol 6:251-281 (1988).
Valentin et al., J. Immunol. 144:934-937 (1990).
van den Elsen et al., Proc. Natl. Acad. Sci. USA 83:2944-2948 (1986).
Orloff et al., J. Biol. Chem. 264:14812-14817 (1989).
Al-Jaufy et al., Infection and Immunity 62:956-960 (1994).
Aullo et al., EMBO J. 11:575-583 (1992).
Chao et al., J. Biol. Chem. 264:5812-5817 (1989).
Lin et al., FASEB J. 7:1070-1080 (1993).
Moebius et al., J. Exp. Med. 176:507-517 (1992).
Sekigawa et al., J. Virol. 64:5194-5198 (1990).

* cited by examiner

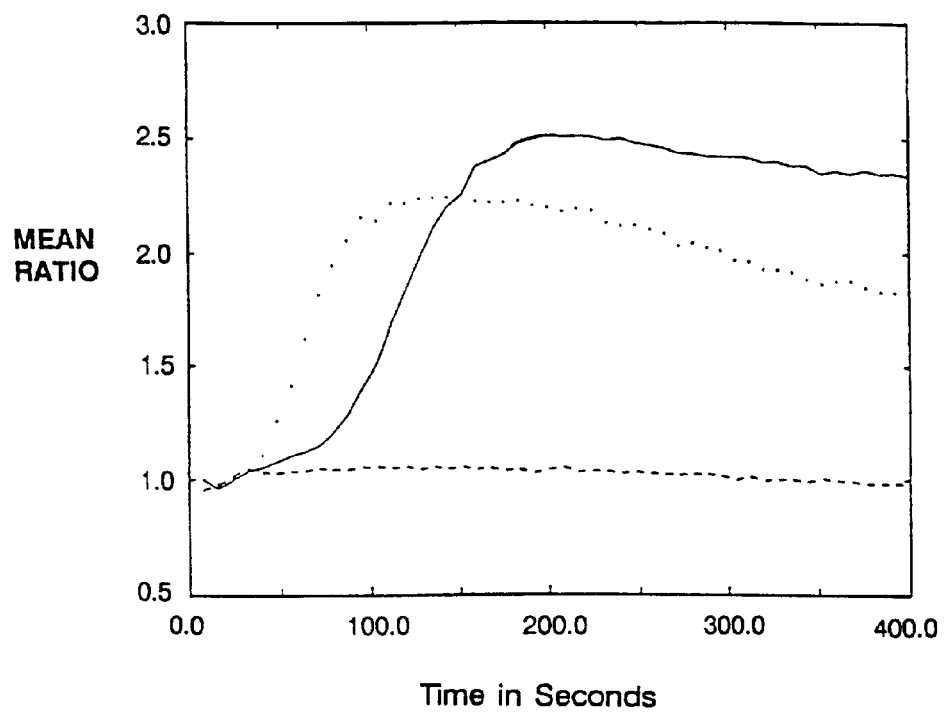
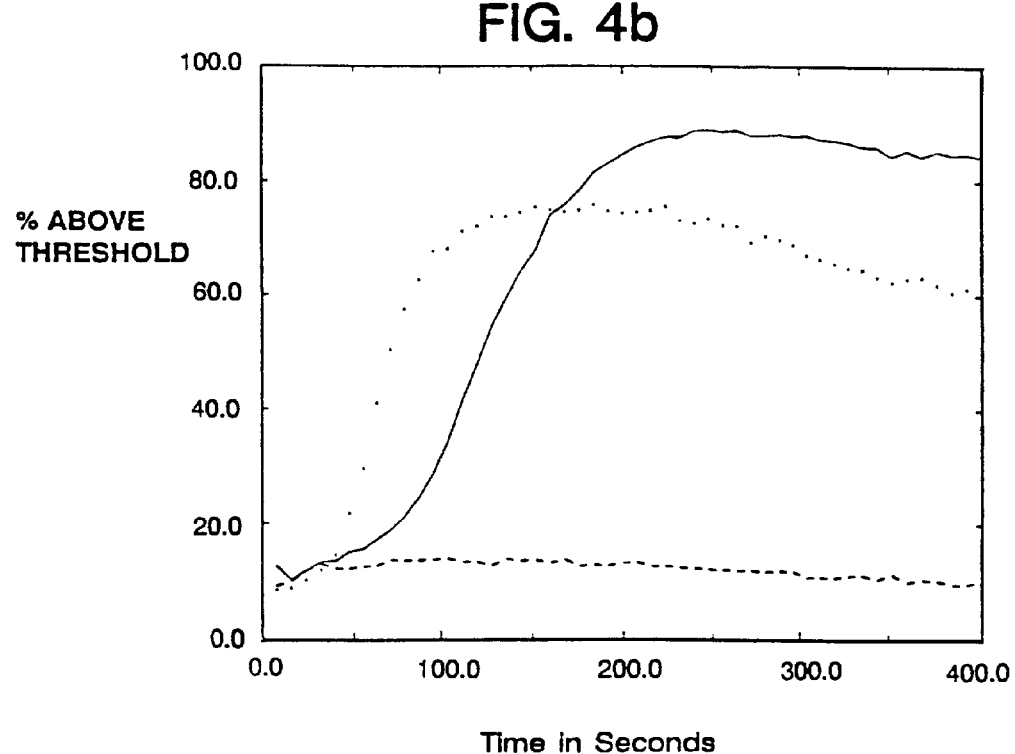

QSFGLLDPKLCYLLDG ζ

189
--FSPPGADPKLCYLLDG CD16:ζ

```
                                          F34*                  Y51*
  1  QSFGLLDPKL  CYLLDGILFI  YGVILTALFL  RVKFSRSAEP  PAYQQGQNQL
                                              ←⎦                  ←⎦
         E60*       D66*
 51  YNELNLGRRE  EYDVLDKRRG  RDPEMGGKPR  RKNPQEGLYN  ELQKDKMAEA
         ←⎦         ←⎦
                              G122*       A133*       L139*
101  YSEIGMKGER  RRGKGHDGLY  QGLSTATKDT  YDALHMQALP  PR
                                ←⎦          ←⎦       ←⎦
```

FIG.16 (Seq. ID No: 24)

```
1    MEHSTFLSGL  VLATLLSQVS  PFKIPIEELE  DRVFVNCNTS  ITWVEGTVGT
51   LLSDITRLDL  GKRILDPRGI  YRCNGTDIYK  DKESTVQVHY  RMCQSCVELD
101  PATVAGIIVT  DVIATLLLAL  GVFCFAGHET  GRLSGAADTQ  ALLRNDQVYQ
151  PLRDRDDAQY  SHLGGNWARN  K*
```

FIG.17 (Seq ID NO: 25)

```
1    MEQGKGLAVL  ILAIILLQGT  LAQSIKGNHL  VKVYDYQEDG  SVLLTCDAEA
51   KNITWFKDGK  MIGFLTEDKK  KWNLGSNAKD  PRGMYQCKGS  QNKSKPLQVY
101  YRMCQNCIEL  NAATISGFLF  AEIVSIFVLA  VGVYFIAGQD  GVRQSRASDK
151  QTLLPNDQLY  QPLKDREDDQ  YSHLQGNQLR  RN*
```

FIG.18 (Seq ID No: 26)

```
1    MPGGLEALRA  LPLLLFLSYA  CLGPGCQALR  VEGGPPSLTV  NLGEEARLTC
51   ENNGRNPNIT  WWFSLQSNIT  WPPVPLGPGQ  GTTGQLFFPE  VNKNTGACTG
101  CQVIENNILK  RSCGTYLRVR  NPVPRPFLDM  GEGTKNRIIT  AEGIILLFCA
151  VVPGTLLLFR  KRWQNEKFGV  DMPDDYEDEN  LYEGLNLDDC  SMYEDISRGL
201  QGTYQDVGNL  HIGDAQLEKP  *
```

FIG.19 (Seq ID No: 27)

```
1    MATLVLSSMP  CHWLLFLLLL  FSGEPVPAMT  SSDLPLNFQG  SPCSQIWQHP
51   RFAAKKRSSM  VKFHCYTNHS  GALTWFRKRG  SQQPQELVSE  EGRIVQTQNG
101  SVYTLTIQNI  QYEDNGIYFC  KQKCDSANHN  VTDSCGTELL  VLGFSTLDQL
151  KRRNTLKDGI  ILIQTLLIIL  FIIVPIFLLL  DKDDGKAGME  EDHTYEGLNI
201  DQTATYEDIV  TLRTGEVKWS  VGEHPGQE*
```

REDIRECTION OF CELLULAR IMMUNITY BY RECEPTOR CHIMERAS

This application is a continuation of application, Seed et al., U.S. Ser. No. 08/394,176, filed Feb. 24, 1995, now abandoned.

FIELD OF THE INVENTION

The invention concerns functional T cell receptor, Fc receptor, or B cell receptor chimeras which are capable of redirecting immune system function. More particularly, it concerns the regulation of lymphocytes, macrophages, natural killer cells or granulocytes by the expression in said cells of chimeras which cause the cells to respond to targets recognized by the chimeras. The invention also concerns functional T cell receptor, Fc receptor, or B cell receptor chimeras which are capable of directing therapeutic cells to specifically recognize and destroy either cells infected with a specific infective agent, the infective agent itself, a tumor cell, or an autoimmune-generated cell. More particularly, the invention relates to the production of T cell receptor, Fc receptor, or B cell receptor chimeras capable of directing cytotoxic T lymphocytes to specifically recognize and lyse cells expressing HIV envelope proteins. The invention therefore provides a therapy for diseases such as AIDS (Acquired Immunodeficiency Syndrome) which are caused by the HIV virus.

BACKGROUND OF THE INVENTION

T cell recognition of antigen through the T cell receptor is the basis of a range of immunological phenomena. The T cells direct what is called cell-mediated immunity. This involves the destruction by cells of the immune system of foreign tissues or infected cells. A variety of T cells exist, including "helper" and "suppressor" cells, which modulate the immune response, and cytotoxic (or "killer") cells, which can kill abnormal cells directly.

A T cell that recognizes and binds a unique antigen displayed on the surface of another cell becomes activated; it can then multiply, and, if it is a cytotoxic cell, it can kill the bound cell.

Autoimmune disease is characterized by production of either antibodies that react with host tissue or immune effector T cells that are autoreactive. In some instances, autoantibodies may arise by a normal T- and B-cell response activated by foreign substances or organisms that contain antigens that cross react with similar compounds in body tissues. Examples of clinically relevant autoantibodies are antibodies against acetylcholine receptors in myasthenia gravis; and anti-DNA, anti-erythrocyte, and anti-platelet antibodies in systemic lupus erythematosus.

HIV and Immunopathogenesis

In 1984 HIV was shown to be the etiologic agent of AIDS. Since that time the definition of AIDS has been revised a number of times with regard to what criteria should be included in the diagnosis. However, despite the fluctuation in diagnostic parameters, the simple common denominator of AIDS is the infection with HIV and subsequent development of persistent constitutional symptoms and AIDS-defining diseases such as a secondary infections, neoplasms, and neurologic disease. *Harrison's Principles of Internal Medicine,* 12th ed., McGraw Hill (1991).

HIV is a human retrovirus of the lentivirus group. The four recognized human retroviruses belong to two distinct groups: the human T lymphotropic (or leukemia) retroviruses, HTLV-1 and HTLV-2, and the human immunodeficiency viruses, HIV-1 and HIV-2. The former are transforming viruses whereas the latter are cytopathic viruses.

HIV-1 has been identified as the most common cause of AIDS throughout the world. Sequence homology between HIV-2 and HIV-1 is about 40% with HIV-2 being more closely related to some members of a group of simian immunodeficiency viruses (SIV). See Curran et al., *Science* 329:1357–1359 (1985); Weiss et al., *Nature* 324:572–575 (1986).

HIV has the usual retroviral genes (env, gag, and pol) as well as six extra genes involved in the replication and other biologic activities of the virus. As stated previously, the common denominator of AIDS is a profound immunosuppression, predominantly of cell-mediated immunity. This immune suppression leads to a variety of opportunistic diseases, particularly certain infections and neoplasms.

The main cause of the immune defect in AIDS has been identified as a quantitative and qualitative deficiency in the subset of thymus-derived (T) lymphocytes, the T4 population. This subset of cells is defined phenotypically by the presence of the CD4 surface molecule, which has been demonstrated to be the cellular receptor for HIV. Dalgleish et al., *Nature* 312:763 (1984). Although the T4 cell is the major cell type infected with HIV, essentially any human cell that expresses the CD4 molecule on its surface is capable of binding to and being infected with HIV.

Traditionally, $CD4^+$ T cells have been assigned the role of helper/inducer, indicating their function in providing an activating signal to B cells, or inducing T lymphocytes bearing the reciprocal CD8 marker to become cytotoxic/suppressor cells. Reinherz and Schlossman, *Cell* 19:821–827 (1980); Goldstein et al., *Immunol. Rev.* 68:5–42 (1982).

HIV binds specifically and with high affinity, via a stretch of amino acids in the viral envelope (gp120), to a portion of the V1 region of the CD4 molecule located near its N-terminus. Following binding, the virus fuses with the target cell membrane and is internalized. Once internalized it uses the enzyme reverse transcriptase to transcribe its genomic RNA to DNA, which is integrated into the cellular DNA where it exists for the life of the cell as a "provirus."

The provirus may remain latent or be activated to transcribe mRNA and genomic RNA, leading to protein synthesis, assembly, new virion formation, and budding of virus from the cell surface. Although the precise mechanism by which the virus induces cell death has not been established, it is believed that the major mechanism is massive viral budding from the cell surface, leading to disruption of the plasma membrane and resulting osmotic disequilibrium.

During the course of the infection, the host organism develops antibodies against viral proteins, including the major envelope glycoproteins gp120 and gp41. Despite this humoral immunity, the disease progresses, resulting in a lethal immunosuppression characterized by multiple opportunistic infections, parasitemia, dementia, and death. The failure of the host anti-viral antibodies to arrest the progression of the disease represents one of the most vexing and alarming aspects of the infection, and augurs poorly for vaccination efforts based upon conventional approaches.

Two factors may play a role in the efficacy of the humoral response to immunodeficiency viruses. First, like other RNA viruses (and like retroviruses in particular), the immunodeficiency viruses show a high mutation rate in response to host immune surveillance. Second, the envelope glycoproteins themselves are heavily glycosylated molecules presenting few epitopes suitable for high affinity antibody binding. The poorly antigenic target which the viral envelope presents allows the host little opportunity for restricting viral infection by specific antibody production.

Cells infected by the HIV virus express the gp120 glycoprotein on their surface. Gp120 mediates fusion events among CD4+ cells via a reaction similar to that by which the virus enters the uninfected cells, leading to the formation of short-lived multinucleated giant cells. Syncytium formation is dependent on a direct interaction of the gp120 envelope glycoprotein with the CD4 protein. Dalgleish et al., supra; Klatzman et al., *Nature* 312:763 (1984); McDougal et al., *Science* 231:382 (1986); Sodroski et al., *Nature* 322:470 (1986); Lifson et al., *Nature* 323:725 (1986); Sodroski et al., *Nature* 321:412 (1986).

Evidence that the CD4-gp120 binding is responsible for viral infection of cells bearing the CD4 antigen includes the finding that a specific complex is formed between gp120 and CD4 (McDougal et al., supra). Other investigators have shown that the cell lines, which were non-infective for HIV, were converted to infectable-cell lines following transfection and expression of the human CD4 cDNA gene. Maddon et al., *Cell* 46:333–348 (1986).

Therapeutic programs based on soluble CD4 as a passive agent to interfere with viral adsorption and syncytium-mediated cellular transmission have been proposed and successfully demonstrated in vitro by a number of groups (Deen et al., *Nature* 331:82–84 (1988); Fisher et al., *Nature* 331:76–78 (1988); Hussey et al., *Nature* 331:78–81 (1988); Smith et al., *Science* 238:1704–1707 (1987); Traunecker et al., *Nature* 331:84–86 (1988)); and CD4 immunoglobulin fusion proteins with extended half-lives and modest biological activity have subsequently been developed (Capon et al., *Nature* 337:525–531 (1989); Traunecker et al. *Nature* 339, 68–70 (1989); Byrn et al., *Nature* 344:667–670 (1990); Zettlmeissl et al., *DNA Cell Biol.* 9:347–353 (1990)). Although CD4 immunotoxin conjugates or fusion proteins show potent cytotoxicity for infected cells in vitro (Chaudhary et al., *Nature* 335:369–372 (1988); Till et al., *Science* 242:1166–1168 (1988)), the latency of the immunodeficiency syndrome makes it unlikely that any single-treatment therapy will be effective in eliminating viral burden, and the antigenicity of foreign fusion proteins is likely to limit their acceptability in treatments requiring repetitive dosing. Trials with monkeys affected with SIV have shown that soluble CD4, if administered to animals without marked CD4 cytopenia, can reduce SIV titer and improve in vitro measures of myeloid potential (Watanabe et al., *Nature* 337:267–270 (1989)). However a prompt viral reemergence was observed after treatment was discontinued, suggesting that lifelong administration might be necessary to prevent progressive immune system debilitation.

T Cell and Fc Receptors

Cell surface expression of the most abundant form of the T cell antigen receptor (TCR) requires the coexpression of at least 6 distinct polypeptide chains (Weiss et al., *J. Exp. Med.* 160:1284–1299 (1984); Orloffhashi et al., *Nature* 316:606–609 (1985); Berkhout et al., *J. Biol. Chem.* 263: 8528–8536 (1988); Sussman et al., *Cell* 52:85–95 (1988)), the α/β antigen binding chains, the three polypeptides of the CD3 complex, and ζ. If any of the chains are absent, stable expression of the remaining members of the complex does not ensue. ζ is the limiting polypeptide for surface expression of the complete complex (Sussman et al., *Cell* 52:85–95 (1988)) and is thought to mediate at least a fraction of the cellular activation programs triggered by receptor recognition of ligand (Weissman et al., *EMBO J.* 8:3651–3656 (1989); Frank et al., *Science* 249:174–177 (1990)). A 32 kDa type I integral membrane homodimer, ζ (zeta) has a 9 residue extracellular domain with no sites for N-linked glycan addition, and a 112 residue (mouse) or 113 residue (human) intracellular domain (Weissman et al., *Science* 238:1018–1020 (1988); Weissman et al., *Proc. Natl. Acad. Sci. USA* 85:9709–9713 (1988)). An isoform of ζ called η (eta) (Baniyash et al., *J. Biol. Chem.* 263:9874–9878 (1988); Orloff et al., *J. Biol. Chem.* 264:14812–14817 (1989)), which arises from an alternate mRNA splicing pathway (Jin et al., *Proc. Natl. Acad. Sci. USA* 87:3319–3233 (1990)), is present in reduced amounts in cells expressing the antigen receptor. ζ-η heterodimers are thought to mediate the formation of inositol phosphates, as well as the receptor-initiated programmed cell death called apoptosis (Merćep et al., *Science* 242:571–574 (1988); Merćep et al., *Science* 246:1162–1165 (1989)).

Like ζ and η, the Fc receptor-associated γ (gamma) chain is expressed in cell surface complexes with additional polypeptides, some of which mediate ligand recognition, and others of which have undefined function. γ bears a homodimeric structure and overall organization very similar to that of ζ and is a component of both the mast cell/basophil high affinity IgE receptor, FcεRI, which consists of at least three distinct polypeptide chains (Blank et al., *Nature* 337: 187–189 (1989); Ra et al., *Nature* 241:752–754 (1989)), and one of the low affinity receptors for IgG, represented in mice by FcγRIIα (Ra et al., *J. Biol. Chem.* 264:15323–15327 (1989)), and in humans by the CD16 subtype expression by macrophages and natural killer cells, $CD16_{TM}$ (CD16 transmembrane) (Lanier et al., *Nature* 342:803–805 (1989); Anderson et al., *Proc. Natl. Acad. Sci. USA* 87:2274–2278 (1990)) and with a polypeptide of unidentified function (Anderson et al., *Proc. Natl. Acad. Sci. USA* 87:2274–2278 (1990)). Recently it has been reported that γ is expressed by a mouse T cell line, CTL, in which it forms homodimers as well as γ-ζ and γ-η heterodimers (Orloff et al., *Nature* 347:189–191 (1990)).

The Fc receptors mediate phagocytosis of immune complexes, transcytosis, and antibody dependent cellular cytotoxicity (ADCC) (Ravetch and Kinet, *Annu. Rev. Immunol.* 9:457–492 (1991); Unkeless et al., *Annu. Rev. Immunol* 6:251–281 (1988); and Mellman, *Curr. Opin. Immunol.* 1:16–25 (1988)). Recently it has been shown that one of the murine low affinity Fc receptor isoforms, FcRγIIIB1, mediates internalization of Ig-coated targets into clathrin coated pits, and that another low affinity receptor, FcRγIIIA mediates ADCC through its association with one or more members of a small family of 'trigger molecules' (Miettinen et al., *Cell* 58:317–327 (1989); and Hunziker and Mellman, *J. Cell Biol.* 109:3291–3302 (1989)). These trigger molecules, T cell receptor (TCR) ζ chain, TCR η chain, and Fc receptor γ chain, interact with ligand recognition domains of different immune system receptors and can autonomously initiate cellular effector programs, including cytolysis, following aggregation (Samelson et al., *Cell* 43:223–231 (1985); Weissman et al., *Science* 239:1018–1020 (1988); Jin et al., *Proc. Natl. Acad. Sci. USA* 87:3319–3323 (1990); Blank et al., *Nature* 337:187–189 (1989); Lanier et al., *Nature* 342: 803–805 (1989); Kurosaki and Ravetch, *Nature* 342:805–807 (1989); Hibbs et al., *Science* 246:1608–1611 (1989); Anderson et al., *Proc. Natl. Acad. Sci USA* 87:2274–2278 (1990); and Irving and Weiss, *Cell* 64: 891–901 (1991)).

In drawing parallels between the murine and human low affinity Fc receptor families, however, it has become clear that the human FcRγIIA and C isoforms have no murine counterpart. In part because of this, their function has yet to be defined.

Because humoral agents based on CD4 alone may have limited utility in vivo, previous work explored the possibility of augmenting cellular immunity to HIV. Preparations of protein chimeras in which the extracellular domain of CD4 is fused to the transmembrane and/or intracellular domains of T cell receptor, IgG Fc receptor, or B cell receptor signal transducing elements have been identified (U.S. Ser. Nos. 07/847,566 and 07/665,961, hereby incorporated by reference). Cytolytic T cells expressing chimeras which include an extracellular CD4 domain show potent MHC-independent destruction of cellular targets expressing HIV envelope proteins. An extremely important and novel component of this approach has been the identification of single T cell receptor, Fc receptor, and B cell receptor chains whose aggregation suffices to initiate the cellular response.

One particularly useful application of this approach has been the invention of chimeras between CD4 and ζ, η, or γ that direct cytolytic T lymphocytes to recognize and kill cells expressing HIV gp120 (U.S. Ser. Nos. 07/847,566 and 07/665,961, hereby incorporated by reference).

SUMMARY OF THE INVENTION

Although native T cell, B cell, and Fc receptors are or can be highly complicated multimeric structures not lending themselves to convenient manipulation, the present invention demonstrates the feasibility of creating chimeras between the intracellular domain of any of a variety of molecules which are capable of fulfilling the task of target recognition. In particular, the formation of chimeras consisting of the intracellular portion of T cell/Fc receptor zeta, eta, or gamma chains joined to the extracellular portion of a suitably engineered antibody molecule allows the target recognition potential of an immune system cell to be specifically redirected to the antigen recognized by the extracellular antibody portion. Thus with an antibody portion capable of recognizing some determinant on the surface of a pathogen, immune system cells armed with the chimera would respond to the presence of the pathogen with the effector program appropriate to their lineage, e.g., helper T lymphocytes would respond by cytotoxic activity against the target, and B lymphocytes would be activated to synthesize antibody. Macrophages and granulocytes would carry out their effector programs, including cytokine release, phagocytosis, and reactive oxygen generation. Similarly, with an antibody portion capable of recognizing tumor cells, the immune system response to the tumor would be beneficially elevated. With an antibody capable of recognizing immune cells having an inappropriate reactivity with self determinants, the autoreactive cells could be selectively targeted for destruction.

Although these examples draw on the use of antibody chimeras as a convenient expository tool, the invention is not limited in scope to antibody chimeras, and indeed, the use of specific nonantibody extracellular domains may have important advantages. For example with an extracellular portion that is the receptor for a virus, bacterium, or parasite, cells armed with the chimeras would specifically target cells expressing the viral, bacterial, or parasitic determinants. The advantage of this approach over the use of antibodies is that the native receptor for pathogen may have uniquely high selectivity or affinity for the pathogen, allowing a greater degree of precision in the resulting immune response. Similarly, to delete immune system cells which inappropriately react with a self antigen, it may suffice to join the antigen (either as an intact protein, in the case of B cell depletion therapies, or as MHC complex, in the case of T cell depletion therapies) to intracellular zeta, eta, or gamma chains, and thereby affect the specific targeting of the cells inappropriately responding to self determinants.

Another use of the chimeras is the control of cell populations in vivo subsequent to other forms of genetic engineering. For example, the use of tumor infiltrating lymphocytes or natural killer cells to carry cytotoxic principles to the site of tumors has been proposed. The present invention provides a convenient means to regulate the numbers and activity of such lymphocytes and cells without removing them from the body of the patient for amplification in vitro. Thus, because the intracellular domains of the chimeric receptors mediate the proliferative responses of the cells, the coordination of the extracellular domains by a variety of aggregating stimuli specific for the extracellular domains (e.g., an antibody specific for the extracellular domain) will result in proliferation of the cells bearing the chimeras.

Although the specific embodiments of the present invention comprise chimeras between zeta, eta, or gamma chains, or active fragments thereof (e.g., those discussed below), any receptor chain having a similar function to these molecules, e.g., in granulocytes or B lymphocytes, could be used for the purposes disclosed here. The distinguishing features of desirable immune cell trigger molecules comprise the ability to be expressed autonomously (i.e., as a single chain), the ability to be fused to an extracellular domain such that the resultant chimera is present on the surface of a therapeutic cell, and the ability to initiate cellular effector programs upon aggregation secondary to encounter with a target ligand.

At present the most convenient method for delivery of the chimeras to immune system cells is through some form of genetic therapy. However, reconstituting immune system cells with chimeric receptors by mixture of the cells with suitably solubilized purified chimeric protein would also result in the formation of an engineered cell population capable of responding to the targets recognized by the extracellular domain of the chimeras. Similar approaches have been used, for example, to introduce the intact HIV receptor, CD4, into erythrocytes for therapeutic purposes. In this case the engineered cell population would not be capable of self renewal.

The present invention relates to functional simplified T cell receptor, B cell receptor, and Fc receptor chimeras which are capable of redirecting immune system function. More particularly, it relates to the regulation of lymphocytes, macrophages, natural killer cells, or granulocytes by the expression in said cells of chimeras which cause the cells to respond to targets recognized by the chimeras. The invention also relates to a method of directing cellular responses to an infective agent, a tumor or cancerous cell, or an autoimmune-generated cell. The method for directing the cellular response in a mammal comprises administering an effective amount of therapeutic cells to said mammal, said cells being capable of recognizing and destroying said infective agent, tumor, cancer cell or autoimmune generated cell. The cellular response may be mediated by a single receptor chimera or may be the result of cooperation between multiple chimeras (for example, a set of two or more chimeras, one of which includes a CD28 intracellular domain).

In another embodiment, the method of directing cellular response to an infective agent comprises administering therapeutic cells capable of recognizing and destroying said agent, wherein the agent is a specific virus, bacteria, protozoa, or fungi. Even more specifically, the method is directed against agents such as HIV and *Pneumocystis carinii.*

Specifically the invention provides for a method of directing cellular response to an HIV-infected cell. The method comprises administering to a patient an effective amount of cytotoxic T lymphocytes, said lymphocytes being capable of specifically recognizing and lysing cells infected with HIV as well as circulating virus.

Thus, in one embodiment, there is provided according to the invention a method for directing cellular response to HIV-infected cells, comprising administering to a patient an effective amount of cytotoxic T lymphocytes which are capable of specifically recognizing and lysing cells infected with HIV.

In yet another embodiment is provided the chimeric receptor proteins which direct the cytotoxic T lymphocytes to recognize and lyse the HIV-infected cell. Yet another embodiment of the invention comprises host cells transformed with a vector comprising the chimeric receptors.

In yet another embodiment, the present invention provides for an antibody against the chimeric receptors of the invention.

In order to obtain cytotoxic T lymphocytes which specifically bind and lyse cells infected with HIV, the present inventors therefore attempted, and herein provide receptor chimeras. These chimeric receptors are functionally active and possess the extraordinary ability of being able to specifically bind and lyse cells expressing gp120.

It is an object of the present invention, then, to provide for a method of treatment for individuals infected with HIV. The present invention thus provides a number of important advances in the therapy of AIDS.

These and other non-limiting embodiments of the present invention will be apparent to those of skill from the following detailed description of the invention.

In the following detailed description, reference will be made to various methodologies known to those of skill in the art of molecular biology and immunology. Publications and other materials setting forth such known methodologies to which reference is made are incorporated herein by reference in their entireties as though set forth in full.

Standard reference works setting forth the general principles of recombinant DNA technology include Watson et al., *Molecular Biology of the Gene,* volumes I and II, the Benjamin/Cummings Publishing Company, Inc., publisher, Menlo Park, Calif. (1987); Darnell et al., *Molecular Cell Biology,* Scientific American Books, Inc., publisher, New York, N.Y. (1986); Lewin, *Genes II,* John Wiley & Sons, publishers, New York, N.Y. (1985); Old et al., *Principles of Gene Manipulation: An Introduction to Genetic Engineering,* 2nd edition, University of California Press, publisher, Berkeley, Calif. (1981); Maniatis et al., *Molecular Cloning: A Laboratory Manual,* 2nd ed., Cold Spring Harbor Laboratory, publisher, Cold Spring Harbor, N.Y. (1989); and *Current Protocols in Molecular Biology,* Ausubel et al., Wiley Press, New York, N.Y. (1989).

DEFINITIONS

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which comprise DNA copies of mRNA being expressed by the cell at the time the cDNA library was made. Such a cDNA library may be prepared by methods known to those of skill, and described, for example, in Maniatis et al., *Molecular Cloning: A Laboratory Manual,* supra. Generally, RNA is first isolated from the cells of an organism from whose genome it is desired to clone a particular gene. Preferred for the purpose of the present invention are mammalian, and particularly human, lymphocytic cell lines. A presently preferred vector for this purpose is the vaccinia virus WR strain.

By "vector" is meant a DNA molecule derived, e.g., from a plasmid, bacteriophage, or mammalian or insect virus, into which fragments of DNA may be inserted or cloned. A vector will contain one or more unique restriction sites and may be capable of autonomous replication in a defined host or vehicle organism such that the cloned sequence is reproducible. Thus, by "DNA expression vector" is meant any autonomous element capable of directing the synthesis of a recombinant peptide. Such DNA expression vectors include bacterial plasmids and phages and mammalian and insect plasmids and viruses.

By "substantially pure" is meant a compound, e.g., a protein, a polypeptide, or an antibody, that is substantially free of the components that naturally accompany it. Generally, a compound is substantially pure when at least 60%, more preferably at least 75%, and most preferably at least 90% of the total material in a sample is the compound of interest. Purity can be measured by any appropriate method, e.g., column chromatography, polyacrylamide gel electrophoresis, or HPLC analysis. In the context of a nucleic acid, "substantially pure" means a nucleic acid sequence, segment, or fragment that is not immediately contiguous with (i.e., covalently linked to) both of the coding sequences with which it is immediately contiguous (i.e. one at the 5' end and one at the 3' end) in the naturally occurring genome of the organism from which the DNA of the invention is derived.

By "functional derivative" is meant the "fragments," "variants," "analogues," or "chemical derivatives" of a molecule. A "fragment" of a molecule, such as any of the cDNA sequences of the present invention, is meant to refer to any nucleotide subset of the molecule. A "variant" of such molecule is meant to refer to a naturally occurring molecule substantially similar to either the entire molecule, or a fragment thereof. An "analog" of a molecule is meant to refer to a non-natural molecule substantially similar to either the entire molecule or a fragment thereof. A molecule is said to be "substantially similar" to another molecule if the sequence of amino acids in both molecules is substantially the same. In particular, a "substantially similar" amino acid sequence is one that exhibits at least 50%, preferably 85%, and most preferably 95% amino acid sequence identity to the natural or reference sequence and/or one that differs from the natural or reference amino acid sequence only by conservative amino acid substitutions. Substantially similar amino acid molecules possess similar biological activity. Thus, provided that two molecules possess a similar activity, they are considered variants as that term is used herein even if one of the molecules contains additional or fewer amino acid residues not found in the other, or if the sequence of amino acid residues is not identical. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences*, 16th ed., Mack Publishing Co., Easton, Pa. (1980).

Similarly, a "functional derivative" of a receptor chimera gene of the present invention is meant to include "fragments," "variants," or "analogues" of the gene, which may be "substantially similar" in nucleotide sequence, and which encode a molecule possessing similar activity to, for example, a T cell, B cell, or Fc receptor chimera. "Substantially similar" nucleic acids encode substantially similar amino acid sequences and also may include any nucleic acid sequence capable of hybridizing to the wild-type nucleic acid sequence under appropriate hybridization conditions (see, for example, Ausubel et al., *Current Protocols in Molecular Biology*, Wiley Press, New York, N.Y. (1989) for appropriate hybridization stringency conditions).

Thus, as used herein, a T cell, B cell, or Fc receptor chimera protein is also meant to include any functional derivative, fragments, variants, analogues, or chemical derivatives which may be substantially similar to the "wild-type" chimera and which possess similar activity (i.e., most preferably, 90%, more preferably, 70%, preferably 40%, or at least 10% of the wild-type receptor chimera's activity). The activity of a functional chimeric receptor derivative includes specific binding (with its extracellular portion) to a targeted agent or cell and resultant destruction (directed by its intracellular or transmembrane portion) of that agent or cell; such activity may be tested, e.g., using any of the assays described herein.

A DNA sequence encoding the T cell, B cell, or Fc receptor chimera of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis et al., supra, and are well known in the art.

A nucleic acid molecule, such as DNA, is said to be "capable of expressing" a polypeptide if it contains nucleotide sequences which contain transcriptional and translational regulatory information, and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a T cell receptor, B cell receptor, or Fc receptor chimera encoding sequence) are said to be operably linked if the nature of the linkage between the two DNA sequences does not (1) result in the introduction of a frame-shift mutation, (2) interfere with the ability of the promoter region sequence to direct the transcription of the receptor chimera gene sequence, or (3) interfere with the ability of the receptor chimera gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

The present invention encompasses the expression of a T cell receptor, B cell receptor, or Fc receptor chimera protein (or a functional derivative thereof) in either prokaryotic or eukaryotic cells, although eukaryotic (and, particularly, human lymphocyte) expression is preferred.

Antibodies according to the present invention may be prepared by any of a variety of methods. For example, cells expressing the receptor chimera protein, or a functional derivative thereof, can be administered to an animal in order to induce the production of sera containing polyclonal antibodies that are capable of binding the chimera.

In a preferred method, antibodies according to the present invention are monoclonal antibodies. Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563– 684 (1981)). In general, such procedures involve immunizing an animal with the T cell receptor, B cell receptor, or Fc receptor chimera antigen. The splenocytes of such animals are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding the chimera.

Antibodies according to the present invention also may be polyclonal, or, preferably, region specific polyclonal antibodies.

Antibodies against the T cell receptor, B cell receptor, or Fc receptor chimera according to the present invention may be used to monitor the amount of chimeric receptor (or chimeric receptor-bearing cells) in a patient. Such antibodies are well suited for use in standard immunodiagnostic assays known in the art, including such immunometric or "sandwich" assays as the forward sandwich, reverse sandwich, and simultaneous sandwich assays. The antibodies may be used in any number of combinations as may be determined by those of skill without undue experimentation to effect immunoassays of acceptable specificity, sensitivity, and accuracy.

Standard reference works setting forth general principles of immunology include Roitt, *Essential Immunology*, 6th ed., Blackwell Scientific Publications, publisher, Oxford (1988); Kimball, *Introduction to Immunology*, 2nd ed., Macmillan Publishing Co., publisher, New York (1986); Roitt et al., *Immunology*, Gower Medical Publishing Ltd., publisher, London, (1985); Campbell, "Monoclonal Antibody Technology," in Burdon et al., eds., *Laboratory Techniques in Biochemistry and Molecular Biology*, volume 13, Elsevier, publisher, Amsterdam (1984); Klein, *Immunology: The Science of Self-Nonself Discrimination*, John Wiley & Sons, publisher, New York (1982); and Kennett et al., eds., *Monoclonal Antibodies, Hybridoma: A New Dimension In Biological Analyses*, Plenum Press, publisher, New York (1980).

By "detecting" it is intended to include determining the presence or absence of a substance or quantifying the amount of a substance. The term thus refers to the use of the materials, compositions, and methods of the present invention for qualitative and quantitative determinations.

The isolation of other hybridomas secreting monoclonal antibodies of the same specificity as those described herein can be accomplished by the technique of anti-idiotypic screening (Potocmjak et al., *Science* 215:1637 (1982)). Briefly, an anti-idiotypic antibody is an antibody which recognizes unique determinants present on the antibody produced by the clone of interest. The anti-idiotypic antibody is prepared by immunizing an animal of the same strain used as the source of the monoclonal antibody with the monoclonal antibody of interest. The immunized animal will recognize and respond to the idiotypic determinants of the immunizing antibody by producing antibody to these idiotypic determinants (anti-idiotypic antibody).

For replication, the hybrid cells may be cultivated both in vitro and in vivo. High in vivo production makes this the presently preferred method of culture. Briefly, cells from the individual hybrid strains are injected intraperitoneally into pristane-primed BALB/c mice to produce ascites fluid containing high concentrations of the desired monoclonal antibodies. Monoclonal antibodies of isotype IgM or IgG may be purified from cultured supernatants using column chromatography methods well known to those of skill in the art.

Antibodies according to the present invention are particularly suited for use in immunoassays wherein they may be utilized in liquid phase or bound to a solid phase carrier. In addition, the antibodies in these immunoassays can be detectably labeled in various ways.

There are many different labels and methods of labeling known in the art. Examples of the types of labels which can be used in the present invention include, but are not limited to, enzymes, radioisotopes, fluorescent compounds, chemiluminescent compounds, bioluminescent compounds, and metal chelates. Those of ordinary skill in the art will know of other suitable labels for binding to antibodies, or will be able to ascertain the same by the use of routine experimentation. Furthermore, the binding of these labels to antibodies can be accomplished using standard techniques commonly known to those of ordinary skill in the art.

One of the ways in which antibodies according to the present invention can be detectably labeled is by linking the antibody to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label antibodies include malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase, and acetylcholine esterase.

The presence of detectably labeled antibodies also can be detected by labeling the antibodies with a radioactive isotope which then can be determined by such means as the use of a gamma counter or a scintillation counter. Isotopes which are particularly useful for the purpose of the present invention are $^3$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se.

It is also possible to detect the binding of detectably labeled antibodies by labeling the antibodies with a fluorescent compound. When a fluorescently labeled antibody is exposed to light of the proper wavelength, its presence then can be detected due to the fluorescence of the dye. Among the most commonly used fluorescent labeling compounds are fluorescein, isothiocyanate, rhodamine, phycoerythrin, phycocyanin, allophycocyanin, o-phthaldehyde, and fluorescamine.

The antibodies of the invention also can be detectably labeled using fluorescent emitting metals such as $^{152}$Eu, or others of the lanthanide series. These metals can be attached to the antibody molecule using such metal chelating groups as diethyl-enteriaminepentaacetic acid (DTPA) or ethylenediaminetetraacetic acid (EDTA).

Antibodies also can be detectably labeled by coupling them to a chemiluminescent compound. The presence of the chemiluminescent-tagged antibody is then determined by detecting the presence of luminescence that arises during the course of the chemical reaction. Examples of particularly useful chemiluminescent labeling compounds are luminal, isoluminol, theromatic acridinium ester, imidazole, acridinium salts, oxalate ester, and dioxetane.

Likewise, a bioluminescent compound may be used to label the antibodies according to the present invention. Bioluminescence is a type of chemiluminescence found in biological systems in which a catalytic protein increases the efficiency of the chemiluminescent reaction. The presence of a bioluminescent antibody is determined by detecting the presence of luminescence. Important bioluminescent compounds for purposes of labeling include luciferin and luciferase aequorin.

The antibodies and substantially purified antigen of the present invention are ideally suited for the preparation of a kit. Such a kit may comprise a carrier means being compartmentalized to receive in close confinement therewith one or more container means such as vials, tubes, and the like, each of said container means comprising the separate elements of the assay to be used.

The types of assays which can be incorporated in kit form are many and include, for example, competitive and non-competitive assays. Typical examples of assays which can utilize the antibodies of the invention are radioimmunoassays (RIA), enzyme immunoassays (EIA), enzyme-linked immunosorbent assays (ELISA), and immunometric, or sandwich immunoassays.

By the term "immunometric assay" or "sandwich immunoassay," it is meant to include simultaneous sandwich, forward sandwich, and reverse sandwich immunoassays.

These terms are well understood by those skilled in the art. Those of skill will also appreciate that antibodies According to the present invention will be useful in other variations and forms of assays which are presently known or which may be developed in the future. These are intended to be included within the scope of the present invention.

In the preferred mode for performing the assays it is important that certain "blockers" be present in the incubation medium (usually added with the labeled soluble antibody). The "blockers" are added to assure that non-specific proteins, protease, or human antibodies to mouse immunoglobulins present in the experimental sample do not cross-link or destroy the antibodies on the solid phase support, or the radiolabeled indicator antibody, to yield false positive or false negative results. The selection of "blockers" therefore adds substantially to the specificity of the assays described in the present invention.

It has been found that a number of nonrelevant (i.e., nonspecific) antibodies of the same class or subclass (isotype) as those used in the assays (e.g., $IgG_1$, $IgG_{2a}$, IgM, etc.) can be used as "blockers." The concentration of the "blockers" (normally 1–100 µg/µl) is important, in order to maintain the proper sensitivity yet inhibit any unwanted interference by mutually occurring cross-reactive proteins in human serum. In addition, the buffer system containing the "blockers" needs to be optimized. Preferred buffers are those based on weak organic acids, such as imidazole, HEPPS, MOPS, TES, ADA, ACES, HEPES, PIPES, TRIS, and the like, at physiological pH ranges. Somewhat less preferred buffers are inorganic buffers such as phosphate, borate, or carbonate. Finally, known protease inhibitors are preferably added (normally at 0.01–10 µg/ml) to the buffer which contains the "blockers."

There are many solid phase immunoadsorbents which have been employed and which can be used in the present invention. Well known immunoadsorbents include glass, polystyrene, polypropylene, dextran, nylon, and other materials, in the form of tubes, beads, and microtiter plates formed from or coated with such materials, and the like. The immobilized antibodies can be either covalently or physically bound to the solid phase immunoadsorbent, by techniques such as covalent bonding via an amide or ester linkage, or by absorption. Those skilled in the art will know many other suitable solid phase immunoadsorbents and methods for immobilizing antibodies thereon, or will be able to ascertain such, using no more than routine experimentation.

For in vivo, in vitro, or in situ diagnosis, labels such as radionuclides may be bound to antibodies according to the present invention either directly or by using an intermediary functional group. An intermediary group which is often used to bind radioisotopes which exist as metallic cations to antibodies is diethylenetriaminepentaacetic acid (DTPA). Typical examples of metallic cations which are bound in this manner are: $^{99m}Tc$, $^{123}I$, $^{111}In$, $^{131}I$, $^{97}Ru$, $^{67}Cu$, $^{67}Ga$, and $^{68}Ga$. The antibodies of the invention can also be labeled with non-radioactive isotopes for purposes of diagnosis. Elements which are particularly useful in this manner are $^{157}Gd$, $^{55}Mn$, $^{162}Dy$, $^{52}Cr$, and $^{56}Fe$.

The antigen of the invention may be isolated in substantially pure form employing antibodies according to the present invention. Thus, an embodiment of the present invention provides for substantially pure T cell receptor, B cell receptor, or Fc receptor chimera, said antigen characterized in that it is recognized by and binds to antibodies according to the present invention. In another embodiment, the present invention provides a method of isolating or purifying the receptor chimeric antigen, by forming a complex of said antigen with one or more antibodies directed against the receptor chimera.

The substantially pure T cell receptor, B cell receptor, or Fc receptor chimera antigens of the present invention may in turn be used to detect or measure antibody to the chimera in a sample, such as serum or urine. Thus, one embodiment of the present invention comprises a method of detecting the presence or amount of antibody to T cell receptor, B cell receptor, or Fc receptor chimera antigen in a sample, comprising contacting a sample containing an antibody to the chimeric antigen with detectably labeled receptor chimera, and detecting said label. It will be appreciated that immunoreactive fractions and immunoreactive analogues of the chimera also may be used. By the term "immunoreactive fraction" is intended any portion of the chimeric antigen which demonstrates an equivalent immune response to an antibody directed against the receptor chimera. By the term "immunoreactive analogue" is intended a protein which differs from the receptor chimera protein by one or more amino acids, but which demonstrates an equivalent immunoresponse to an antibody of the invention.

By "specifically recognizes and binds" is meant that the antibody recognizes and binds the chimeric receptor polypeptide but does not substantially recognize and bind other unrelated moleucles in a sample, e.g., a biological sample.

By "autoimmune-generated cell" is meant cells producing antibodies that react with host tissue or immune effector T cells that are autoreactive; such cells include antibodies against acetylcholine receptors (leading, e.g., to myasthenia gravis) or anti-DNA, anti-erythrocyte, and anti-placelet autoantibodies (leading, e.g., to lupus erythematosus).

By "therapeutic cell" is meant a cell which has been transformed by a chimera of the invention so that it is capable of recognizing and destroying a specific infective agent, a cell infected by a specific agent, a tumor or cancerous cell, or an autoimmune-generated cell; preferably such therapeutic cells are cells of the hematopoietic system.

By a "target infective agent" is meant any infective agent (e.g., a virus, bacterium, protozoan, or fungus) which can be recognized by a chimeric receptor-bearing therapeutic cell. By a "target cell" is meant any host cell which can be recognized by a chimeric receptor-bearing therapeutic cell; target cells include, without limitation, host cells which are infected with a virus, bacterium, protozoan, or fungus as well as tumor or cancerous cells and autoimmune-generated cells.

By "extracellular" is meant having at least a portion of the molecule exposed at the cell surface. By "intracellular" is meant having at least a portion of the molecule exposed to the therapeutic cell's cytoplasm. By "transmembrane" is meant having at least a portion of the molecule spanning the plasma membrane. An "extracellular portion," an "intracellular portion," and a "transmembrane portion," as used herein, may include flanking amino acid sequences which extend into adjoining cellular compartments.

By "oligomerize" is meant to complex with other proteins to form dimers, trimers, tetramers, or other higher order oligomers. Such oligomers may be homo-oligomers or hetero-oligomers. An "oligomerizing portion" is that region of a molecule which directs complex (i.e., oligomer) formation.

By "cytolytic" is meant to be capable of destroying a cell (e.g., a cell infected with a pathogen, a tumor or cancerous cell, or an autoimmune-generated) cell or to be capable of destroying an infective agent (e.g., a virus).

By "immunodeficiency virus" is meant a retrovirus that, in wild-type form, is capable of infecting T4 cells of a primate host and possesses a viral morphogenesis and morphology characteristic of the lentivirus subfamily. The term includes, without limitation, all variants of HIV and SIV, including HIV-1, HIV-2, SIVmac, SIVagm, SIVmnd, SIVsmm, SIVman, SIVmand, and SIVcpz.

By "MHC-independent" is meant that the cellular cytolytic response does not require the presence of an MHC class II antigen on the surface of the targeted cell.

By a "functional cytolytic signal-transducing derivative" is meant a functional derivative (as defined above) which is capable of directing at least 10%, preferably 40%, more preferably 70%, or most preferably at least 90% of the biological activity of the wild type molecule. As used herein, a "functional cytolytic signal-transducing derivative" may act by directly signaling the therapeutic cell to destroy a receptor-bound agent or cell (e.g., in the case of an intracellular chimeric receptor portion) or may act indirectly by promoting oligomerization with cytolytic signal transducing proteins of the therapeutic cell (e.g., in the case of a transmembrane domain). Such derivatives may be tested for efficacy, e.g., using the in vitro assays described herein.

By a "functional HIV envelope-binding derivative" is meant a functional derivative (as defined above) which is capable of binding any HIV envelope protein. Functional derivatives may be identified using, e.g., the in vitro assays described herein.

Therapeutic Administration

The transformed cells of the present invention may be used for the therapy of a number of diseases. Current methods of administering such transformed cells involve adoptive immunotherapy or cell-transfer therapy. These methods allow the return of the transformed immune-system cells to the bloodstream. Rosenberg, *Sci. Am.* 62 (May 1990); Rosenberg et al., *New Engl. J. Med.* 323:570 (1990).

The pharmaceutical compositions of the invention may be administered to any animal which may experience the beneficial effects of the compounds of the invention. Foremost among such animals are humans, although the invention is not intended to be so limited.

DETAILED DESCRIPTION

The drawings will first be described.

BRIEF DESCRIPTION OF THE DRAWINGS

FIGS. 4A–D shows increased intracellular free calcium ion follows crosslinking of mutant ζ chimeras in a T cell line. Jurkat E6 cells (Weiss et al., *J. Immunol.* 133:123–128 (1984)) were infected with recombinant vaccinia viruses and analyzed by flow cytometry. The results shown are for the gated $CD4^+$ population, so that only cells expressing the relevant chimeric protein are analyzed. The mean ratio of violet to blue Indo-1 fluorescence reflects the intracellular free calcium concentration in the population as a whole and the percentage of responding cells reflects the fraction of cells which exceed a predetermined threshold ratio (set so that 10% of untreated cells are positive). FIG. 4A and FIG. 4B show Jurkat cells expressing CD4:ζ (solid line) or CD16:ζ (dashed line) which were exposed to anti-CD4 MAb Leu3a (phycoerythrin conjugate), followed by crosslinking with goat antibody to mouse IgG. The dotted line shows the response of uninfected cells to anti-CD3 MAb OKT3. FIGS. 4C and 4D show Jurkat cells expressing CD4:ζD15G (solid line); CD4:ζC11G/D15G (dashes); or CD4:ζC11G (dots) which were treated and analyzed as in FIGS. 4A and 4B.

FIG. 5A: solid circles, CTL expressing CD4:ζ incubated with HeLa cells expressing gp120/41; open circles, CTL expressing CD4:ζ incubated with uninfected HeLa cells; solid squares, uninfected CTL incubated with HeLa cells expressing gp120/41; open squares, uninfected CTL incubated with uninfected HeLa cells. FIG. 5B: solid circles, CTL expressing CD4:η incubated with HeLa cells expressing gp120/41; open circles, CTL expressing CD4:γ incubated with HeLa cells expressing gp120/41; open squares, CTL expressing the C11G/D15G double mutant CD4:ζ chimera incubated with HeLa cells expressing gp120/41. FIG. 5C: Flow cytometric analysis of CD4 expression by the CTL used in FIG. 5B. To correct the target to effector ratios the percent of cells expressing CD4 chimera was determined by subtracting the scaled negative (uninfected) population by histogram superposition; for comparative purposes in this figure the uninfected cells were assigned an arbitrary threshold which gives roughly the same fraction positive for the other cell populations as would histogram subtraction.

FIG. 6A: solid circles, CTL expressing CD4:ζ incubated with HeLa cells expressing $CD16_{PI}$; open circles, CTL expressing CD4 incubated with HeLa cells expressing gp120; solid squares, CTL expressing CD16:ζ incubated with HeLa cells expressing gp120/41; open squares, CTL expressing $CD16_{PI}$ incubated with HeLa cells expressing gp120/41. FIG. 6B: solid circles, CTL expressing CD4:ζ incubated with Raji (MHC class II⁺) cells; open circles, uninfected CTL cells incubated with RJ2.2.5 (MHC class II⁻ Raji mutant) cells; solid squares, uninfected CTL incubated with Raji (MHC class II⁺) cells; open squares, CTL expressing CD4:ζ incubated with RJ2.2.5 (MHC class II⁻) cells. The ordinate scale is expanded.

FIG. 7A is a schematic diagram of the CD16:ζ fusion protein. The extracellular portion of the phosphatidylinositol-linked form of monomeric CD16 was joined to dimeric ζ just external to the transmembrane domain. The protein sequence at the fusion junction is shown at the bottom (SEQ ID NO:32 and 33). FIG. 7B shows a flow cytometric analysis of calcium mobilization following crosslinking of the CD16:ζ chimera in either a TCR positive or TCR negative cell line. The mean ratio of violet to blue fluorescence (a measure of relative calcium ion concentration) among cell populations treated with antibodies at time 0 is shown. Solid squares, the response of Jurkat cells to anti-CD3 MAb OKT3; solid triangles, the response of CD16:ζ to anti-CD16 MAb 3G8 crosslinking in the REX33A TCR⁻ mutant; open squares, the response to CD16:ζ crosslinking in the Jurkat TCR⁻ mutant line JRT3.T3.5; open triangles, the response to CD16:ζ crosslinking in Jurkat cells; crosses, the response to nonchimeric CD16 in Jurkat cells; and dots, the response to nonchimeric CD16 in the REX33A TCR⁻ cell line.

FIG. 8A shows the locations of the ζ deletion endpoints. Here as elsewhere mutations in ζ are represented by the original residue-location-mutant residue convention, so that D66*, for example, denotes replacement of Asp-66 by a termination codon (SEQ ID NO:34). FIG. 8B shows cytolysis assay results of undeleted CD16:ζ and salient ζ deletions. Hybridoma cells expressing surface antibody to CD16 were loaded with ⁵¹Cr and incubated with increasing numbers of human cytolytic lymphocytes (CTL) infected with vaccinia recombinants expressing CD16:ζ chimeras. The percent of ⁵¹Cr released is plotted as a function of the effector (CTL to target (hybridoma) cell ratio (e/t). Solid circles, cytolysis mediated by cells expressing CD16:ζ (mfi 18.7); solid squares, cytolysis mediated by cells expressing CD16:ζAsp66* (mfi 940.2); open squares, cytolysis mediated by cells expressing CD16:ζGlu60* (mfi 16.0); open circles, cytolysis mediated by cells expressing CD16:ζTyr51* (mfi 17.4); solid triangles, cytolysis mediated by cells expressing CD16:ζPhe34* (mfi 17.8); and open triangles, cytolysis mediated by cells expressing nonchimeric CD16 (mfi 591). Although in this experiment the expression of CD16:ζAsp66* was not matched to that of the other fusion proteins, cytolysis by cells expressing CD16:ζ at equivalent levels in the same experiment gave results essentially identical to those shown by cells expressing CD16:ζAsp66.

FIG. 9A is a schematic diagram of the monomeric bipartite and tripartite chimeras. At the top is the CD16:ζ construct truncated at residue 65 and lacking transmembrane Cys and Asp residues. Below are the CD16:CD5:ζ and CD16:CD7:ζ constructs and related controls. The peptide sequences of the intracellular domains are shown below (SEQ ID NO:34, 36, and 37). FIG. 9B shows the cytolytic activity of monomeric chimera deletion mutants. The cytolytic activity of cells expressing CD16:ζ (solid circles; mfi 495) was compared to that of cells expressing CD16:ζAsp66* (solid squares; mfi 527) or the mutants CD16:ζCys11Gly/Asp15Gly/Asp66*, (open squares, mfi 338) and CD16:ζCys11Gly/Asp15Gly/Glu60* (filled triangles; mfi 259). FIG. 9C shows the cytolytic activity mediated by tripartite fusion proteins. Solid triangles, CD16:ζAsp66*; open squares, CD16:5:ζ(48–65); solid squares CD16:7:ζ(48–65); open triangles, CD16:7:ζ(48–59); open circles, CD16:5; solid circles, CD16:7. FIG. 9D shows calcium mobilization by mutant and tripartite chimeras in the TCR negative Jurkat JRT3.T3.5 mutant cell line. Open circles, response of cells expressing dimeric CD16:ζAsp66*; solid squares, response of cells expressing CD16:ζCys11Gly/Asp15Gly/Asp66*; open squares, response of cells expressing CD16:ζCys11Gly/Asp15Gly/Glu60*; solid triangles, response of cells expressing CD16:7:ζ(48–65); and open triangles, response of cells expressing CD16:ζ(48–59).

FIGS. 10A and 10B show cytolytic activity and FIG. 10C shows calcium ion mobilization mediated by chimeras bearing point mutations near the carboxyl terminal tyrosine (Y62). FIGS. 10A and 10B represent data collected on cells expressing low and high amounts, respectively, of the CD16:ζ fusion proteins. Identical symbols are used for the calcium mobilization and cytolysis assays, and are shown in one letter code at right. Solid circles, cells expressing CD16:ζ (mfi in A, 21; B, 376); solid squares, cells expressing CD16:7:ζ(48–65) (mfi A, 31; B, 82); open squares, CD16:7:ζ(48–65)Glu60Gln (mfi A, 33; B, 92), crosses, CD16:7:ζ(48–65)Asp63Asn (mfi A, 30; B, 74); solid triangles, CD16:7:ζ(48–65)Tyr62Phe (mfi A, 24; B, 88); open circles, CD16:7:ζ(48–65)Glu61Gln (mfi A, 20; B, 62); and open triangles, CD16:7:ζ(48–65)Tyr62Ser (mfi B, 64). FIGS. 10D and 10E show cytolytic activity and FIG. 10F shows calcium ion mobilization by chimeras bearing point mutations near the amino terminal tyrosine (Y51). Identical symbols are used for the calcium mobilization and cytolysis assays and are shown at right. Solid circles, cells expressing CD16:ζ (mfi in D, 21.2; in E, 672); solid squares, cells expressing CD16:7:ζ(48–65) (mfi D, 31.3; E, 179); solid triangles, CD16:7:ζ(48–65)Asn48Ser (mfi D, 22.4; E, 209); open squares, CD16:7:ζ(48–65)Leu50Ser (mfi D, 25.0; E, 142); and open triangles, CD16:7:ζ(48–65)Tyr51Phe (mfi D, 32.3; E, 294).

FIG. 11A is a schematic diagram of chimeras formed by dividing the ζ intracellular domain into thirds and appending them to the transmembrane domain of a CD16:7 chimera. The sequences of the intracellular domains are shown below, with shared residues boxed, and related residues denoted by asterisks (SEQ ID NO:38, 39, and 40). FIG. 11B shows the cytolytic potency of the three ζ subdomains. Solid circles, cells expressing CD16:ζ(mfi 476); solid squares, CD16:7:ζ(33–65) (mfi 68); open squares, CD16:7:ζ(71–104) (mfi 114); and solid triangles, CD16:7:ζ(104–138) (mfi 104).

FIG. 13A shows the ratio of violet to blue fluorescence emitted by cells loaded with the calcium sensitive fluorophore Indo-1 shown as a function of time following crosslinking of the CD16 extracellular domain with antibodies. FIG. 13B shows a similar analysis of the increase in ratio of violet to blue fluorescence of cells bearing CD4:FcRγII chimeras, following crosslinking with antibodies.

FIG. 14A shows the percent of ⁵¹Cr released from anti-CD16 hybridoma (target) cells when the cells are exposed to increasing numbers of cytotoxic T lymphocytes expressing CD16:FcRγII chimeras (effector cells). FIG. 14B shows a similar analysis of cytotoxicity mediated by CD4:FcRγII chimeras against target cells expressing HIV envelope glycoproteins.

FIG. 15A is a schematic diagram of the deletion constructs (SEQ ID NO:41). FIGS. 15B and 15C shows calcium mobilization and cytolysis by carboxyl-terminal deletion variants of CD16:FcRγII A. FIGS. 15D and 15E show calcium mobilization and cytolysis by tripartite chimeras bearing progressively less of the amino terminus of the intracellular tail of CD16:FcRγII A.

FIG. 16 (SEQ ID NO: 24) shows the amino acid sequence of the CD3 delta receptor protein; the boxed sequence represents a preferred cytolytic signal transducing portion.

FIG. 17 (SEQ ID NO: 25) shows the amino acid sequence of the T3 gamma receptor protein; the boxed sequence represents a preferred cytolytic signal transducing portion.

FIG. 18 (SEQ ID NO: 26) shows the amino acid sequence of the mb1 receptor protein; the boxed sequence represents a preferred cytolytic signal transducing portion.

FIG. 19 (SEQ ID NO: 27) shows the amino acid sequence of the B29 receptor protein; the boxed sequence represents a preferred cytolytic signal transducing portion.

EXAMPLE I

Construction of Human IgG1:Receptor Chimeras

Figures 1A, 1B:
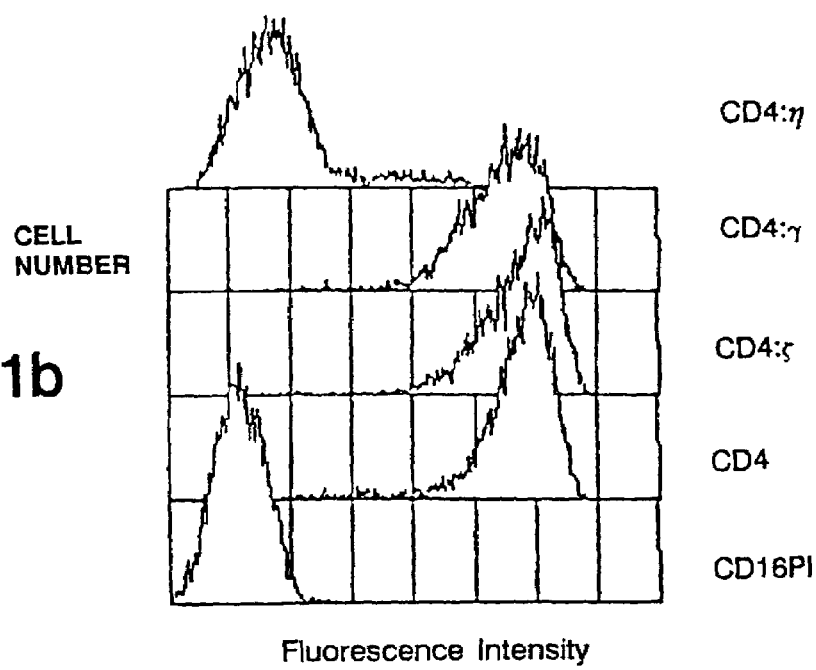
FIG. 1A presents the amino acid sequence about the site of fusion between CD4 (residues 1–369) and different receptor chains (SEQ ID NO:28, 29, 30, and 31). The underlined sequence shows the position of the amino acids encoded within the BamHI site used for fusion construction. The beginning of the transmembrane domain is marked with a vertical bar. The η sequence is identical to the ζ sequence at the amino terminus, but diverges at the carboxyl terminus (Jin et al., *Proc. Natl. Acad. Sci. USA* 87:3319–3323 (1990)).
FIG. 1B presents flow cytometric analysis of surface expression of CD4, CD4:ζ, CD4:γ and CD4:η in CV1 cells. Cells were infected with virus expressing CD4 chimeras or $CD16_{PI}$, incubated for 9 hours at 37° C., and stained with phycoerythrin-conjugated anti-CD4 MAb Leu3A.

Human IgG1 heavy chain sequences were prepared by joining sequences in the $C_H3$ domain to a cDNA fragment derived from the 3' end of the transmembrane form of the antibody mRNA. The 3' end fragment was obtained by polymerase chain reaction using a tonsil cDNA library as substrate, and oligonucleotides having the sequences:

CGC GGG GTG ACC GTG CCC TCC AGC AGC TTG GGC (SEQ ID NO: 7) and

CGC GGG GAT CCG TCG TCC AGA GCC CGT CCA GCT CCC CGT CCT GGG CCT CA (SEQ ID NO: 8), corresponding to the 5' and 3' ends of the desired DNA fragments respectively. The 5' oligo is complementary to a site in the $C_H1$ domain of human IgG1, and the 3' oligo is complementary to a site just 5' of the sequences encoding the membrane spanning domain. The PCR product was digested with BstXI and BamHI and ligated between BstXI and BamHI sites of a semisynthetic IgG1 antibody gene bearing variable and constant regions. Following the insertion of the BstXI to BamHI fragment, the amplified portions of the construct were replaced up to the SmaI site in $C_H3$ by restriction fragment interchange, so that only the portion between the SmaI site and the 3' oligo was derived from the PCR reaction.

To create a human IgG1:ζ chimeric receptor, the heavy chain gene ending in a BamHI site was joined to the BamHI site of the ζ chimera described below, so that the antibody sequences formed the extracellular portion. Flow cytometry of COS cells transfected with a plasmid encoding the chimera showed high level expression of antibody determinants when an expression plasmid encoding a light chain cDNA was cotransfected, and modest expression of antibody determinants when the light chain expression plasmid was absent.

Similar chimeras including human IgG1 fused to η or γ (see below), or any signal-transducing portion of a T cell receptor or Fc receptor protein may be constructed generally as described above using standard techniques of molecular biology.

To create a single transcription unit which would allow both heavy and light chains to be expressed from a single promoter, a plasmid encoding a bicistronic mRNA was created from heavy and light chain coding sequences, and the 5' untranslated portion of the mRNA encoding the 78 kD glucose regulated protein, otherwise known as grp78, or BiP. grp78 sequences were obtained by PCR of human genomic DNA using primers having the sequences:

CGC GGG CGG CCG CGA CGC CGG CCA AGA CAG CAC (SEQ ID NO: 9) and

CGC GTT GAC GAG CAG CCA GTT GGG CAG CAG CAG (SEQ ID NO: 10)

at the 5' and 3' ends respectively. Polymerase chain reactions with these oligos were performed in the presence of 10% dimethyl sulfoxide. The fragment obtained by PCR was digested with NotI and HincII and inserted between NotI and HpaI sites downstream from human IgG1 coding sequences. Sequences encoding a human IgG kappa light chain cDNA were then inserted downstream from the grp78 leader, using the HincII site and another site in the vector. The expression plasmid resulting from these manipulations consisted of the semisynthetic heavy chain gene, followed by the grp78 leader sequences, followed by the kappa light chain cDNA sequences, followed by polyadenylation signals derived from an SV40 DNA fragment. Transfection of COS cells with the expression plasmid gave markedly improved expression of heavy chain determinants, compared to transfection of plasmid encoding heavy chain determinants alone.

To create a bicistronic gene comprising a heavy chain/ receptor chimera and a light chain, the upstream heavy chain sequences can be replaced by any chimeric heavy chain/ receptor gene described herein.

EXAMPLE II

Construction of CD4 Receptor Chimeras

Human ζ (Weissman et al., *Proc. Natl. Acad. Sci. USA* 85:9709–9713 (1988b)) and γ (Küster et al., *J. Biol. Chem.* 265:6448–6452 (1990)) cDNAs were isolated by polymerase chain reaction from libraries prepared from the HPB-ALL tumor cell line (Aruffo et al., *Proc. Natl. Acad. Sci. USA* 84:8573–8577 (1987b)) and from human natural killer cells, while η cDNA (Jin et al., *Proc. Natl. Acad. Sci. USA* 87:3319–3323 (1990)) was isolated from a murine thymocyte library. ζ, η and γ cDNAs were joined to the extracellular domain of an engineered form of CD4 possessing a BamHI site just upstream of the membrane spanning domain (Aruffo et al., *Proc. Natl. Acad. Sci. USA* 84:8573–8577 (1987b); Zettlmeissl et al., *DNA Cell Biol.* 9347–353 (1990)) which was joined to the BamHI site naturally present in the ζ and η cDNAs at a similar location a few residues upstream of the membrane spanning domain (SEQ ID NOS: 1, 3, 4 and 6). To form the fusion protein with γ a BamHI site was engineered into the sequence at the same approximate location (FIG. 1; SEQ ID NO: 2 and 5). The gene fusions were introduced into a vaccinia virus expression plasmid bearing the *E. coli* gpt gene as a selectable marker, and inserted into the genome of the vaccinia WR strain by homologous recombination and selection for growth in mycophenolic acid (Falkner et al., *J. Virol.* 62:1849–1854 (1988); Boyle et al., *Gene* 65:123–128 (1988)). Flow cytometric analysis showed that the vaccinia recombinants direct the abundant production of CD4:ζ and CD4:γ fusion proteins at the cell surface, whereas the expression of CD4:η is substantially weaker (FIG. 1B). The latter finding is consistent with a recent report that transfection of an η cDNA expression plasmid into a murine hybridoma cell line gave substantially less expression than transfection of a comparable ζ expression plasmid (Clayton et al., *J. Exp. Med.* 172:1243–1253 (1990)). Immunoprecipitation of cells infected with the vaccinia recombinants revealed that the fusion proteins form covalent dimers, unlike the naturally occurring CD4 antigen. The molecular masses of the monomeric CD4:ζ and CD4:γ fusion proteins and native CD4 were found to be 63, 55 and 53 kD respectively. The larger masses of the fusion proteins are approximately consistent with the greater length of the intracellular portion, which exceeds that of native CD4 by 75 (CD4:ζ) or 5 (CD4:γ) residues.

EXAMPLE III

CD4 Chimeras Can Associate With Other Receptor Chains

Cell surface expression of the macrophage/natural killer cell form of human FcγRIII (CD16$_{TM}$) on transfectants is facilitated by cotransfection with murine (Kurosaki et al., *Nature* 342:805–807 (1989)) or human (Hibbs et al., *Science* 246:1608–1611 (1989)) γ, as well as by human ζ (Lanier et al., *Nature* 342:803–805 (1989)).

Figure 2:
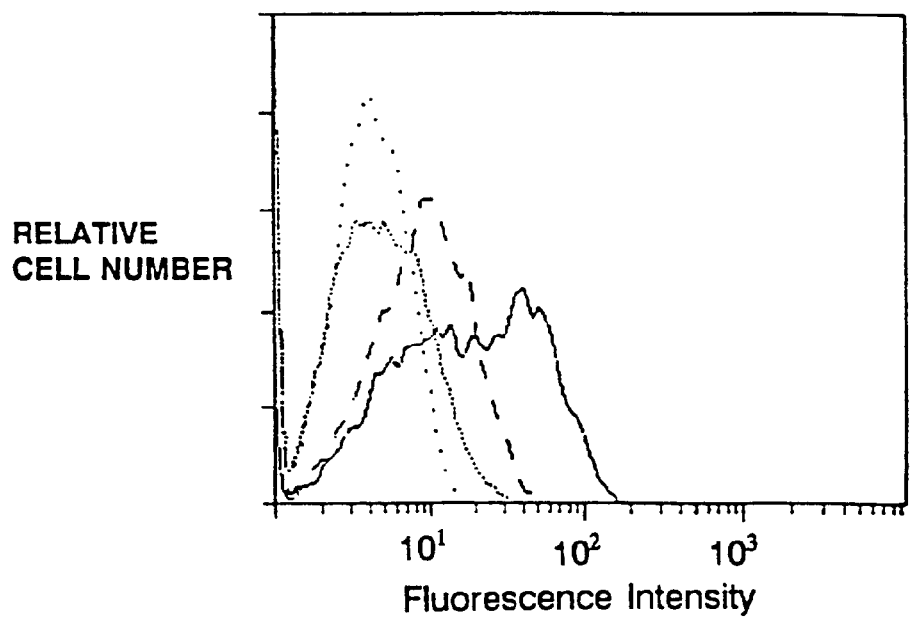
FIG. 2 shows surface expression of $CD16_{TM}$ following coinfection of $CD16_{TM}$ alone (dense dots), or coinfected with virus expressing CD4:γ (dashes) or CD4:ζ (solid line). Sparse dots, cells infected with CD4:ζ alone, stained with 3G8 (Fleit et al., *Proc. Natl. Acad. Sci. USA* 79:3275–3279 (1982)) (anti-CD16 MAb).

Consistent with these reports, expression of the chimeras also allowed surface expression of CD16$_{TM}$ when delivered to the target cell either by cotransfection or by coinfection with recombinant vaccinia viruses (FIG. 2). The promotion of CD16$_{TM}$ surface expression by ζ was more pronounced than promotion by γ (FIG. 2) in the cell lines examined, whereas native CD4 did not enhance CD16$_{TM}$ surface expression.

EXAMPLE IV

Asp ζ Mutants Do Not Coassociate with Fc Receptor

Figure 3:
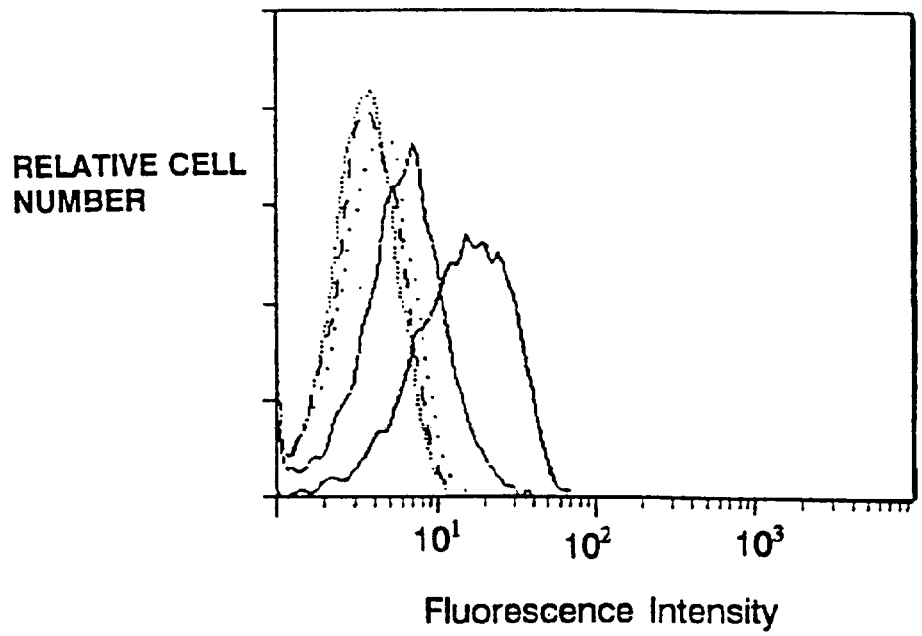
FIG. 3 shows surface expression of $CD16_{TM}$ following coinfection by viruses expressing $CD16_{TM}$ and the following ζ chimeras: CD4:ζ (thick line), CD4:ζ C11G (solid line); CD4:ζ (dashed line); CD4:ζ C11G/D15G (dense dots); no coinfection ($CD16_{TM}$ alone, sparse dots). Cells were incubated with anti-CD16 MAb 3G8 and phycoerythrin-conjugated $Fab'_2$ goat antibodies to mouse IgG. The level of expression of the ζ chimeras was essentially identical for the different mutants analyzed, and coinfection of cells with viruses expressing $CD16_{TM}$ and ζ chimeras did not appreciably alter surface expression of the chimeras.

To create chimeras which would not associate with existing antigen or Fc receptors, mutant ζ fusion proteins which lacked either the intramembranous Asp or intramembranous Cys residue or both were prepared. Flow cytometry showed that the intensity of cell surface expression by the different mutant chimeras was not appreciably different from the unmutated precursor, and immunoprecipitation experiments showed that total expression by the chimeras was similar. As expected, the mutant chimeras lacking the transmembrane cysteine residue were found not to form disulfide linked dimers. The two mutant chimeras lacking Asp were incapable of supporting the surface expression of CD16™, whereas the monomeric chimeras lacking Cys but bearing Asp allowed CD16$_{TM}$ to be coexpressed, but at lower efficiency than the parental dimer (FIG. 3).

EXAMPLE V

Mutant Receptors Retain the Ability to Initiate a Calcium Response

Figure 4C:
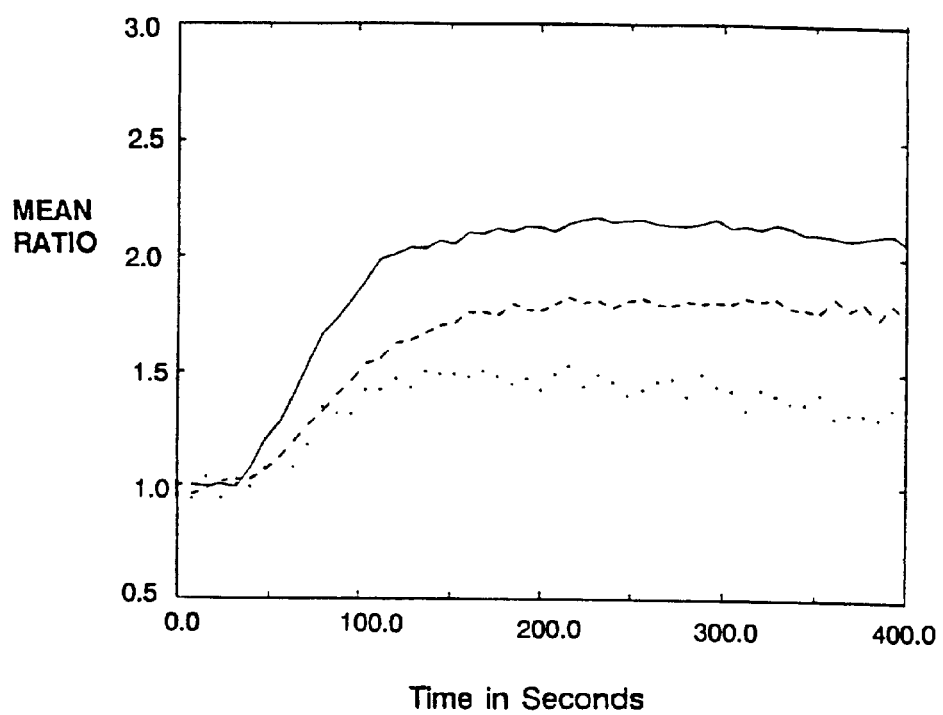
Figure 4D:
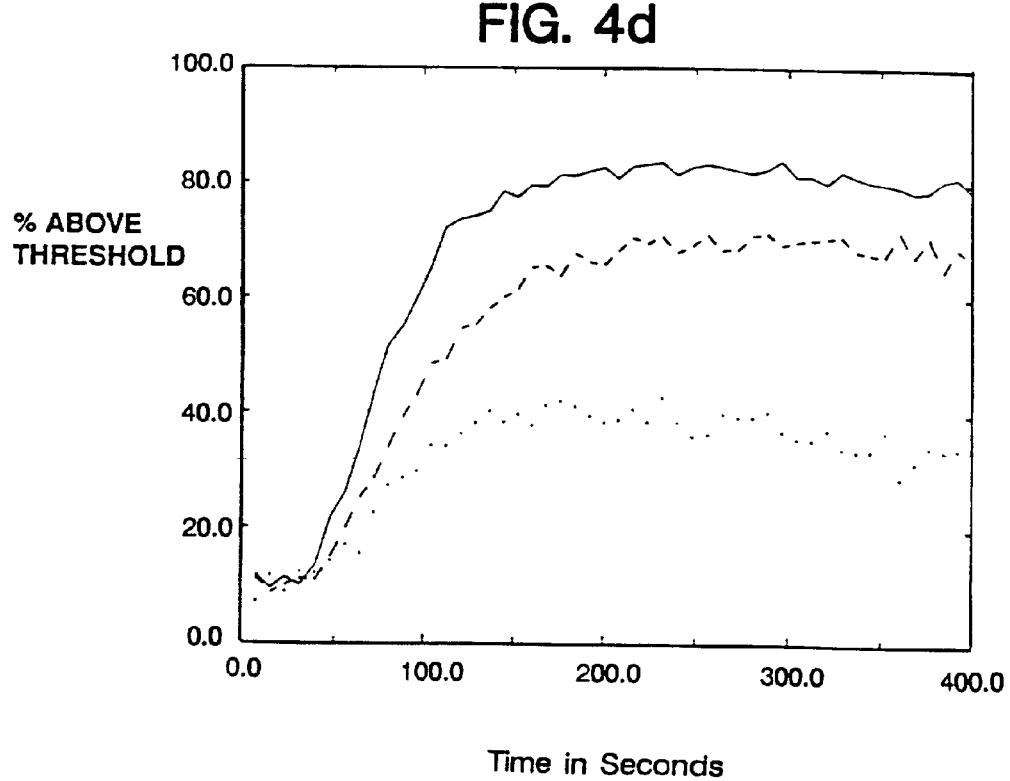

To determine whether crosslinking of the fusion proteins would allow the accumulation of free intracellular calcium in a manner similar to that known to occur with the T cell antigen receptor, cells of the human T cell leukemia line, Jurkat E6 (ATCC Accessior Number TIB 152, American Type Culture Collection, Rockville, Md.), were infected with the vaccinia recombinants and the relative cytoplasmic calcium concentration following crosslinking of the extracellular domain with antibodies was measured. Flow cytometric measurements were performed with cells loaded with the calcium sensitive dye Indo-1 (Grynkiewicz et al., *J. Biol. Chem.* 260:3340–3450 (1985); Rabinovitch et al., *J. Immunol.* 137:952–961 (1986)). FIGS. 4A–D shows the results of calcium flux experiments with cells infected with CD4:ζ and the Asp⁻ and Cys⁻ mutants of ζ. Crosslinking of the chimeras, reproducibly increased intracellular calcium. CD4:η and CD4:γ similarly allowed accumulation of intracellular calcium in infected cells. Jurkat cells express low levels of CD4 on the cell surface, however, crosslinking of the native CD4 in the presence or absence of CD16:ζ does not alter intracellular calcium levels (FIGS. 4A–B).

EXAMPLE VI

CD4:ζ, η, and γ Chimeras Mediate Cytolysis of Targets Expressing HIV gp120/41

Figure 5A:
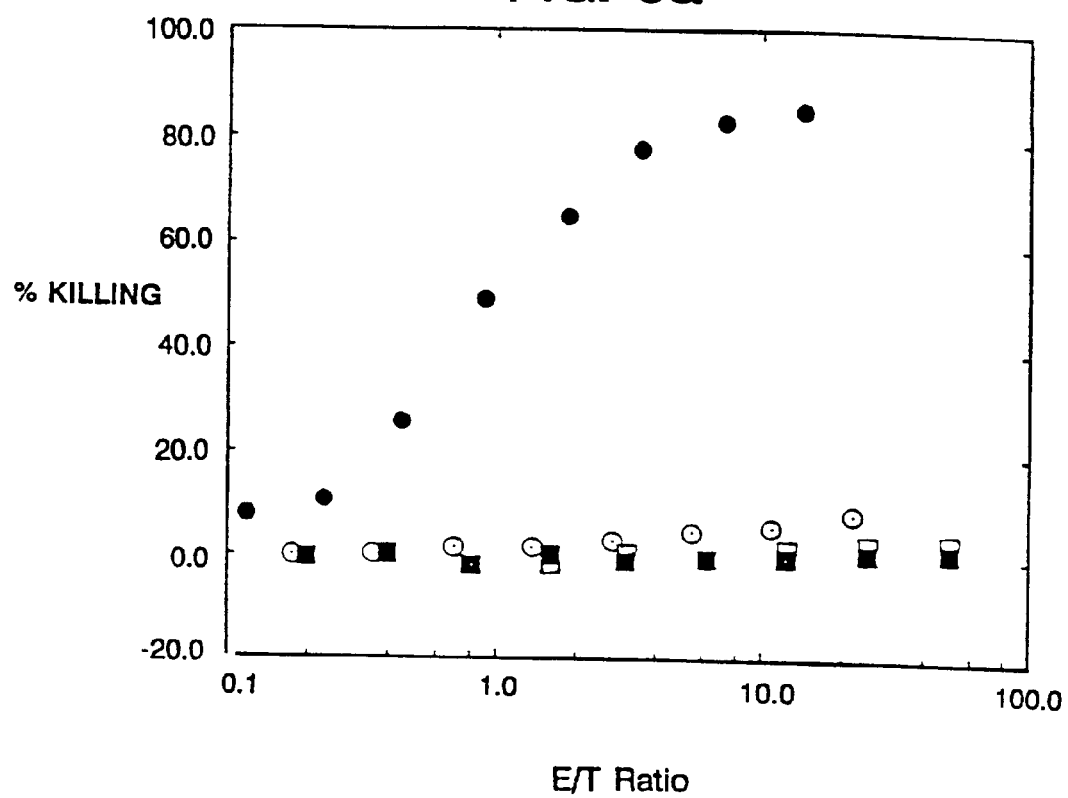
FIGS. 5A–C shows that CD4:ζ, CD4:η, and CD4:γ receptors allow cytolytic T lymphocytes (CTL) to kill targets expressing HIV-1 gp120/41.
Figure 5B:
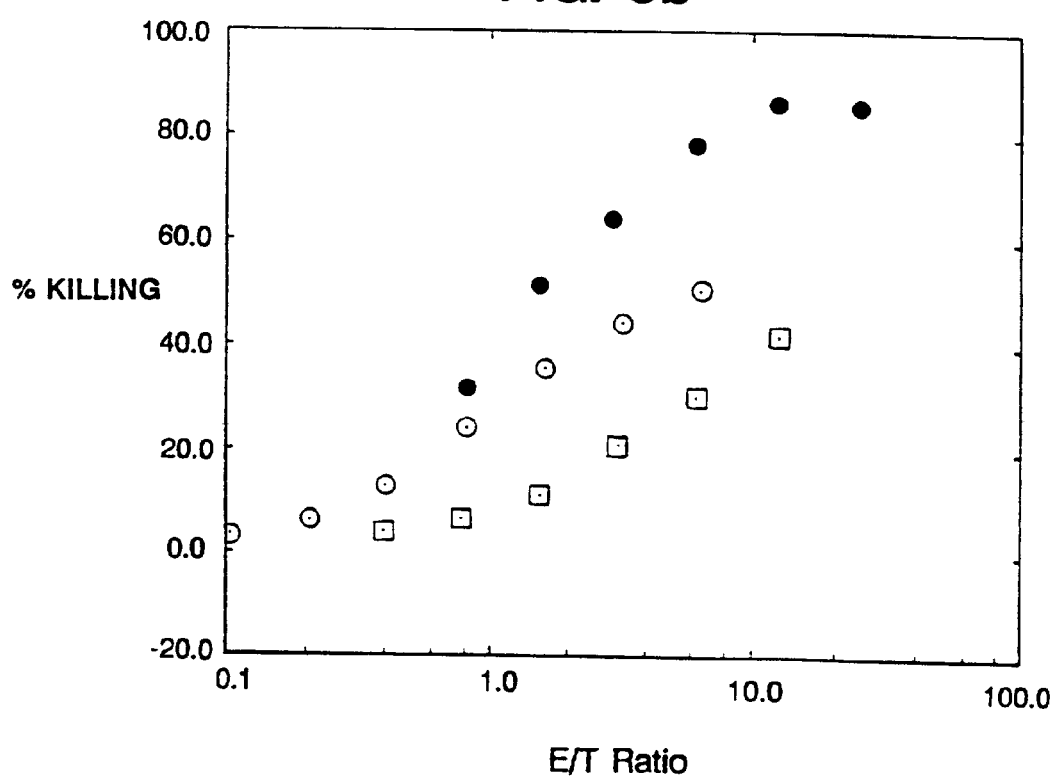
Figure 5C:
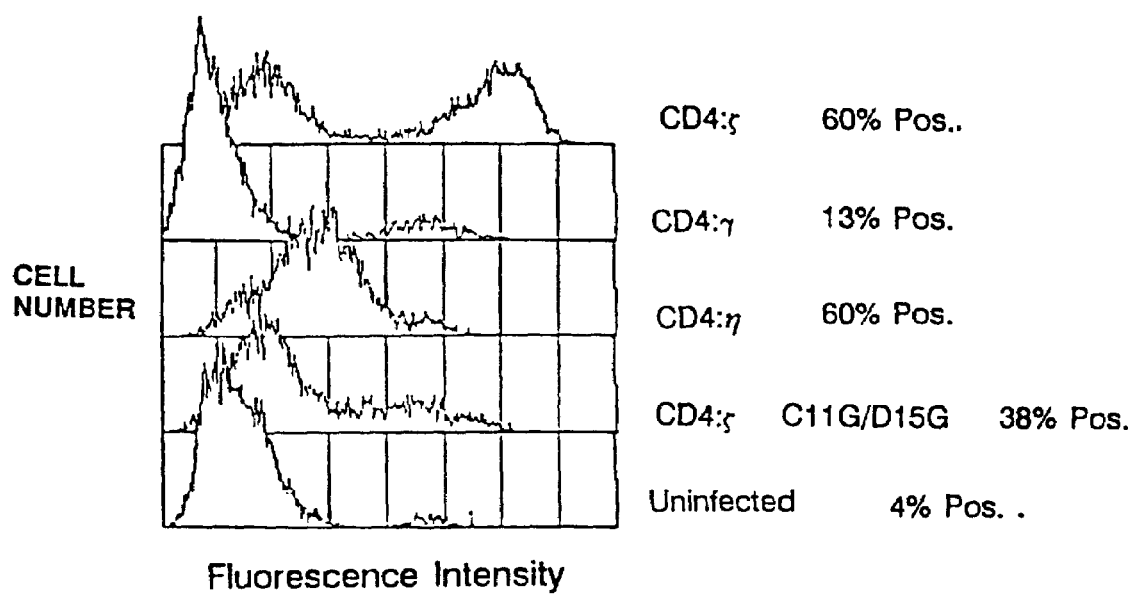

To determine whether the chimeric receptors would trigger cytolytic effector programs, a model target:effector system based on CD4 recognition of the HIV envelope gp120/gp41 complex was created. HeLa cells were infected with recombinant vaccinia viruses expressing gp120/gp41 (Chakrabarti et al., *Nature* 320:535–537 (1986); Earl et al., *J. Virol.* 64:2448–2451 (1990)) and labeled with $^{51}$Cr. The labeled cells were incubated with cells from a human allospecific (CD8⁺, CD4⁻) cytotoxic T lymphocyte line which had been infected with vaccinia recombinants expressing the CD4:ζ, CD4:η, or CD4:γ chimeras, or the CD4:ζCys11Gly:Asp15Gly double mutant chimera. FIGS. 5A–C shows that HeLa cells expressing gp120/41 were specifically lysed by cytotoxic T lymphocytes (CTL) expressing CD4 chimeras. Uninfected HeLa cells were not targeted by CTL armed with CD4:ζ chimeras, and HeLa cells expressing gp120/41 were not recognized by uninfected CTL. To compare the efficacy of the various chimeras, the effector to target ratios were corrected for the fraction of CTL expressing CD4 chimeras, and for the fraction of HeLa cells expressing gp120/41, as measured by flow cytometry. FIG. 5C shows a cytometric analysis of CD4 expression by the CTL used in the cytolysis experiment shown in FIGS. 5A and 5B. Although the mean density of surface CD4:ζ greatly exceeded the mean density of CD4:η, the cytolytic efficiencies of cells expressing either form were similar. Correcting for the fraction of targets expressing gp120, the efficiency of cytolysis mediated by CD4:ζ and CD4:η proteins are comparable to the best efficiencies reported for specific T cell receptor target:effector pairs (the mean effector to target ratio for 50% release by T cells expressing CD4:ζ was 1.9±0.99, n=10. The CD4:γ fusion was less active, as was the CD4:ζ fusion lacking the transmembrane Asp and Cys residues. However in both cases significant cytolysis was observed (FIGS. 5B–C).

Figure 6A:
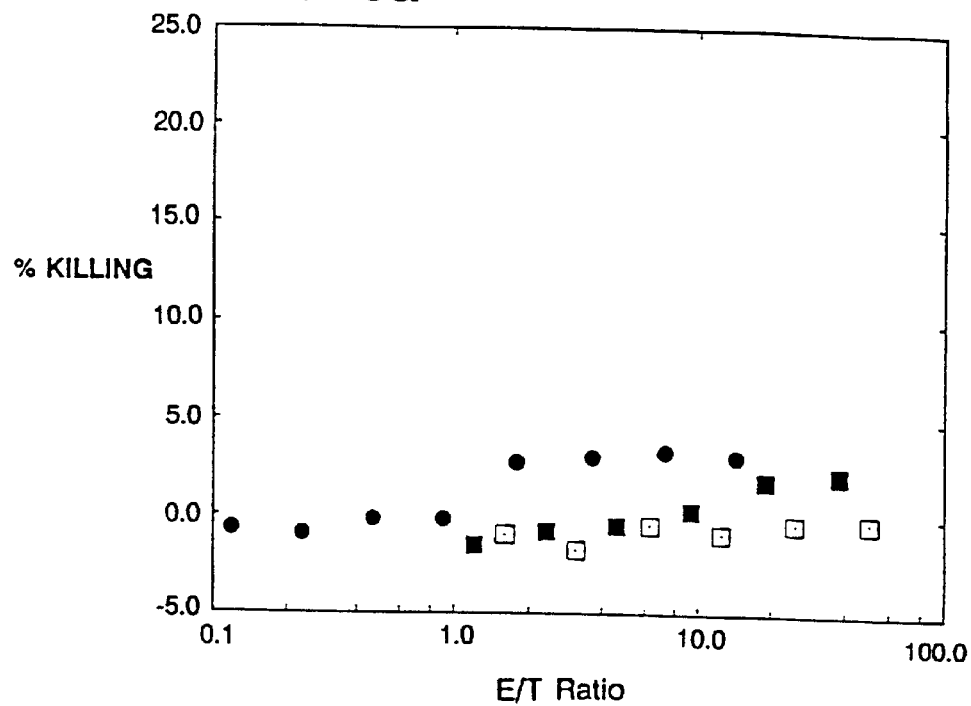
FIGS. 6A–B shows specificity of CD4-directed cytolysis.

To control for the possibility that vaccinia infection might promote artefactual recognition by CTL, similar cytolysis experiments were performed with target cells infected with vaccinia recombinants expressing the phosphatidylinositol linked form of CD16 (CD16$_{PI}$) and labeled with $^{51}$Cr, and with CTL infected with control recombinants expressing either CD16$_{PI}$ or CD16:ζ. FIG. 6A shows that T cells expressing non-CD4 chimeras do not recognize native HeLa cells or HeLa cells expressing gp120/41, and similarly that T cells expressing CD4 chimeras do not recognize HeLa cells expressing other vaccinia-encoded surface proteins. In addition, CTLs expressing non-chimeric CD4 do not significantly lyse HeLa cells expressing gp120/41 (FIG. 6A).

EXAMPLE VII

MHC Class II-Bearing Cells Are Not Targeted by the Chimeras

Figure 6B:
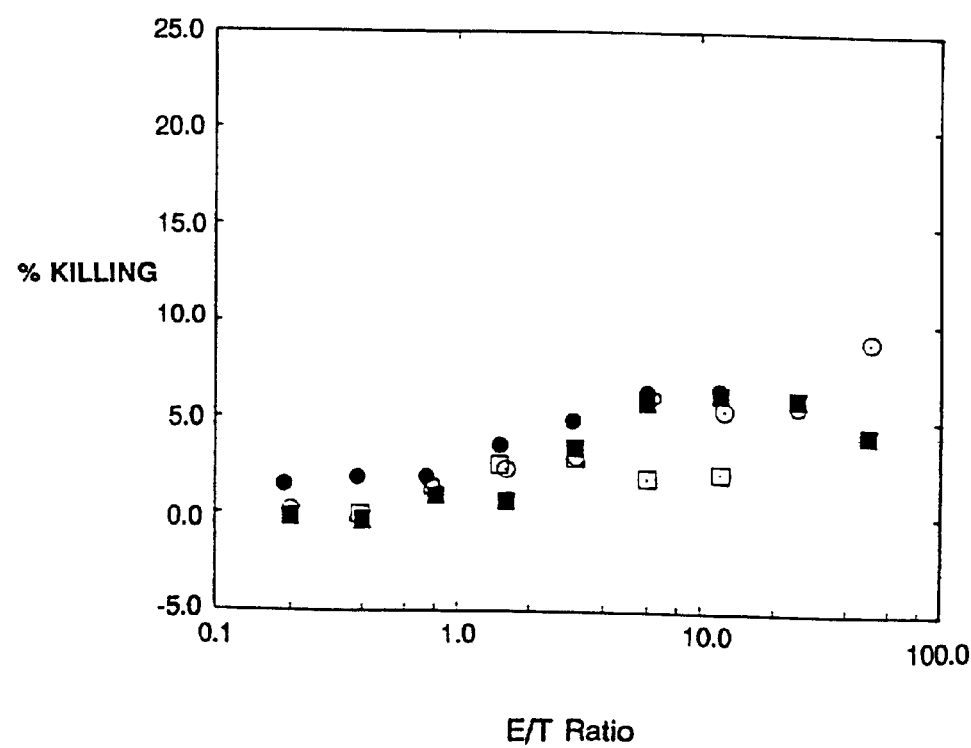

CD4 is thought to interact with a nonpolymorphic sequence expressed by MHC class II antigen (Gay et al., Nature 328:626–629 (1987); Sleckman et al., Nature 328:351–353 (1987)). Although a specific interaction between CD4 and class II antigen has never been documented with purified proteins, under certain conditions adhesion between cells expressing CD4 and cells expressing class II molecules can be demonstrated (Doyle et al., Nature 330:256–259 (1987); Clayton et al., J. Exp. Med. 172:1243–1253 (1990); Lamarre et al., Science 245:743–746 (1989)). Next examined was whether killing could be detected against cells bearing class II antigen. FIG. 6B shows that there is no specific cytolysis directed by CD4:ζ against the Raji B cell line, which expresses abundant class II antigen. Although a modest (≈5%) cytolysis is observed, a class II-negative mutant of Raji, RJ2.2.5, (Accolla, J. Exp. Med. 157:1053–1058 (1983)) shows a similar susceptibility, as do Raji cells incubated with uninfected T cells.

EXAMPLE VIII

Figure 7A:
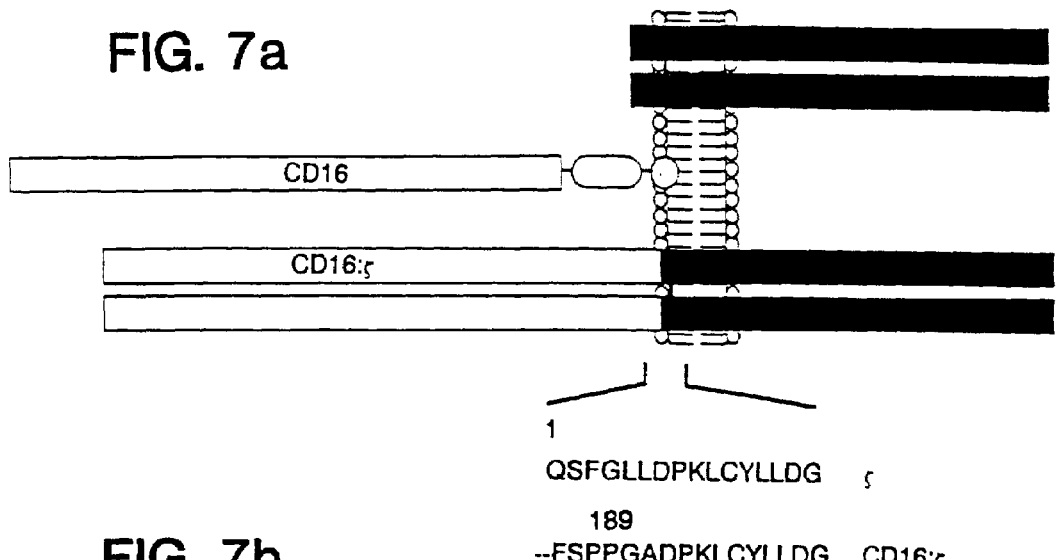
FIGS. 7A–B shows characterization of the CD16:ζ chimeric receptor.

Sequence Requirements for Induction of Cytolysis by the T Cell Antigen/Fc Receptor Zeta Chain Although chimeras between CD4 and ζ can arm cytotoxic T lymphocytes (CTL) to kill target cells expressing HIV gp120, an alternative to CD4 was sought in order to unambiguously compare the properties of zeta chimeras introduced into human T cell lines. Such lines can express CD4, making it difficult to specifically define the relationship between the type or degree of calcium mobilization and the cytotoxic potential of the different chimeras. To circumvent this, chimeras were created between ζ and CD16 in which the extracellular domain of CD16 is attached to the transmembrane and intracellular sequences of ζ (FIG. 7A). The gene fusions were introduced into a vaccinia virus expression plasmid bearing the E. coli gpt gene as a selectable marker and inserted into the genome of the vaccinia WR strain by homologous recombination and selection for growth in mycophenolic acid (Falkner and Moss, J. Virol. 62:1849 (1988); Boyle and Coupar, Gene 65:123 (1988)).

Figure 7B:
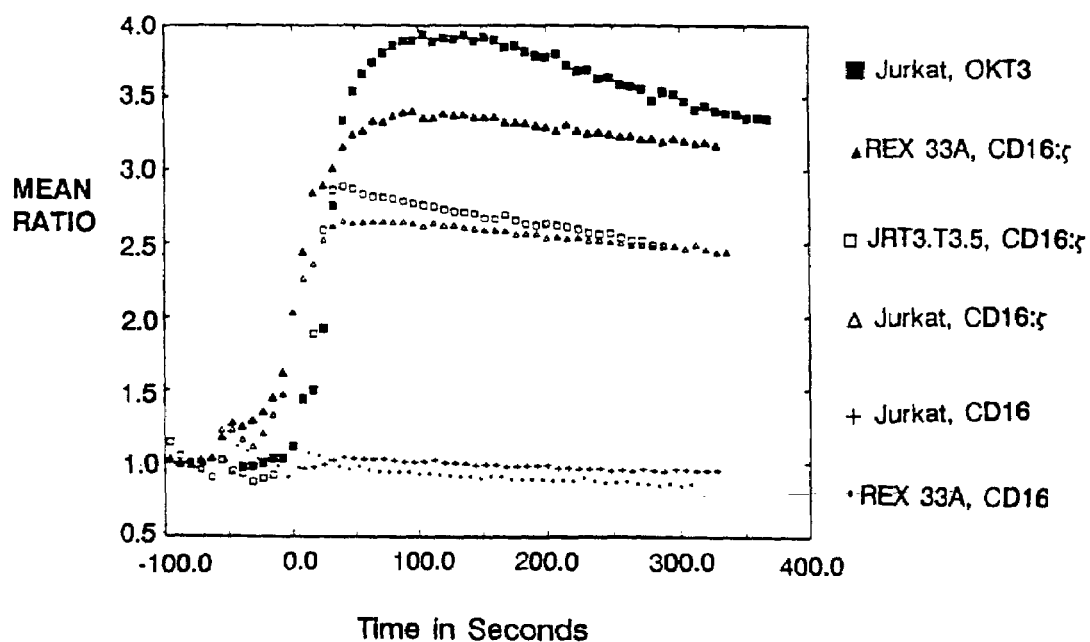

T cell lines were infected with the vaccinia recombinants and the relative cytoplasmic free calcium ion concentration was measured following crosslinking of the extracellular domains with antibodies. Both spectrofluorimetric (bulk population) and flow cytometric (single cell) measurements were performed with cells loaded with the dye Indo-1 (Grynkiewicz et al., J. Biol. Chem. 260:3440 (1985); Rabinovitch et al., J. Immunol. 137:952 (1986)). FIG. 7B shows an analysis of data collected from cells of the Jurkat human T cell leukemia line infected with vaccinia recombinants expressing CD16:ζ fusion protein. Crosslinking of the chimeras reproducibly increased intracellular calcium, while similar treatment of cells expressing nonchimeric CD16 had little or no effect. When the chimera was expressed in mutant cell lines lacking antigen receptor, either REX33A (Breitmeyer et al., J. Immunol. 138:726 (1987); Sancho et al., J. Biol. Chem 264:20760 (1989)) or Jurkat mutant JRT3.T3.5 (Weiss et al., J. Immunol. 135:123 (1984)), a strong response to CD16 antibody crosslinking was seen. Similar data have been collected on the REX20A (Breitmeyer et al., supra, 1987; Blumberg et al., J. Biol. Chem. 265:14036 (1990)) mutant cell line, and a CD3/Ti negative mutant of the Jurkat cell line established in this laboratory. Infection with recombinants expressing CD16:ζ did not restore the response to anti-CD3 antibody, showing that the fusion protein did not act by rescuing intracellular CD3 complex chains.

Figures 8A, 8B:
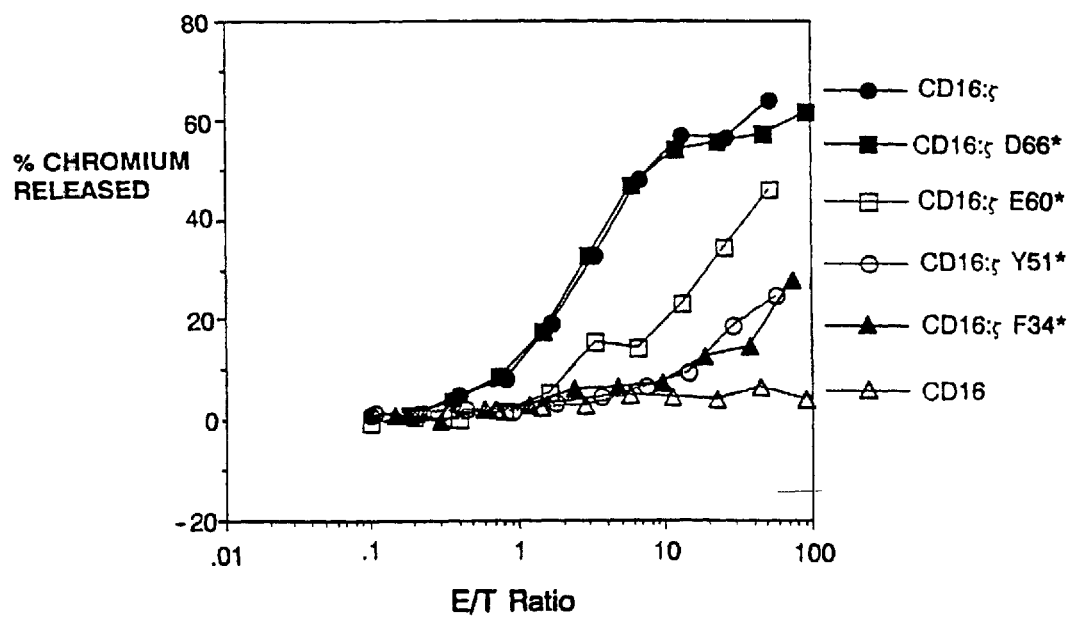
FIGS. 8A–B shows deletion analysis of cytolytic potential.

To evaluate the ability of the chimeras to redirect cell-mediated immunity, CTLs were infected with vaccinia recombinants expressing CD16 chimeras and used to specifically lyse hybridoma cells expressing membrane-bound anti-CD16 antibodies. This assay is an extension of a hybridoma cytotoxicity assay originally developed to analyze effector mechanisms of cells bearing Fc receptors (Graziano and Fanger, J. Immunol. 138:945, 1987; Graziano and Fanger, J. Immunol. 139:35–36, 1987; Shen et al., Mol. Immunol. 26:959, 1989; Fanger et al., Immunol. Today 10:92, 1989). FIG. 8B shows that expression of CD16:ζ in cytotoxic T lymphocytes allows the armed CTL to kill 3G8 (anti-CD16; Fleit et al., Proc. Natl. Acad. Sci. USA 79:3275, 1982) hybridoma cells, whereas CTL expressing the phosphatidylinositol-linked form of CD16 are inactive. CTL armed with CD16:ζ also do not kill hybridoma cells expressing an irrelevant antibody.

To identify the minimal ζ sequences necessary for cytolysis, a series of deletion mutants were prepared in which successively more of the ζ intracellular domain was removed from the carboxyl terminus (FIG. 8A). Most of the intracellular domain of zeta could be removed with little consequence for cytolytic potential; the full length chimera CD16:ζ was essentially equal in efficacy to the chimera deleted to residue 65, CD16:ζAsp66* (FIG. 8B). A substantial decrease in cytotoxicity was observed on deletion to ζ residue 59 (chimera CD16:ζGlu60*), and further deletion to residue 50 resulted in slightly less activity. However complete loss of activity was not observed even when the intracellular domain was reduced to a three residue transmembrane anchor (FIG. 8B).

Because ζ is a disulfide linked dimer, one explanation for the retention of cytolytic activity was that endogenous ζ was forming heterodimers with the chimeric ζ deletion, thereby reconstituting activity. To test this idea, ζ residues 11 and 15 were changed from Asp and Cys respectively to Gly (Cys11Gly/Asp15Gly), and immunoprecipitations were carried out as follows. Approximately $2\times10^6$ CV1 cells were infected for one hour in serum free DME medium with recombinant vaccinia at a multiplicity of infection (moi) of at least ten. Six to eight hours post-infection, the cells were detached from the plates with PBS/1 mM EDTA and surface labeled with 0.2 mCi $^{125}$I per $2\times10^6$ cells using lactoperoxidase and $H_2O_2$ by the method of Clark and Einfeld (Leukocyte Typing II, pp 155–167, Springer-Verlag, NY, 1986). The labeled cells were collected by centrifugation and lysed in 1% NP-40, 0.1% SDS, 0.15 M NaCl, 0.05 M Tris, pH 8.0, 5mM $MgCl_2$, 5 mM KCl, 0.2 M iodoacetamide and 1 mM PMSF. Nuclei were removed by centrifugation, and CD16 proteins were immunoprecipitated with antibody 3G8 (Fleit et al., supra, 1982; Medarex) and anti-mouse IgG agarose (Cappel, Durham, N.C.). Samples were electrophoresed through an 8% polyacrylamide/SDS gel under non-reducing conditions or through a 10% gel under reducing conditions.

These immunoprecipitations confirmed that the CD16:ζCys11Gly/Asp15Gly chimera did not associate in disulfide-linked dimer structures.

The cytolytic activity of the mutant receptors was also tested. The mutated chimera deleted to residue 65 (CD16:ζCys11Gly/Asp15Gly/Asp66*) was, depending on the conditions of assay, two to eight fold less active in the cytolysis assay than the comparable unmutated chimera (CD16:ζAsp66*), which was usually within a factor of two of, or indistinguishable in activity from, CD16:ζ (FIG. 9B). The reduction in activity of the mutant chimeras is comparable to the reduction seen with CD4 chimeras of similar structure (see above) and is most likely attributable to the lower efficiency of ζ monomers compared to dimers. In contrast, the Asp⁻, Cys⁻ mutated chimera deleted to residue 59 had no cytolytic activity (FIG. 9B), supporting the hypothesis that association with other chains mediated by the transmembrane Cys and/or Asp residues was responsible for the weak persistence of cytolytic activity in deletions more amino terminal than residue 65.

Figure 9A:
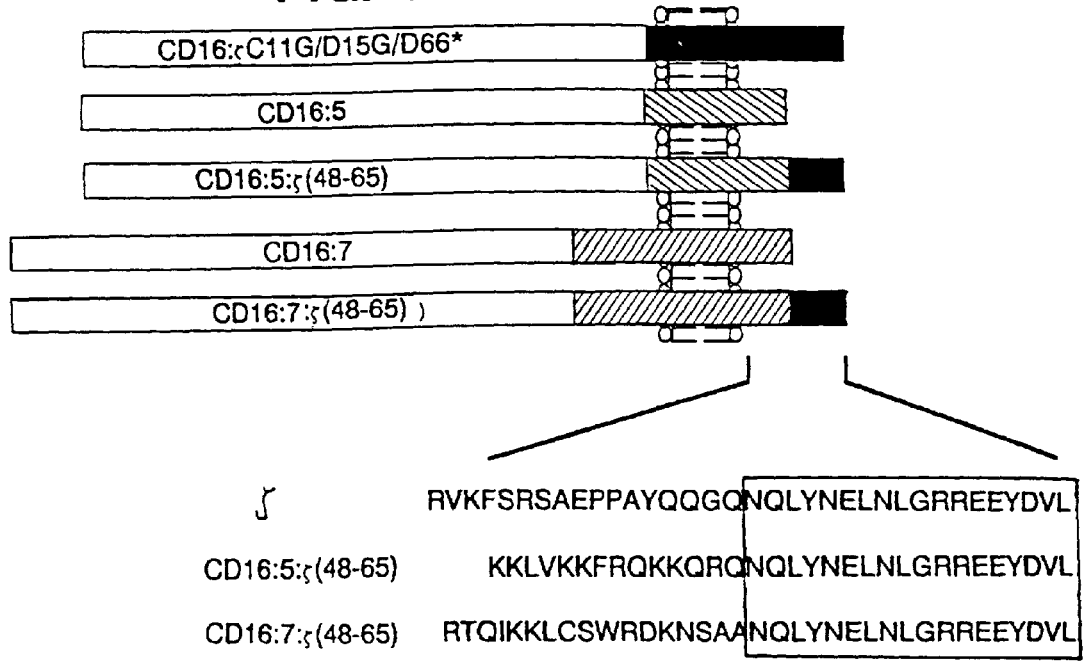
FIGS. 9A–D shows that elimination of the potential for transmembrane interactions reveals a short ζ segment capable of mediating cytolysis.
Figure 9B:
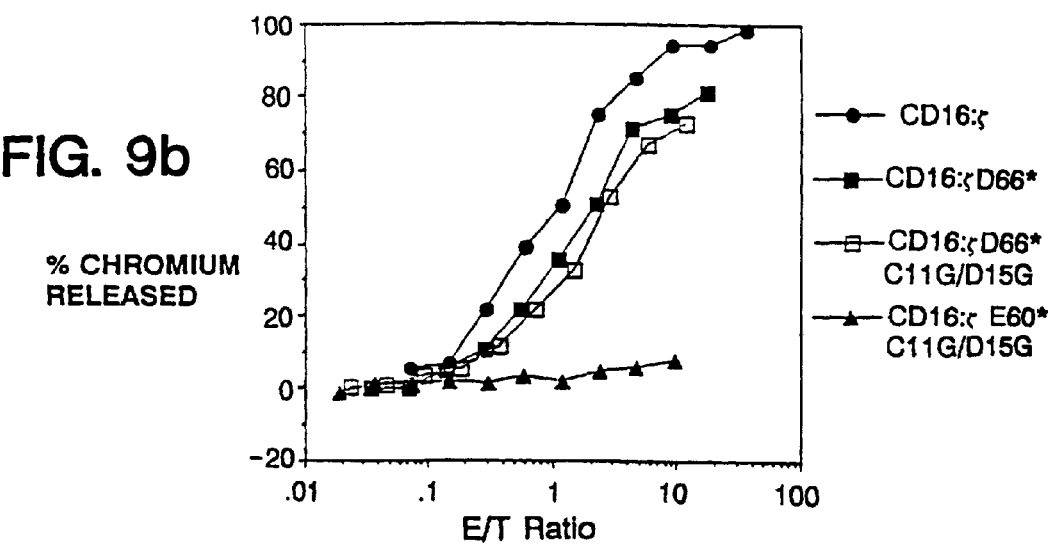
Figure 9C:
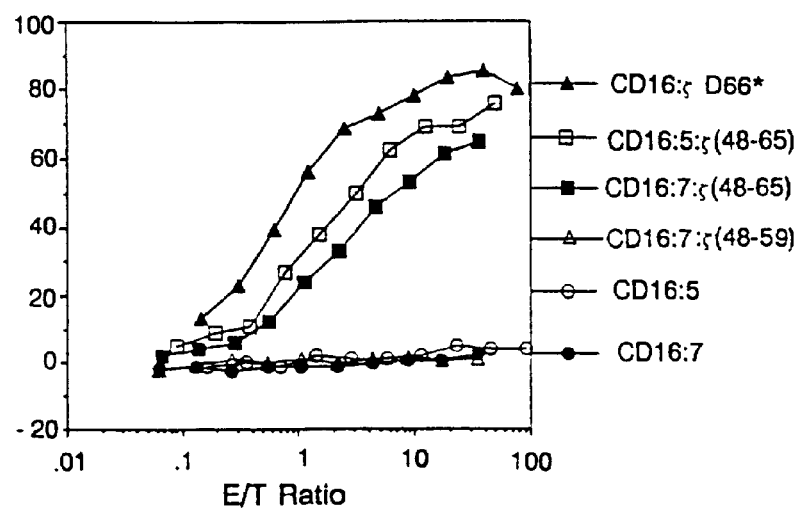
Figure 9D:
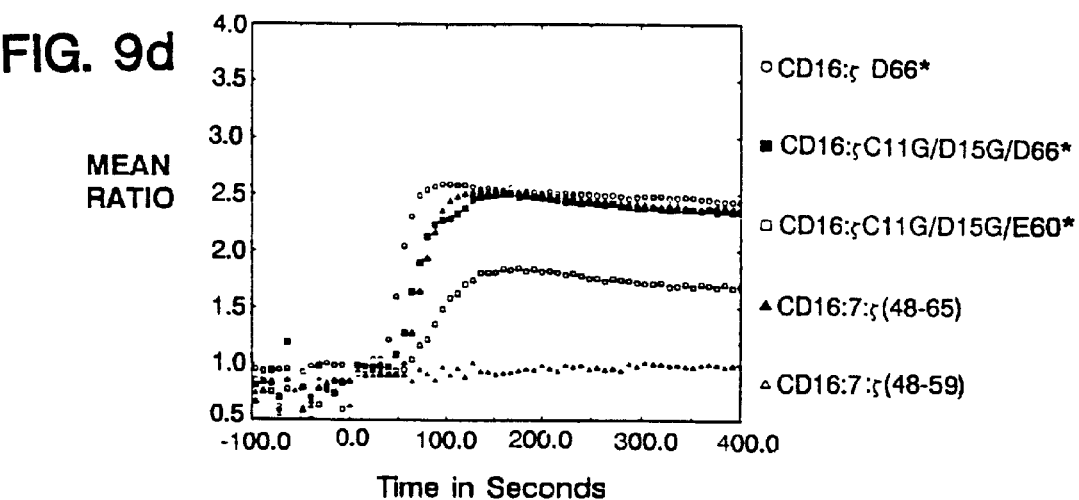
Figure 10A:
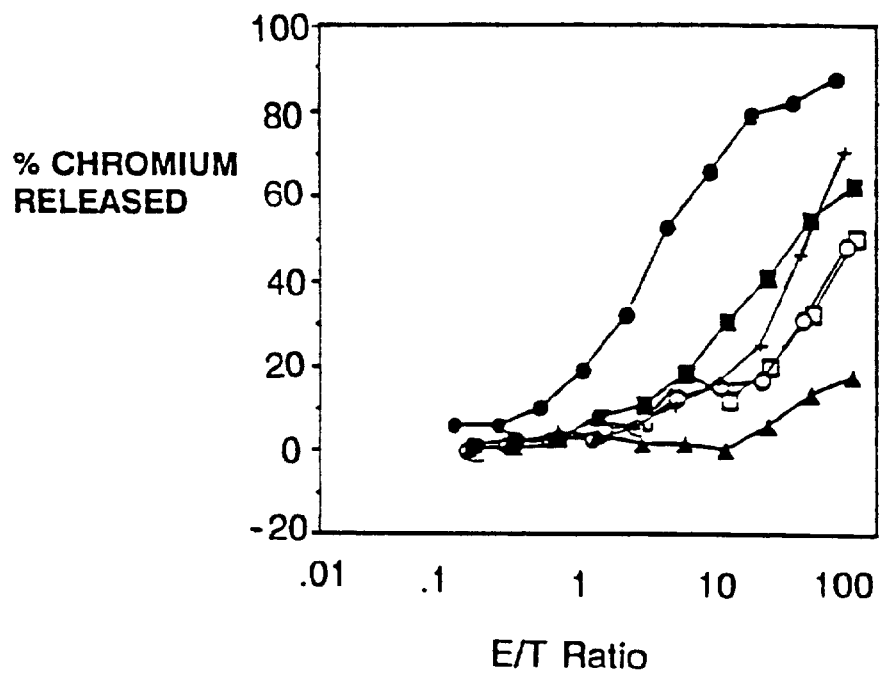
FIGS. 10A–F shows the contribution of individual amino acids to the activity of the 18 residue cytolytic signal-transducing motif.
Figure 10B:
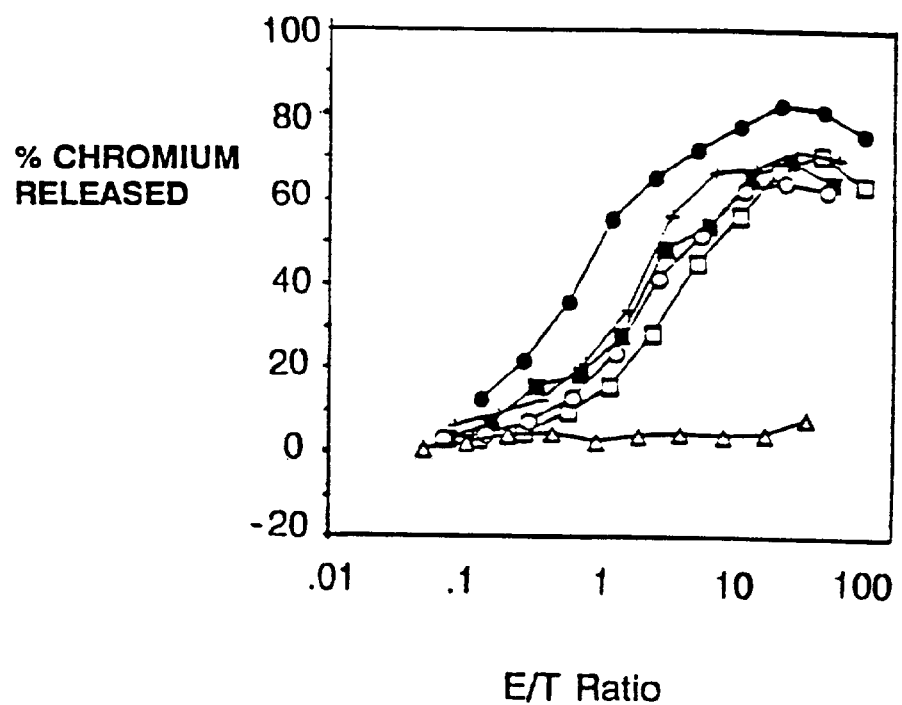
Figure 10C:
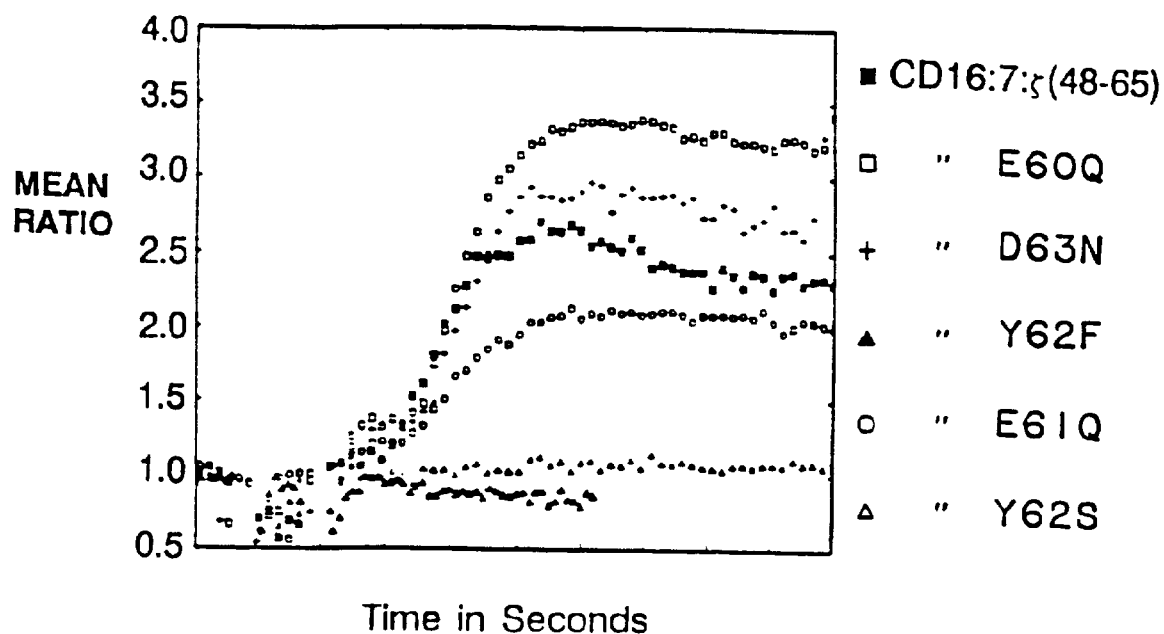
Figure 10D:
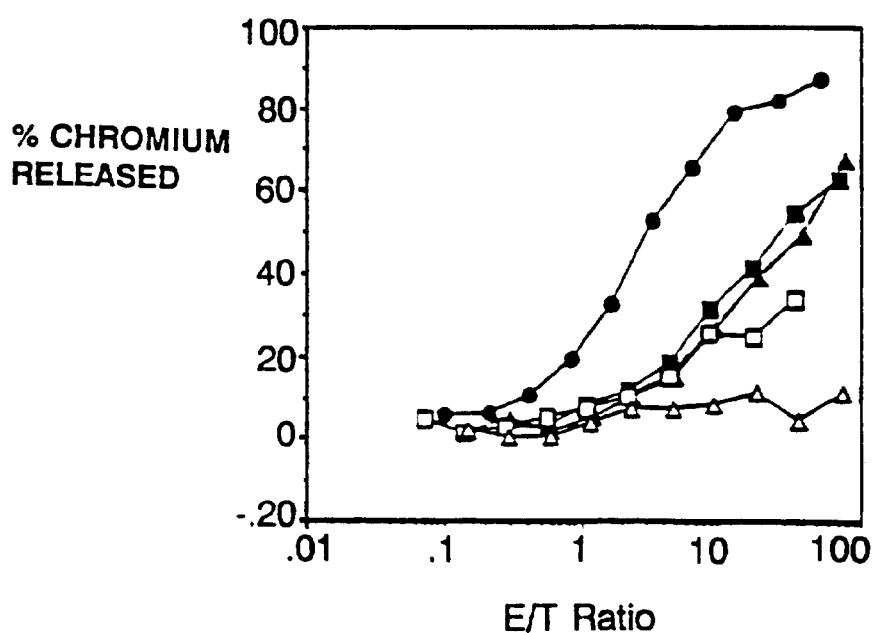
Figure 10E:
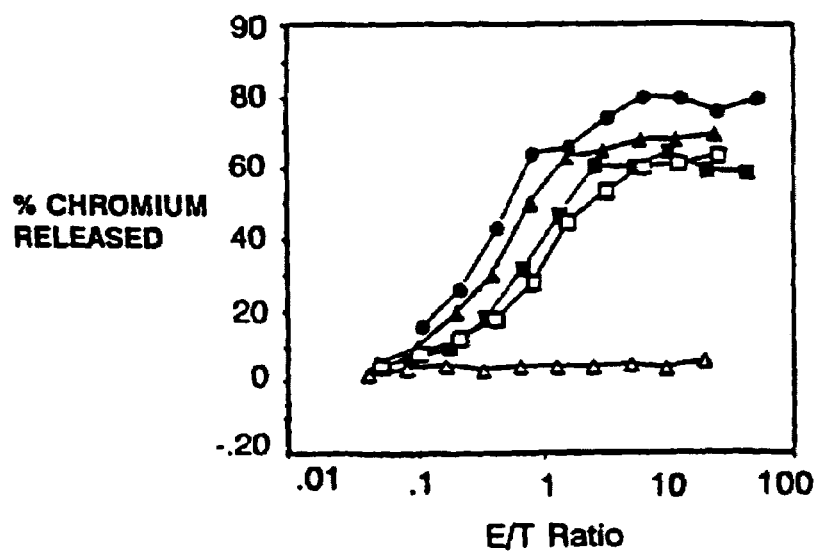
Figure 10F:
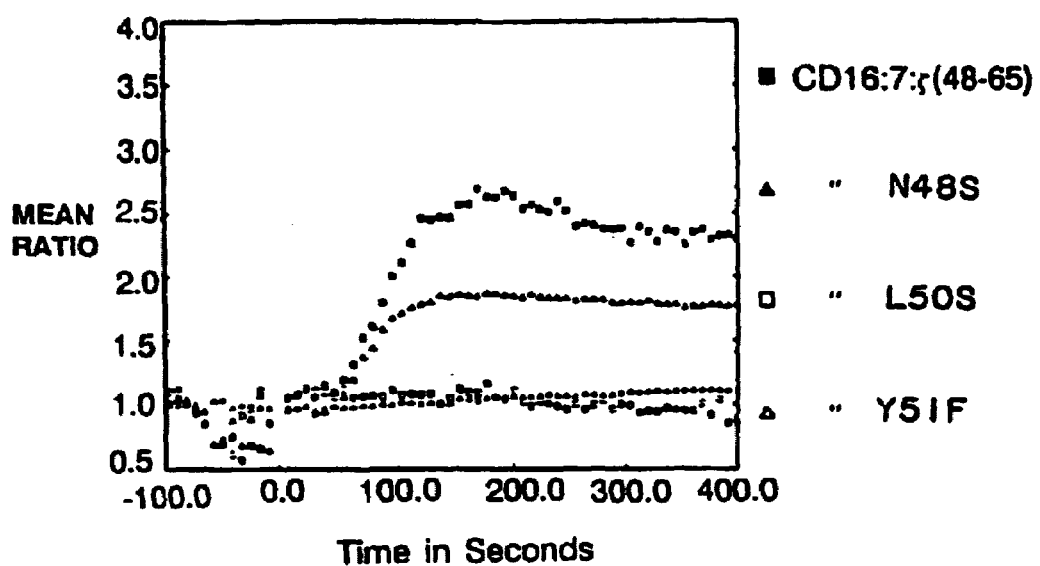

Flow cytometric studies showed that the deletion mutants lacking transmembrane Asp and Cys residues could still promote an increase in free intracellular calcium ion in response to antibody crosslinking in a TCR⁻ mutant Jurkat cell line (FIG. 9D). Similar results were obtained for chimeras expressed in the parental Jurkat line. In the case of CD16:ζCys11Gly/Asp15Gly/Glu60*, these data demonstrate that the ability to mediate calcium responsiveness can be mutationally separated from the ability to support cytolysis.

To definitively eliminate the possible contribution of ζ transmembrane residues, the transmembrane and first 17 cytoplasmic residues of ζ were replaced by sequences encoding the membrane spanning and first 14 or first 17 cytoplasmic residues of the CD5 or CD7 antigens, respectively (FIG. 9A). The resulting tripartite fusion proteins CD16:5:ζ(48–65) and CD16:7:ζ(48–65) did not form disulfide-linked dimers as do the simpler CD16:ζ chimeras, because they lacked the cysteine residue in the ζ transmembrane domain. Both tripartite chimeras were able to mobilize calcium in Jurkat and TCR negative cell lines (FIG. 9D) and to mount a cytolytic response in CTL (FIG. 9C and data not shown). However truncation of the ζ portion to residue 59 in chimera CD16:7:ζ(48–59) abrogates the ability of tripartite fusion to direct calcium responsiveness in TCR positive or negative Jurkat cells or cytolysis in mature CTL (FIGS. 9C and 9D and data not shown).

To examine the contributions of individual residues within the 18-residue motif, we prepared a number of mutant variants by site-directed mutagenesis, and evaluated their ability to mediate receptor-directed killing under conditions of low (FIGS. 10A and 10D) or high (FIGS. 10B and 10E) expression of chimeric receptor. FIGS. 10A–F shows that while a number of relatively conservative substitutions (i.e., replacing acidic residues with their cognate amides, or tyrosine with phenylalanine) which spanned residues 59 to 63 yielded moderate compromise of cytolytic efficacy, in general the variants retained the ability to mobilize calcium. However collectively these residues comprise an important submotif inasmuch as their deletion eliminates cytolytic activity. Conversion of Tyr 62 to either Phe or Ser eliminated both the cytotoxic and calcium responses. At the amino terminus of the 18 residue segment, replacement of Tyr 51 with Phe abolished both calcium mobilization and cytolytic activity, while substitution of Leu with Ser at position 50 eliminated the calcium response while only partially impairing cytolysis. Without being bound to a particular hypothesis, it is suspected that the inability of the Leu50Ser mutant to mobilize calcium in short term flow cytometric assays does not fully reflect its ability to mediate a substantial increase in free intracellular calcium ion over the longer time span of the cytolysis assay However, calcium-insensitive cytolytic activity has been reported for some cytolytic T cell lines, and the possibility that a similar phenomenon underlies the results described herein has not been ruled out. Replacement of Asn48 with Ser partially impaired cytotoxicity in some experiments while having little effect in others.

Figure 11A:
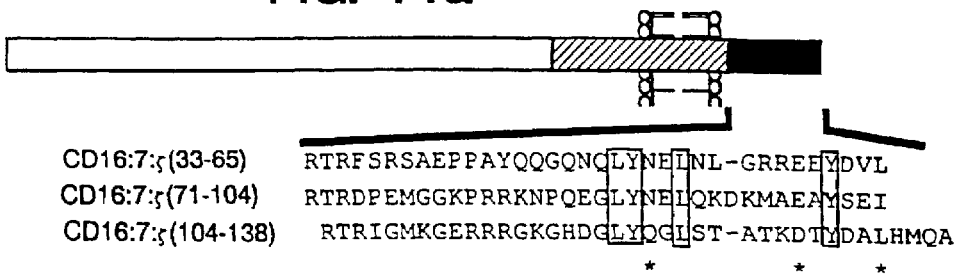
FIGS. 11A–B shows alignment of internal repeats of ζ and comparison of their ability to support cytolysis.
Figure 11B:
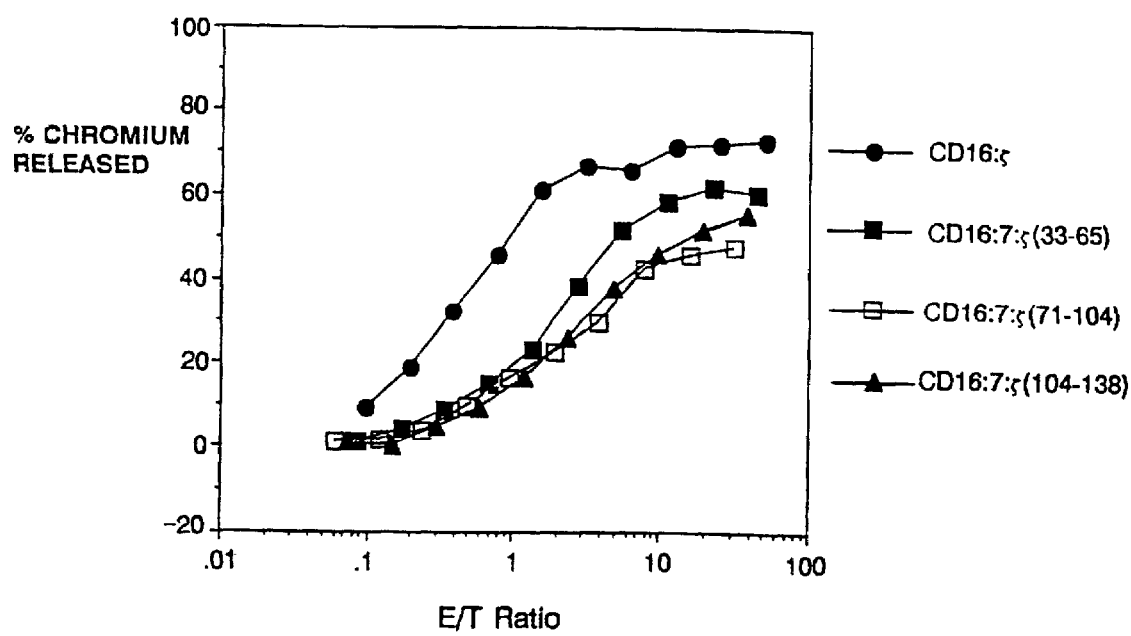

To investigate the potential role of redundant sequence elements, the intracellular domain of ζ was divided into three segments, spanning residues 33 to 65, 71 to 104, and 104 to 138. Each of these segments was attached to a CD16:CD7 chimera by means of a MluI site introduced just distal to the basic membrane anchoring sequences of the intracellular domain of CD7 (see below; FIG. 11A). Comparison of the cytolytic efficacy of the three elements showed they were essentially equipotent (FIG. 11B). Sequence comparison (FIG. 11A) shows that the second motif bears eleven residues between tyrosines, whereas the first and third motifs bear ten.

Although a precise accounting of the process of T cell activation has not been made, it is clear that aggregation of the antigen receptor, or of receptor chimeras which bear ζ intracellular sequences, triggers calcium mobilization, cytokine and granule release, and the appearance of cell surface markers of activation. The active site of ζ, a short linear peptide sequence probably too small to have inherent enzymatic activity, likely interacts with one or at most a few proteins to mediate cellular activation. It is also clear that mobilization of free calcium is not by itself sufficient for cellular activation, as the ability to mediate cytolysis can be mutationally separated from the ability to mediate calcium accumulation.

As shown herein, addition of 18 residues from the intracellular domain of ζ to the transmembrane and intracellular domain of two unrelated proteins allows the resulting chimeras to redirect cytolytic activity against target cells which bind to the extracellular portion of the fusion proteins. Although chimeras bearing the 18 residue motif are approximately eight-fold less active than chimeras based on full length ζ, the reduced activity can be attributed to the loss of transmembrane interactions which normally allow wild-type ζ to form disulfide linked dimers. That is, ζ deletion constructs which have the same carboxyl terminus as the motif and lack transmembrane Cys and Asp residues typically show slightly less activity than chimeras bearing only the 18 residue motif.

The cytolytic competency element on which we have focused has two tyrosines and no serines or threonines, restricting the possible contributions of phosphorylation to activity. Mutation of either tyrosine destroys activity, however, and although preliminary experiments do not point to a substantial tyrosine phosphorylation following crosslinking of chimeric surface antigens bearing the 18 reside motif, the possible participation of such phosphorylation at a low level cannot be excluded. In addition to the effects noted at the two tyrosine residues, a number of amino acid replacements at the amino and carboxyl terminus of the motif weaken activity under conditions of low receptor density.

Sequences similar to the ζ active motif can be found in the cytoplasmic domains of several other transmembrane proteins, including the CD3 δ and γ molecules, the surface IgM associated proteins mb1 and B29, and the β and γ chains of the high affinity IgE receptor, FcεRI (Reth, Nature 338:383, 1989). Although the function of these sequences is uncertain, if efficiently expressed, each may be capable of autonomous T cell activation, and such activity may explain the residual TCR responsiveness seen in a zeta-negative mutant cell line (Sussman et al., *Cell* 52:85, 1988).

ζ itself bears three such sequences, approximately equally spaced, and a rough trisection of the intracellular domain shows that each is capable of initiating a cytolytic response. η, a splice isoform of ζ (Jin et al., supra, 1990; Clayton et al., *Proc. Natl. Acad. Sci. USA* 88:5202, 1991), lacks the carboxyl half of the third motif. Because removal of the carboxyl half of the first motif abolishes activity, it appears likely that the majority of the biological effectiveness of η can be attributed to the first two motifs. Although by different measures η is equally as active as ζ in promoting antigen-mediated cytokine release (Bauer et al., *Proc. Natl. Acad. Sci. USA* 88:3842, 1991) or redirected cytolysis (see above), η is not phosphorylated in response to receptor stimulation (Bauer et al., supra, 1991). Thus either the presence of all three motifs is required for phosphorylation, or the third motif represents a favored substrate for an unidentified tyrosine kinase.

EXAMPLE IX

Cytolytic Signal Transduction by Human Fc Receptor

To evaluate the actions of different human Fc receptor subtypes, chimeric molecules were created in which the extracellular domain of the human CD4, CD5 or CD16 antigens were joined to the transmembrane and intracellular domains of the FcRIIγA, B1, B2, and ζ subtypes (nomenclature of Ravetch and Kinet, *Ann. Rev. Immunol.* 9:457, 1991). Specifically, cDNA sequences corresponding to the transmembrane and cytoplasmic domains of the previously described FcRIIA, B1, and B2 isoforms were amplified from the preexisting clone PC23 or from a human tonsil cDNA library (constructed by standard techniques) using the following synthetic oligonucleotides primers:

```
CCC GGA TCC CAG CAT GGG CAG CTC TT (SEQ ID NO: 18;
FcRII A forward);

CGC GGG GCG GCC GCT TTA GTT ATT ACT GTT GAC ATG GTC
GTT (SEQ ID NO: 19; FcRII A reverse);

GCG GGG GGA TCC CAC TGT CCA AGC TCC CAG CTC TTC ACC
G (SEQ ID NO: 20; FcRII B1 and FcRII B2 forward);
and GCG GGG GCG GCC GCC TAA ATA CGG TTC TGG TC (SEQ ID
NO: 21; FcRII B1 and FcRII B2 reverse).
```

These primers contained cleavage sites for the enzymes BamHI and NotI, respectively, indented 6 residues from the 5' end. The NotI site was immediately followed by an antisense stop codon, either CTA or TTA. All primers contained 18 or more residues complementary to the 5' and 3' ends of the desired fragments. The cDNA fragment corresponding to the FcRIIγC cytoplasmic domain, which differs from the IIA isoform in only one amino acid residue (L for P at residue 268) was generated by site directed mutagenesis by overlap PCR using primers of sequence:

```
TCA GAA AGA GAC AAC CTG AAG AAA CCA ACA A (SEQ ID
NO: 22) and

TTG TTG GTT TCT TCA GGT TGT GTC TTT CTG A (SEQ ID
NO: 23).
```

Figure 12:
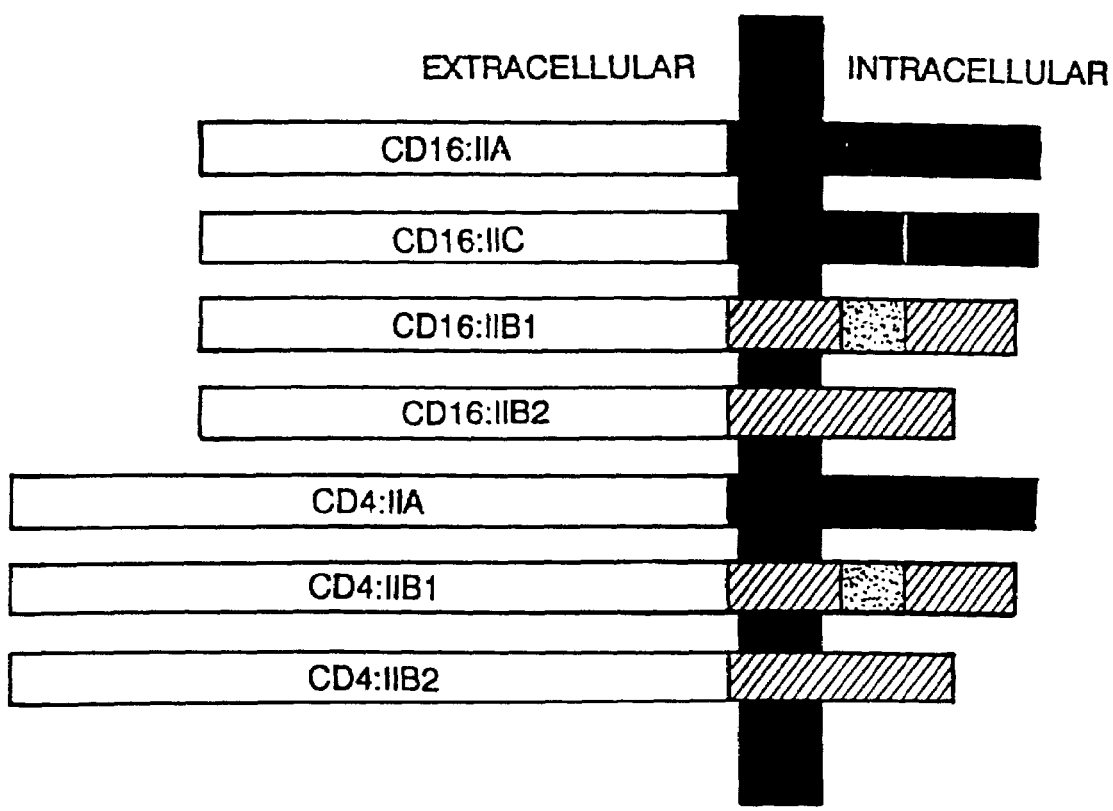
FIG. 12 is a schematic diagram of the CD16:FcRγII chimeras.

The PCR fragments were inserted into vaccinia virus expression vectors which contained the CD16 or CD4 extracellular domains respectively and subsequently inserted into wild type vaccinia by recombination at the thymidine kinase locus, using selection for cointegration of *E. coli* gpt to facilitate identification of the desired recombinants. The identities of all isoforms (shown in FIG. 12) were confirmed by dideoxy sequencing.

Production of the chimeric receptor proteins was further confirmed by immunoprecipitation studies. Approximately $10^7$ JRT3.T3.5 cells were infected for one hour in serum free IMDM medium with recombinant vaccinia at a multiplicity of infection of at least ten. Twelve hours post-infection, the cells were harvested and surface labeled with 0.5 mCi $^{125}$I per $10^7$ cells using the lactoperoxidase/glucose oxidase method (Clark and Einfeld, supra). The labeled cells were collected by centrifugation and lysed 1% NP-40, 0.1 mM $MgCl_2$, 5mM KCl, 0.2 M iodoacetamide and 1 mM PMSF. Nuclei were removed by centrifugation, and CD16 fusion proteins immunoprecipitated with antibody 4G8 and anti-mouse IgG agarose. Samples were electrophoresed under reducing conditions. All immunoprecipitated chimeric receptor molecules were of the expected molecular masses.

Figure 13A:
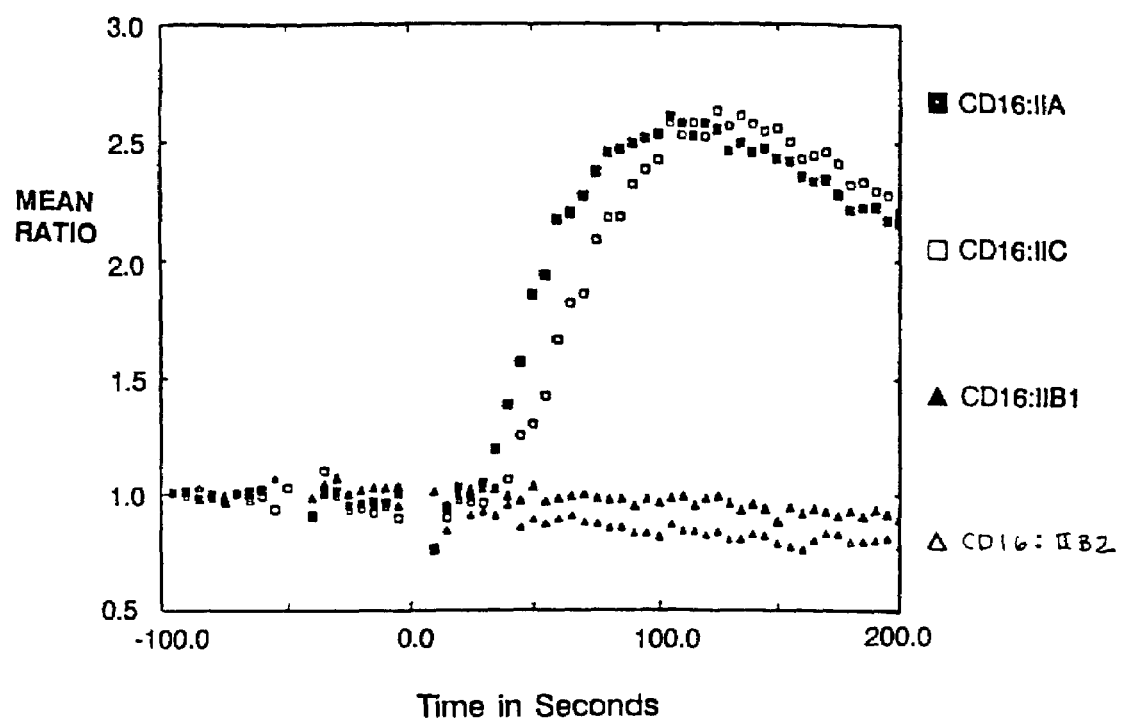
FIGS. 13A–B shows calcium mobilization following crosslinking of CD4:FcRγII and CD16:FcRγII chimeras.
Figure 13B:
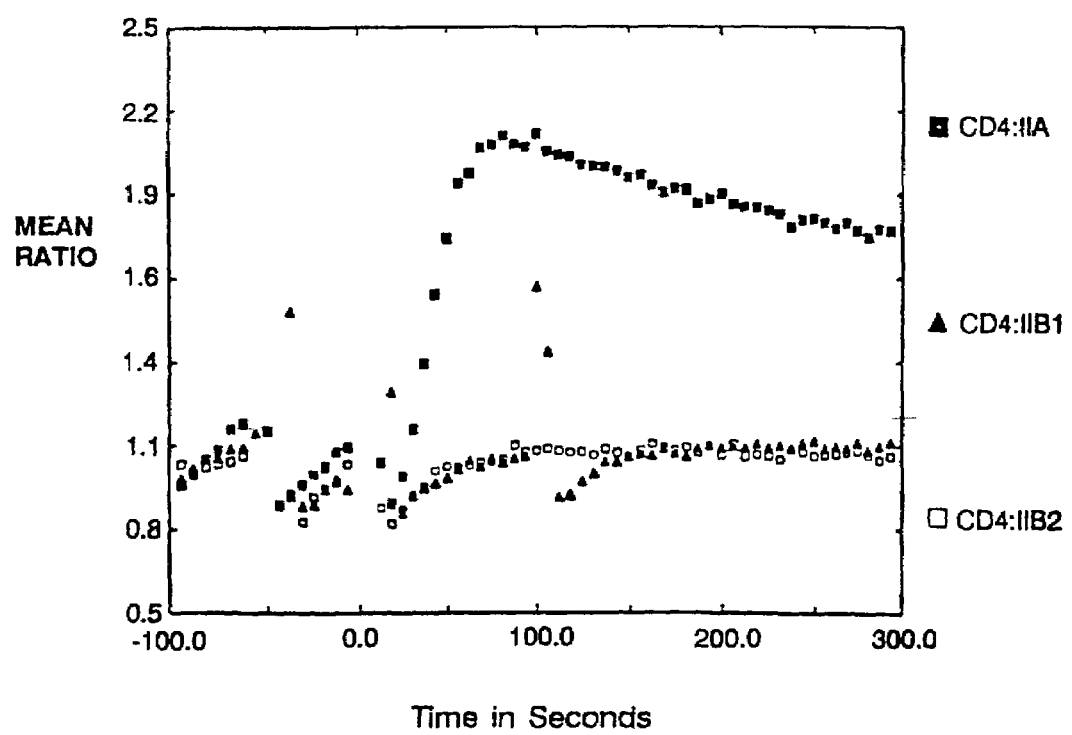

To test the ability of the chimeric receptors to mediate an increase in cytoplasmic free calcium ion, the recombinant viruses were used to infect the TCR⁻ mutant Jurkat cell line JRT3.T3.5 (as described herein) and cytoplasmic free calcium was measured in the cells (as described herein) following crosslinking of the receptor extracellular domains with monoclonal antibody 3G8 or Leu-3A (as described herein). These experiments revealed that the intracellular domains of FcRγII A and C were capable of mediating an increase in cytoplasmic free calcium ion after crosslinking of the extracellular domains, whereas the intracellular domains of FcRγII B1 and B2 were inactive under comparable conditions (FIGS. 13A and 13B). The CD4, CD5 and CD16 hybrids of FcRγII A shared essentially equal capacity to promote the calcium response (FIGS. 13A–B). Other cell lines, from both monocytic and lymphocytic lineages, were capable of responding to the signal initiated by crosslinking of the extracellular domains.

Figure 14A:
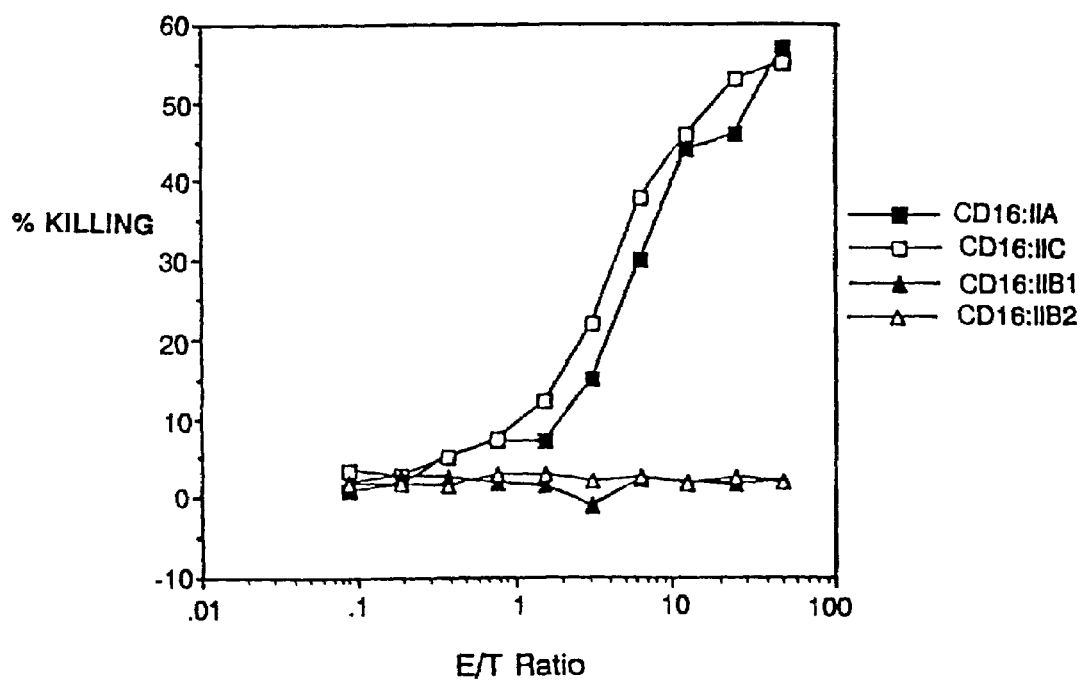
FIGS. 14A–B shows cytolysis assays of CD4:FcRγII and CD16:FcRγII chimeras.

To explore the involvement of the different FcRγII intracellular domains in cytolysis, human cytotoxic T lymphocytes (CTL) were infected with vaccinia recombinants expressing CD16:FcRγII A, B1, B2 and C chimeras. The infected cells were then cocultured with $^{51}$Cr-loaded hybridoma cells (i.e., 3G8 10-2 cells) which expressed cell surface antibody to CD16. In this assay CTLs bearing the CD16 chimera killed the hybridoma target cells (allowing release of free $^{51}$Cr) if the CD16 extracellular domain of the chimera has been joined to an intracellular segment capable of activating the lymphocyte effector program; this cytolysis assay is described in detail below. FIG. 14A shows that CTL armed with CD16:FcRγIIA and C, but not FcRγII B1 or B2, are capable of lysing target cells expressing cell surface anti-CD16 antibody.

Figure 14B:
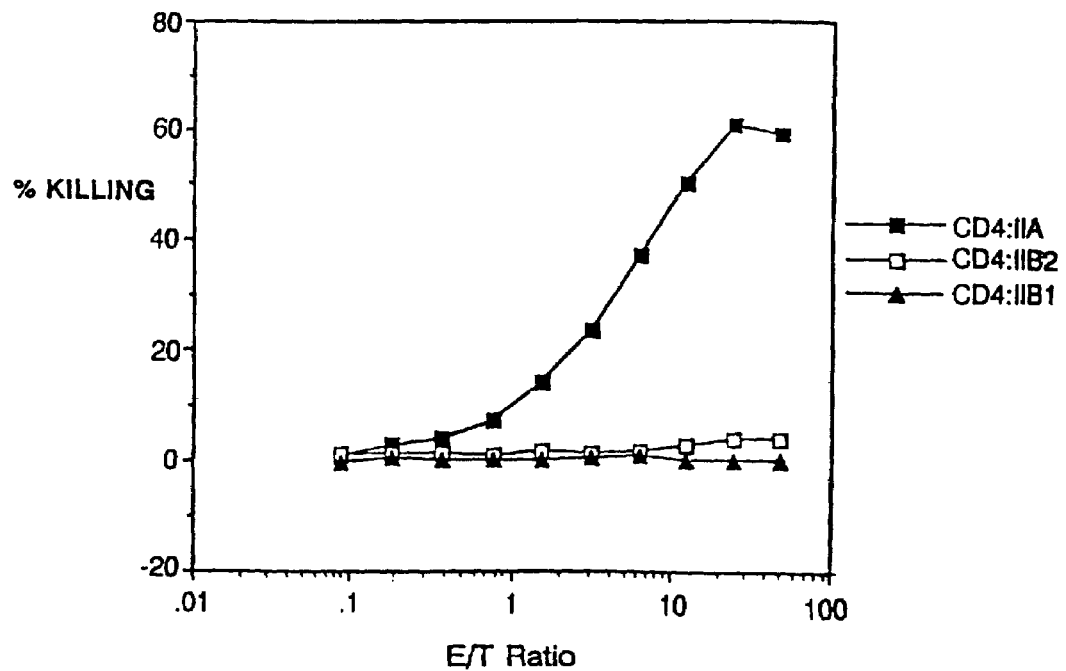

To eliminate the possibility that the specific cytolysis was in some way attributable to interaction with the CD16 moiety, cytolysis experiments were conducted in which the FcRII intracellular domains were attached to a CD4 extracellular domain. In this case the target cells were HeLa cells expressing HIV envelope gp120/41 proteins (specifically, HeLa cells infected with the vaccinia vector vPE16 (available from the National Institute of Allergy and Infections Disease AIDS Depository, Bethesda, Md.). As in the CD16 system, target cells expressing HIV envelope were susceptible to lysis by T cells expressing the CD4:FcRγII A chimera, but not FcRγII B1 or B2 (FIG. 14B).

Figure 15A:
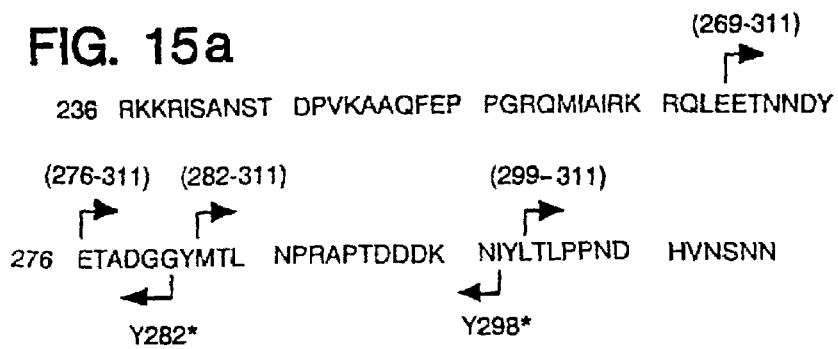
FIGS. 15A–E shows identification of residues in the FcRγII A tail which are important for cytolysis.

The intracellular domains of FcRγII A and C share no appreciable sequence homology with any other protein, including the members of the extended FcRγ/TCRζ family. To define the sequence elements responsible for induction of cytolysis, 5' and 3' deletions of the intracellular domain coding sequences (described below and shown in FIG. 15A) were prepared and were evaluated for efficacy in calcium mobilization and cytolysis assays (as described herein). In the experiments in which the amino terminal portion of the intracellular domain was removed, the transmembrane domain of FcRγII was replaced with the transmembrane domain of the unrelated CD7 antigen to eliminate the possible contribution of interactions mediated by the membrane-spanning domain.

Figure 15B:
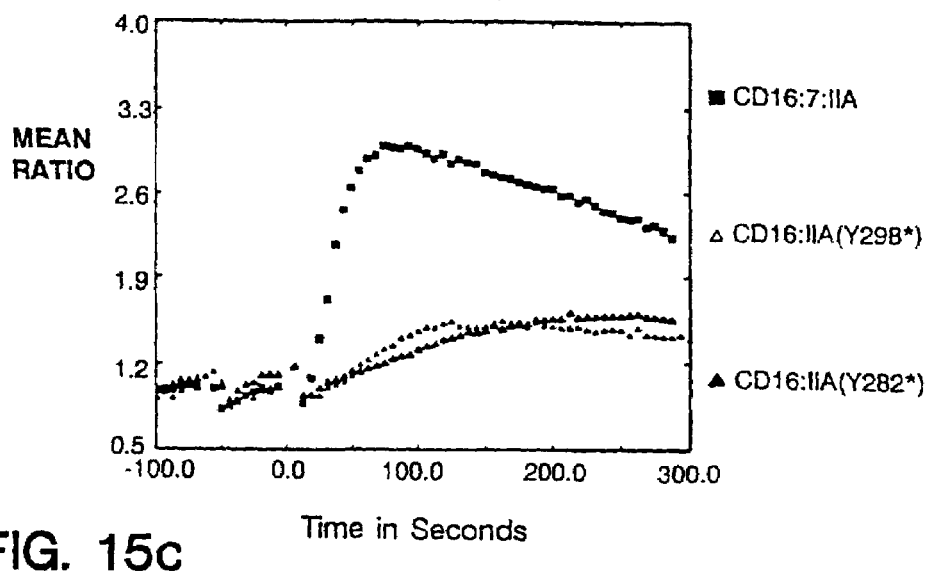
Figure 15C:
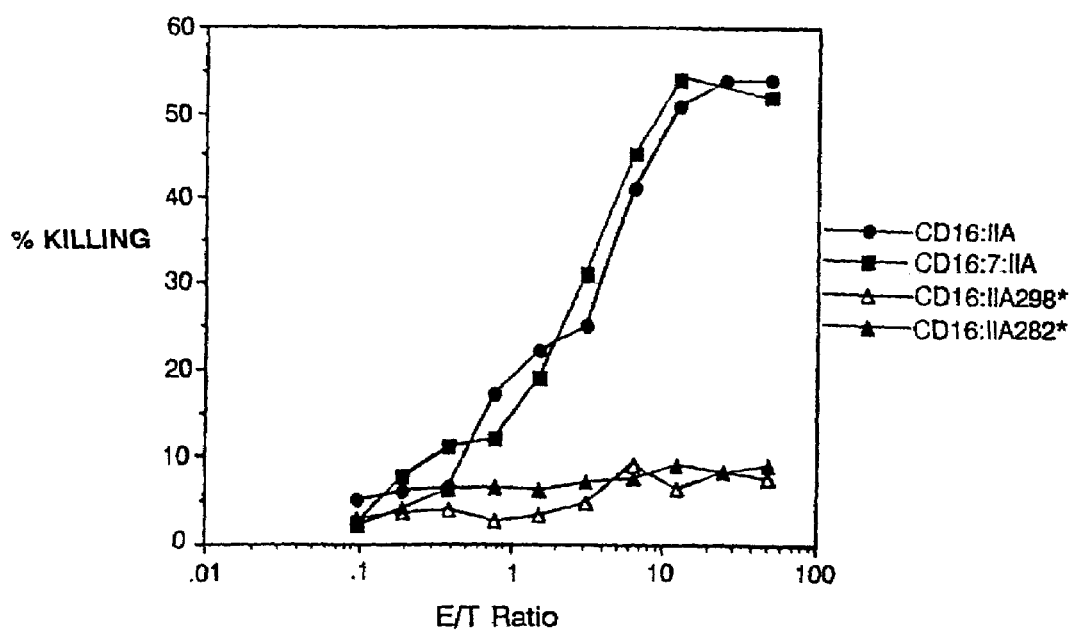
Figure 15D:
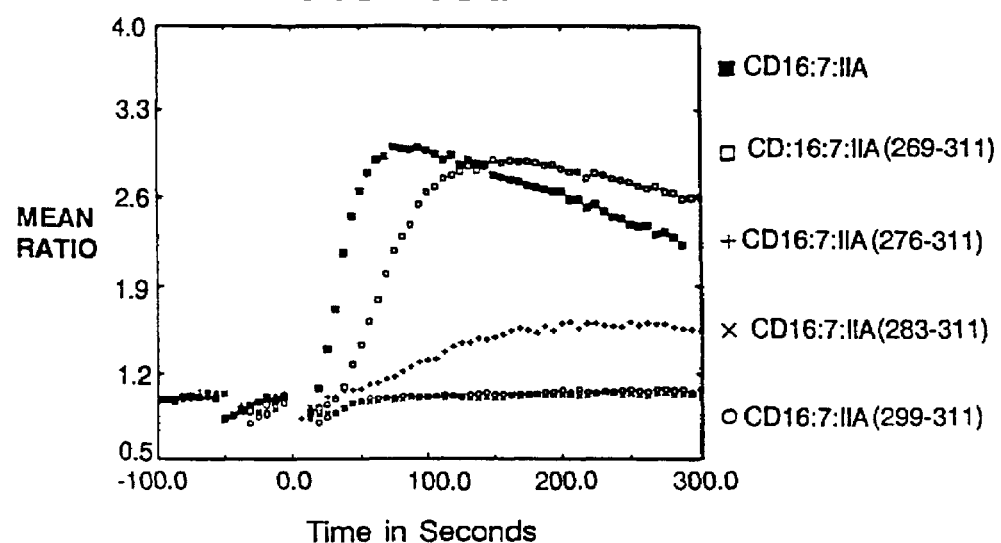
Figure 15E:
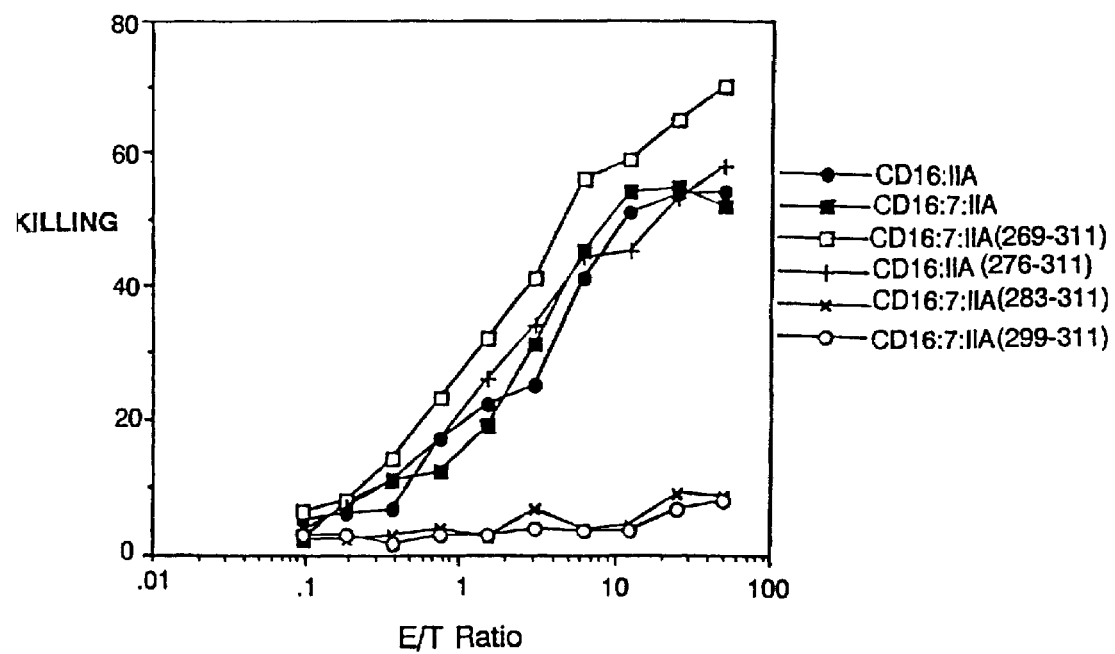

FIGS. 15B and 15C show that removal of the 14 carboxyl-terminal residues, including tyrosine 298, resulted in a complete loss of cytolytic capacity and a substantial reduction in calcium mobilization potential. Further deletion to just before tyrosine 282 gave an identical phenotype (FIGS. 15B and 15C). Deletion from the N-terminus of the intracellular domain to residue 268 had no substantial effect on either calcium profile or cytolytic potency, whereas deletion to residue 275 markedly impaired free calcium release but had little effect on cytolysis (FIGS. 15D and 15E). Further deletion, to residue 282, gave FcRγII tails which lacked the ability to either mobilize calcium or trigger cytolysis (FIGS. 15D and 15E). The 'active element' defined by these crude measures is relatively large (36 amino acids) and contains two tyrosines separated by 16 residues.

EXAMPLE X

Additional T Cell Receptor and B Cell Receptor Trigger Proteins

Other intracellular and transmembrane signal transducing domains according to the invention may be derived from the T cell receptor proteins, CD3 delta and T3 gamma, and the B cell receptor proteins, mb1 and B29. The amino acid sequences of these proteins are shown in FIG. 16 (CD3 delta; SEQ ID NO: 24), FIG. 17 (T3 gamma; SEQ ID NO: 25), FIG. 18 (mb1; SEQ ID NO: 26), and FIG. 19 (B29; SEQ ID NO: 27). The portions of the sequences sufficient for cytolytic signal transduction (and therefore preferably included in a chimeric receptor of the invention) are shown in brackets. Chimeric receptors which include these protein domains are constructed and used in the therapeutic methods of the invention generally as described above.

EXAMPLE XI

CD28 Chimeric Receptors

Because T cell activation has been shown to be augmented by engagement of CD28, the invention also includes therapeutic cells expressing pairs of chimeric receptors: the first chimera includes the intracellular domain of CD28, and the second chimera includes any intracellular or transmembrane signal-transducing domain described herein. In a given pair of chimeric receptors, the extracellular domains may be identical (for example, both may be derived from the CD4 protein and hence both recognize HIV or an HIV-infected cell), or each may be designed to recognize a different target molecule on the surface of a cell or pathogen.

In one particular example, a pair of chimeras may include two different extracellular domains, each recognizing a distinct antigen characteristic of a targeted tumor. Examples of tumor antigens include, without limitation, any of a number of carbohydrates (e.g., $Le^Y$, sialyl-$Le^Y$, $Le^x$, and sialyl-$Le^x$), carcinoembryonic antigen, CD40, modified CD44, α-fetoprotein, the T and Tn antigens, tenascin, and growth factor receptors (e.g., HER2/neu). By increasing the number of tumor surface markers that must be recognized to elicit a potent destructive response, this approach increases therapeutic specificity by decreasing the likelihood and frequency of destruction of non-cancerous cells.

This method of combinatorial control can be extended to any number of cooperating chimeric receptors and may be used to regulate any therapeutic method of the invention.

CD28 chimeras are constructed and expressed according to the methods described herein. The CD28 sequence is provided in Aruffo and Seed (*Proc. Natl. Acad. Sci. USA* 84:8573–8577 (1987)). Also included in this reference are descriptions of the CD28 intracellular and transmembrane domains. An example of a chimera bearing an intracellular CD28 domain is disclosed in Romeo et al. (*Cold Spring Harbor Symp. on Quant. Biol.* LVII:117–125 (1992)).

EXAMPLE XII

Experimental Methods

Vaccinia Infection and Radioimmunoprecipitation

Approximately $5 \times 10^6$ CV1 cells were infected for one hour in serum free DME medium with recombinant vaccinia at a multiplicity of infection (moi) of at least ten (titer measured on CV1 cells). The cells were placed in fresh medium after infection and labelled metabolically with 200 μCi/ml $^{35}$S-methionine plus cysteine (Tran$^{35}$S-label, ICN; Costo Mesa, Calif.) in methionine and cysteine free DMEM (Gibco; Grand Island, N.Y.) for six hours. The labelled cells were detached with PBS containing 1 mM EDTA, collected by centrifugation, and lysed in 1% NP-40, 0.1% SDS, 0.15 M NaCl, 0.05M Tris pH 8.0, 5mM EDTA, and 1 mM PMSF. Nuclei were removed by centrifugation, and CD4 proteins immunoprecipitated with OKT4 antibody and anti-mouse IgG agarose (Cappel, Durham, N.C.). Samples were electrophoresed through 8% polyacrylamide/SDS gels under non-reducing (NR) and reducing (R) conditions. Gels containing $^{35}$S-labelled samples were impregnated with En$^3$Hance (New England Nuclear, Boston, Mass.) prior to autoradiography. Facilitated expression of the transmembrane form of CD16, $CD16_{TM}$, was measured by comparing its expression in CV1 cells singly infected with $CD16_{TM}$ with expression in cells coinfected with viruses encoding $CD16_{TM}$ and ζ or γ chimeras. After infection and incubation for six hours or more, cells were detached from plates with PBS, 1 mM EDTA and the expression of $CD16_{TM}$ or the chimeras was measured by indirect immunofluorescence and flow cytometry.

Calcium Flux Assay

Jurkat subline E6 (Weiss et al., *J. Immunol.* 133:123–128 (1984)) cells were infected with recombinant vaccinia viruses for one hour in serum free IMDM at an moi of 10 and incubated for three to nine hours in IMDM, 10% FBS. Cells were collected by centrifugation and resuspended at $3 \times 10^6$ cells/ml in complete medium containing 1 mM Indo-1 acetomethoxyester (Grynkiewicz et al., *J. Biol. Chem.* 260: 3340–3450 (1985)) (Molecular Probes) and incubated at 37° C. for 45 minutes. The Indo-1 loaded cells were pelleted and resuspended at $1 \times 10^6$/ml in serum free IMDM and stored at room temperature in the dark. Cells were analyzed for free calcium ion by simultaneous measurement of the violet and blue fluorescence emission by flow cytometry (Rabinovitch et al., *J. Immunol.* 137:952–961 (1986)). To initiate calcium flux, either phycoerythrin (PE)-conjugated Leu-3A (anti-CD4) (Becton Dickinson, Lincoln Park, N.J.) at 1 µg/ml was added to the cell suspension followed by 10 µg/ml of unconjugated goat anti-mouse IgG at time 0 or unconjugated 3G8 (anti-CD16) monoclonal antibody was added to the cell suspension at 1 µg/ml followed by 10 µg/ml of PE-conjugated Fab$_2$' goat anti-monse IgG at time 0. Histograms of the violet/blue emission ratio were collected from the PE positive (infected) cell population, which typically represented 40–80% of all cells. The T cell antigen receptor response in uninfected cells was triggered by antibody OKT3, without crosslinking. For experiments involving CD16 chimeric receptors, samples showing baseline drift toward lower intracellular calcium (without antibody) were excluded from the analysis. Histogram data were subsequently analyzed by conversion of the binary data to ASCII using Write Hand Man (Cooper City, Fla.) software, followed by analysis with a collection of FORTRAN programs. The violet/blue emission ratio prior to the addition of the second antibody reagents was used to establish the normalized initial ratio, set equal to unity, and the resting threshold ratio, set so that 10% of the resting population would exceed threshold.

Cytolysis Assay

Human T cell line WH3, a CD8$^+$ CD4$^-$ HLA B44 restricted cytolytic line was maintained in IMDM, 10% human serum with 100 U/ml of IL-2 and was periodically stimulated either nonspecifically with irradiated (3000 rad) HLA-unmatched peripheral blood lymphocytes and 1 µg/ml of phytohemagglutinin, or specifically, with irradiated B44-bearing mononuclear cells. After one day of nonspecific stimulation, the PHA was diluted to 0.5 µg/ml by addition of fresh medium, and after three days the medium was changed. Cells were grown for at least 10 days following stimulation before use in cytotoxicity assays. The cells were infected with recombinant vaccinia at a multiplicity of infection of at least 10 for one hour in serum free medium, followed by incubation in complete medium for three hours. Cells were harvested by centrifugation and resuspended at a density of 1×10$^7$ cells/ml. 100 µl were added to each well of a U-bottom microtiter plate containing 100 µl/well of complete medium. Cells were diluted in two-fold serial steps. Two wells for each sample did not contain lymphocytes, to allow spontaneous chromium release and total chromium uptake to be measured. The target cells, from HeLa subline S3, were infected in 6.0 or 10.0 cm plates at an approximate moi of 10 for one hour in serum free medium, followed by incubation in complete medium for three hours. They were then detached from the dishes with PBS, 1mM EDTA and counted. An aliquot of 10$^6$ target cells (HeLa, Raji, or RJ2.2.5 cells for the CD4 chimeric receptor experiments and 3G8 10-2 cells; Shen et al., *Mol. Immunol.* 26:959 (1989) for the CD16 chimeric receptor experiments) was centrifuged and resuspended in 50 µl of sterile $^{51}$Cr-sodium chromate (1 mCi/ml, Dupont Wilmington, Del.) for one hour at 37° C. with intermittent mixing, then washed three times with PBS. 100 µl of labelled cells resuspended in medium at 105 cells/ml were added to each well. Raji and RJ2.2.5 target cells were labelled in the same manner as HeLa cells. The microtiter plate was spun at 750×g for 1 minute and incubated for 4 hours at 37° C. At the end of the incubation period, the cells in each well were resuspended by gentle pipetting, a sample removed to determine the total counts incorporated, and the microtiter plate spun at 750×g for 1 minute. 100 µl aliquots of supernatant were removed and counted in a gamma ray scintillation counter. The percent killing was corrected for the fraction of infected target cells (usually 50–90%) measured by flow cytometry. For infected effector cells the effector:target ratio was corrected for the percent of cells infected (usually 20–50% for the CD4 chimeric receptor experiments and >70% for the CD16 chimeric receptor experiments).

In Vitro Mutagenesis of the ζ Sequence

To create point mutations in amino acid residues 11 and or 15 of the ζ sequence, synthetic oligonucleotide primers extending from the BamHI site upstream of the ζ transmembrane domain, and converting native ζ residue 11 from Cys to Gly (C11G) or residue 15 from Asp to Gly (D15G) or both (C11G/D15G) were prepared and used in PCR reactions to generate mutated fragments which were reinserted into the wild type CD4:ζ constructs.

To create ζ deletions, ζ cDNA sequences were amplified by PCR using synthetic oligonucleotide primers designed to create a stop codon (UAG) after residues 50, 59, or 65. The primers contained the cleavage site for the enzyme NotI indented five or six residues from the 5' end, usually in a sequence of the form CGC GGG CGG CCG CTA (SEQ ID NO: 11), where the last three residues correspond to the stop anticodon. The NotI and stop anticodon sequences were followed by 18 or more residues complementary to the desired 3' end of the fragment. The resulting chimeras were designated CD16:ζY51*, CD16:ζE60* and CD16:ζD66* respectively. The BamHI site upstream of the transmembrane domain and the NotI site were used to generate fragments that were reintroduced into the wild type CD16:ζ construct. Monomeric ζ chimeras were created by liberating the ζ transmembrane and membrane proximal intracellular sequences by BamHI and SacI digestion of the Asp$^-$ and Cys$^-$ CD4:ζ construct described above and inserting the fragment into the CD16:ζE60* and CD16:ζD66* construct respectively.

CD16:7:ζ(48–65) and CD16:7ζ(48–59) Tripartite Chimera Construction.

To prepare the construct CD16:ζD66*, the ζ cDNA sequence corresponding to the transmembrane domain and the 17 following residues of the cytoplasmic domain was replaced by corresponding transmembrane and cytoplasmic domain obtained from the CD5 and CD7 cDNA. The CD5 and CD7 fragments were generated by a PCR reaction using forward oligonucleotides including a BamHI restriction cleavage site and corresponding to the region just upstream of the transmembrane domain of CD5 and CD7 respectively and the following reverse oligonucleotides overlapping the CD5 and CD7 sequences respectively and the ζ sequence which contained the SacI restriction cleavage site.

```
CD5:ζ: CGC GGG CTC GTT ATA GAG CTG GTT CTG GCG CTG
CTT CTT CTG (SEQ ID NO: 12)

CD7:ζ: CGC GGG GAG CTC GTT ATA GAG CTG GTT TGC CGC
CGA ATT CTT ATC CCG (SEQ ID NO: 13).
```

The CD5 and CD7 PCR products were digested with BamHI and SacI and ligated to BamHI and SacI digested CD16:ζE60* and replacing the ζ sequence from BamHI to SacI by the CD7 fragment. To make the constructs CD16:CD5 and CD16:CD7, CD5 and CD7 fragments were obtained by PCR using an oligonucleotide containing a NotI restriction cleavage site and encoding a stop codon (UAA) after the residue Gln416 and Ala193 of CD5 and CD7 respectively. The CD5 and CD7 PCR fragment were digested with BamHI and NotI and inserted in the CD16:ζAsp66* construct.

In Vitro Mutagenesis of the N-terminal Residues within the ζ Cytolytic Signal-Transducing Motif Synthetic oligonucleotide primers extending from the SacI site inside the ζ motif and converting native residue 48 from Asn to Ser (N48S), residue 50 from Leu to Ser (L50S) and residue 51 from Tyr to Phe (Y51F) were synthesized and used in a PCR reaction to generate fragments that were reintroduced into the wild type CD16:7:ζ(48–65) construct.

In Vitro Mutagenesis of C-terminal Residues within the ζ Cytolytic Signal-Transducing Motif Synthetic oligonucleotide primers extending from the NotI site 3' to the stop codon and converting native residue 60 from Glu to Gln (E60Q), residue 61 from Glu to Gln (E61Q), residue 62 from Tyr to Phe or Ser (Y62F or Y62S) and residue 63 from Asp to Asn (D63N) were synthesized and used in PCR to generate fragments that were subcloned into the wild type CD16:ζD66* construct from the BamHI site to the NotI site.

CD16:7:ζ(33–65), CD16:7:ζ(71–104), CD16:7:ζ(104–137) Chimera Constructions

A CD7 transmembrane fragment bearing MluI and NotI sites at the junction between the transmembrane and intracellular domains was obtained by PCR using an oligonucleotide with the following sequence: CGC GGG GCG GCC ACG CGT CCT CGC CAG CAC ACA (SEQ ID NO:14). The resulting PCR fragment was digested with BamHI and NotI and reinserted into the CD16:7:ζ(48–65) construct. ζ fragments encoding residues 33 to 65, 71 to 104, and 104 to 137 were obtained by PCR reaction using pairs of primers containing MluI sites at the 5' end of the forward primers and stop codons followed by NotI sites at the 5' end of the reverse primers. In each case the restriction sites were indented six residues from the 5' terminus of the primer to insure restriction enzyme cleavage.

ζ 33: CGC GGG ACG CGT TTC AGC CGT CCT CGC CAG CAC ACA (SEQ ID NO: 15);

ζ 71: CGC GGG ACG CGT GAC CCT GAG ATG GGG GGA AAG (SEQ ID NO: 16); and

ζ 104: CGC GGG ACG CGT ATT GGG ATG AAA GGC GAG CGC (SEQ ID NO: 17).

Construction of FcRγIIA Deletion Mutants

Carboxyl terminal FcRIIA deletion mutants were constructed by PCR in the same fashion as for the full length constructs, converting the sequences encoding tyrosine at positions 282 and 298 into stop codons (TAA). The N-terminal deletions were generated by amplifying fragments encoding successively less of the intracellular domain by PCR, using oligonucleotides which allowed the resulting fragments to be inserted between MluI and NotI restriction sites into a previously constructed expression plasmid encoding the CD16 extracellular domain fused to the CD7 transmembrane domain, the latter terminating in a MluI site and the junction between the transmembrane and the intracellular domain.

OTHER EMBODIMENTS

The examples described above demonstrate that aggregation of ζ, η, or γ chimeras suffices to initiate the cytolytic effector cell response in T cells. The known range of expression of ζ, η, and γ, which includes T lymphocytes, natural killer cells, basophilic granulocytes, macrophages, and mast cells, suggests that conserved sequence motifs may interact with a sensory apparatus common to cells of hematopoietic origin and that an important component of host defense in the immune system may be mediated by receptor aggregation events.

The potency of the cytolytic response and the absence of a response to target cells bearing MHC class II receptors demonstrates that chimeras based on ζ, η, or γ form the basis for a genetic intervention for AIDS through adoptive immunotherapy. The broad distribution of endogenous ζ and γ and evidence that Fc receptors associated with γ mediate cytotoxicity in different cells types (Fanger et al., Immunol. Today 10:92–99 (1989)) allows a variety of cells to be considered for this purpose. For example, neutrophilic granulocytes, which have a very short lifespan (≈4 h) in circulation and are intensely cytolytic, are attractive target cells for expression of the chimeras. Infection of neutrophils with HIV is not likely to result in virus release, and the abundance of these cells (the most prevalent of the leukocytes) should facilitate host defense. Another attractive possibility for host cells are mature T cells, a population presently accessible to retroviral engineering (Rosenberg, Sci. Am. 262:62–69 (1990)). With the aid of recombinant IL-2, T cell populations can be expanded in culture with relative ease, and the expanded populations typically have a limited lifespan when reinfused (Rosenberg et al., N. Enql. J. Med. 323:570–578 (1990)).

Under the appropriate conditions, HIV recognition by cells expressing CD4 chimeras should also provide mitogenic stimuli, allowing the possibility that the armed cell population could respond dynamically to the viral burden. Although we have focused here on the behavior of the fusion proteins in cytolytic T lymphocytes, expression of the chimeras in helper lymphocytes might provide an HIV-mobilized source of cytokines which could counteract the collapse of the helper cell subset in AIDS. Recent description of several schemes for engineering resistance to infection at steps other than virus penetration (Friedman et al., Nature 335:452–454 (1988); Green et al., Cell 58:215–223 (1989); Malim et al., Cell 58:205–214 (1989); Trono et al., Cell 59:113–120 (1989); Buonocore et al., Nature 345:625–628 (1990)) suggests that cells bearing CD4 chimeras could be designed to thwart virus production by expression of appropriate agents having an intracellular site of action.

The ability to transmit signals to T lymphocytes through autonomous chimeras also provides the ability for the regulation of retrovirally engineered lymphocytes in vivo. Crosslinking stimuli, mediated for example by specific IgM antibodies engineered to remove complement-binding domains, may allow such lymphocytes to increase in number in situ, while treatment with similar specific IgG antibodies (for example recognizing an amino acid variation engineered into the chimeric chain) could selectively deplete the engineered population. Additionally, anti-CD4 IgM antibodies do not require additional crosslinking to mobilize calcium in Jurkat cells expressing CD4:ζ chimeras. The ability to regulate cell populations without recourse to repeated extracorporeal amplification may substantially extend the range and efficacy of current uses proposed for genetically engineered T cells.

To create other chimeras consisting of ζ, η or γ intracellular sequences, cDNA or genomic sequences encoding an extracellular domain of the receptor can be endowed with a restriction site introduced at a location just preceding the transmembrane domain of choice. The extracellular domain fragment terminating in the restriction site can then be joined to ζ, η, or γ sequences. Typical extracellular domains may be derived from receptors which recognize complement, carbohydrates, viral proteins, bacteria, protozoan or metazoan parasites, or proteins induced by them. Similarly, ligands or receptors expressed by pathogens or tumor cells can be attached to ζ, η, or γ sequences, to direct immune responses against cells bearing receptors recognizing those ligands.

While the invention has been described in connection with specific embodiments thereof, it will be understood that it is capable of further modifications and this application is intended to cover variations, uses, or adaptations of the invention and including such departures from the present disclosure as come within the art to which the invention pertains and as may be applied to the essential features hereinbefore set forth as follows in the scope of the appended claims.

The invention claimed is:

1. A cell expressing a proteinaceous membrane-bound chimeric receptor, the first of said receptor comprising (a) an extracellular portion which is capable of specifically recognizing and binding a target cell or a target infective agent, (b) a transmembrane portion derived from a T cell receptor, a B cell receptor, or an Fc receptor protein which, in the absence of an intracellular signalling domain, is capable of signalling said cell to destroy a receptor-bound target cell or a receptor-bound target infective agent, and (c) an intracellular domain that does not signal said cell to destroy a receptor-bound target cell or receptor-bound target infective agent; and the second of said receptors comprising (a) an extracellular portion which is capable of specifically recoginizing and binding said target cell or said target infective agent, and (b) an intracellular portion which is derived for CD28.

2. The cell of claim 1, wherein, following binding of said extracellular portion to said cell or agent, said transmembrane portion oligomerizes with a cytolytic signal-transducing protein of said receptor-bearing cell resulting in destruction of said receptor-bound agent or cell.

3. The cell of claim 1, wherein said binding is MHC-independent.

4. The cell of claims 1, wherein said transmembrane portion comprises an oligomerizing portion of a T cell receptor protein, a B cell receptor protein, or an Fc receptor protein, or a functional derivative thereof.

5. The cell of claim 1, wherein said extracellular portion comprises the ligand-binding portion of a receptor, the receptor-binding portion of a ligand, the antigen-binding portion of an antibody, or a functional derivative thereof.

6. The cell of claim 1, wherein said target infective agent is an immunodeficiency virus or said target cell is a host cell infected with an immunodeficiency virus.

7. The cell of claim 6, wherein said extracellular portion comprises an HIV envelope-binding portion of CD4, or a functional derivative thereof.

8. The cell of claim 6, wherein said HIV-envelope binding portion of CD4 comprises the peptide encoded by nucleotides 1–369 of SEQ ID NO:1.

9. A cell which expresses at least two proteinaceous membrane-bound chimeric receptors, the first of said receptors comprising (a) an extracellular portion which is capable of specifically recognizing and binding a target cell or a target infective agent, and (b) a transmembrane portion derived from a T cell receptor CD3, zeta, or eta polypeptide, a B cell receptor, or an Fc receptor, and (c) an intracellular domain that does not signal target cell or target infective agent destruction; and the second of said receptors comprising (a) an extracellular portion which is capable of specifically recognizing and binding said target cell or said target infective agent, and (b) an intracellular portion which is derived from CD28.

10. The cell of claim 1, wherein said cell destroys said receptor-bound target cell or target infective agent by cytolysis.

11. The cell of claim 1, wherein said transmembrane portion of the first of said receptors is derived from a T cell receptor protein.

12. The cell of claim 11, wherein said T cell receptor protein is ζ.

13. The cell of claim 12, wherein said chimeric receptor comprises amino acids 400–420 of SEQ ID NO:6.

* * * * *

UNITED STATES PATENT AND TRADEMARK OFFICE
CERTIFICATE OF CORRECTION

PATENT NO. : 7,049,136 B2 Page 1 of 1
APPLICATION NO. : 09/243008
DATED : May 23, 2006
INVENTOR(S) : Brian Seed, Charles Romeo and Waldemar Kolanus It is certified that error appears in the above-identified patent and that said Letters Patent is hereby corrected as shown below:

Column 14,
Line 26, replace "moleucles" with --molecules--; and
Line 32, replace "anti-placelet" with --anti-platelet--.

Column 21, Line 56, replace "CD16$^{TM}$" with --CD16$_{TM}$--.

Column 31, Line 8, replace "anti-monse" with --anti-mouse--.

Column 33, Line 54, replace "Mull" with --MluI--.

Column 68, Line 67, replace "for CD28." with --from CD28.--.

Column 69, Line 8, replace "claims" with --claim--.

Signed and Sealed this

Twenty-first Day of November, 2006

JON W. DUDAS
*Director of the United States Patent and Trademark Office*

SEQUENCE LISTING (1) GENERAL INFORMATION:

(iii) NUMBER OF SEQUENCES: 40

(2) INFORMATION FOR SEQ ID NO: 1:

(i) SEQUENCE CHARACTERISTICS:
      (A) LENGTH: 1728 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO: 1:

```
ATGAACCGGG GAGTCCCTTT TAGGCACTTG CTTCTGGTGC TGCAACTGGC            50

GCTCCTCCCA GCAGCCACTC AGGGAAACAA AGTGGTGCTG GGCAAAAAAG           100

GGGATACAGT GGAACTGACC TGTACAGCTT CCCAGAAGAA GAGCATACAA           150

TTCCACTGGA AAAACTCCAA CCAGATAAAG ATTCTGGGAA ATCAGGGCTC           200

CTTCTTAACT AAAGGTCCAT CCAAGCTGAA TGATCGCGCT GACTCAAGAA           250

GAAGCCTTTG GGACCAAGGA AACTTCCCCC TGATCATCAA GAATCTTAAG           300

ATAGAAGACT CAGATACTTA CATCTGTGAA GTGGAGGACC AGAAGGAGGA           350

GGTGCAATTG CTAGTGTTCG GATTGACTGC CAACTCTGAC ACCCACCTGC           400

TTCAGGGGCA GAGCCTGACC CTGACCTTGG AGAGCCCCCC TGGTAGTAGC           450

CCCTCAGTGC AATGTAGGAG TCCAAGGGGT AAAAACATAC AGGGGGGGAA           500

GACCCTCTCC GTGTCTCAGC TGGAGCTCCA GGATAGTGGC ACCTGGACAT           550

GCACTGTCTT GCAGAACCAG AAGAAGGTGG AGTTCAAAAT AGACATCGTG           600

GTGCTAGCTT TCCAGAAGGC CTCCAGCATA GTCTATAAGA AAGAGGGGGA           650

ACAGGTGGAG TTCTCCTTCC CACTCGCCTT TACAGTTGAA AAGCTGACGG           700

GCAGTGGCGA GCTGTGGTGG CAGGCGGAGA GGGCTTCCTC CTCCAAGTCT           750

TGGATCACCT TTGACCTGAA GAACAAGGAA GTGTCTGTAA AACGGGTTAC           800

CCAGGACCCT AAGCTCCAGA TGGGCAAGAA GCTCCCGCTC CACCTCACCC           850

TGCCCCAGGC CTTGCCTCAG TATGCTGGCT CTGGAAACCT CACCCTGGCC           900

CTTGAAGCGA AAACAGGAAA GTTGCATCAG GAAGTGAACC TGGTGGTGAT           950

GAGAGCCACT CAGCTCCAGA AAAATTTGAC CTGTGAGGTG TGGGGACCCA          1000

CCTCCCCTAA GCTGATGCTG AGCTTGAAAC TGGAGAACAA GGAGGCAAAG          1050

GTCTCGAAGC GGGAGAAGCC GGTGTGGGTG CTGAACCCTG AGGCGGGGAT          1100

GTGGCAGTGT CTGCTGAGTG ACTCGGGACA GGTCCTGCTG GAATCCAACA          1150

TCAAGGTTCT GCCCACATGG TCCACCCCGG TGCACGCGGA TCCCAAACTC          1200
```

```
TGCTACTTGC TAGATGGAAT CCTCTTCATC TACGGAGTCA TCATCACAGC         1250

CCTGTACCTG AGAGCAAAAT TCAGCAGGAG TGCAGAGACT GCTGCCAACC         1300

TGCAGGACCC CAACCAGCTC TACAATGAGC TCAATCTAGG GCGAAGAGAG         1350

GAATATGACG TCTTGGAGAA GAAGCGGGCT CGGGATCCAG AGATGGGAGG         1400

CAAACAGCAG AGGAGGAGGA ACCCCCAGGA AGGCGTATAC AATGCACTGC         1450

AGAAAGACAA GATGCCAGAA GCCTACAGTG AGATCGGCAC AAAAGGCGAG         1500

AGGCGGAGAG GCAAGGGGCA CGATGGCCTT TACCAGGACA GCCACTTCCA         1550

AGCAGTGCAG TTCGGGAACA GAAGAGAGAG AGAAGGTTCA GAACTCACAA         1600

GGACCCTTGG GTTAAGAGCC CGCCCCAAAG GTGAAAGCAC CCAGCAGAGT         1650

AGCCAATCCT GTGCCAGCGT CTTCAGCATC CCCACTCTGT GGAGTCCATG         1700

GCCACCCAGT AGCAGCTCCC AGCTCTAA                                 1728
```

(2) INFORMATION FOR SEQ ID NO: 2:

(i) SEQUENCE CHARACTERISTICS:
        (A) LENGTH: 1389 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 2:

```
ATGAACCGGG GAGTCCCTTT TAGGCACTTG CTTCTGGTGC TGCAACTGGC          50

GCTCCTCCCA GCAGCCACTC AGGGAAACAA AGTGGTGCTG GGCAAAAAAG         100

GGGATACAGT GGAACTGACC TGTACAGCTT CCCAGAAGAA GAGCATACAA         150

TTCCACTGGA AAAACTCCAA CCAGATAAAG ATTCTGGGAA ATCAGGGCTC         200

CTTCTTAACT AAAGGTCCAT CCAAGCTGAA TGATCGCGCT GACTCAAGAA         250

GAAGCCTTTG GGACCAAGGA AACTTCCCCC TGATCATCAA GAATCTTAAG         300

ATAGAAGACT CAGATACTTA CATCTGTGAA GTGGAGGACC AGAAGGAGGA         350

GGTGCAATTG CTAGTGTTCG GATTGACTGC CAACTCTGAC ACCCACCTGC         400

TTCAGGGGCA GAGCCTGACC CTGACCTTGG AGAGCCCCCC TGGTAGTAGC         450

CCCTCAGTGC AATGTAGGAG TCCAAGGGGT AAAAACATAC AGGGGGGGAA         500

GACCCTCTCC GTGTCTCAGC TGGAGCTCCA GGATAGTGGC ACCTGGACAT         550

GCACTGTCTT GCAGAACCAG AAGAAGGTGG AGTTCAAAAT AGACATCGTG         600

GTGCTAGCTT TCCAGAAGGC CTCCAGCATA GTCTATAAGA AGAGGGGA          650

ACAGGTGGAG TTCTCCTTCC CACTCGCCTT TACAGTTGAA AAGCTGACGG         700

GCAGTGGCGA GCTGTGGTGG CAGGCGGAGA GGGCTTCCTC CTCCAAGTCT         750

TGGATCACCT TTGACCTGAA GAACAAGGAA GTGTCTGTAA AACGGGTTAC         800

CCAGGACCCT AAGCTCCAGA TGGGCAAGAA GCTCCCGCTC CACCTCACCC         850

TGCCCCAGGC CTTGCCTCAG TATGCTGGCT CTGGAAACCT CACCCTGGCC         900

CTTGAAGCGA AAACAGGAAA GTTGCATCAG GAAGTGAACC TGGTGGTGAT         950

GAGAGCCACT CAGCTCCAGA AAAATTTGAC CTGTGAGGTG TGGGACCCA         1000

CCTCCCCTAA GCTGATGCTG AGCTTGAAAC TGGAGAACAA GGAGGCAAAG        1050

GTCTCGAAGC GGGAGAAGCC GGTGTGGGTG CTGAACCCTG AGGCGGGGAT        1100
```

-continued

| | |
|---|---|
| GTGGCAGTGT CTGCTGAGTG ACTCGGGACA GGTCCTGCTG GAATCCAACA | 1150 |
| TCAAGGTTCT GCCCACATGG TCCACCCCGG TGCACGCGGA TCCGCAGCTC | 1200 |
| TGCTATATCC TGGATGCCAT CCTGTTTTTG TATGGTATTG TCCTTACCCT | 1250 |
| GCTCTACTGT CGACTCAAGA TCCAGGTCCG AAAGGCAGAC ATAGCCAGCC | 1300 |
| GTGAGAAATC AGATGCTGTC TACACGGGCC TGAACACCCG GAACCAGGAG | 1350 |
| ACATATGAGA CTCTGAAACA TGAGAAACCA CCCCAATAG | 1389 |

(2) INFORMATION FOR SEQ ID NO: 3:

(i) SEQUENCE CHARACTERISTICS:
        (A) LENGTH: 1599 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

| | |
|---|---|
| ATGAACCGGG GAGTCCCTTT TAGGCACTTG CTTCTGGTGC TGCAACTGGC | 50 |
| GCTCCTCCCA GCAGCCACTC AGGGAAACAA AGTGGTGCTG GCAAAAAAG | 100 |
| GGGATACAGT GGAACTGACC TGTACAGCTT CCCAGAAGAA GAGCATACAA | 150 |
| TTCCACTGGA AAAACTCCAA CCAGATAAAG ATTCTGGGAA ATCAGGGCTC | 200 |
| CTTCTTAACT AAAGGTCCAT CCAAGCTGAA TGATCGCGCT GACTCAAGAA | 250 |
| GAAGCCTTTG GGACCAAGGA AACTTCCCCC TGATCATCAA GAATCTTAAG | 300 |
| ATAGAAGACT CAGATACTTA CATCTGTGAA GTGGAGGACC AGAAGGAGGA | 350 |
| GGTGCAATTG CTAGTGTTCG GATTGACTGC CAACTCTGAC ACCCACCTGC | 400 |
| TTCAGGGGCA GAGCCTGACC CTGACCTTGG AGAGCCCCCC TGGTAGTAGC | 450 |
| CCCTCAGTGC AATGTAGGAG TCCAAGGGGT AAAAACATAC AGGGGGGGAA | 500 |
| GACCCTCTCC GTGTCTCAGC TGGAGCTCCA GGATAGTGGC ACCTGGACAT | 550 |
| GCACTGTCTT GCAGAACCAG AAGAAGGTGG AGTTCAAAAT AGACATCGTG | 600 |
| GTGCTAGCTT TCCAGAAGGC CTCCAGCATA GTCTATAAGA AAGAGGGGGA | 650 |
| ACAGGTGGAG TTCTCCTTCC CACTCGCCTT TACAGTTGAA AAGCTGACGG | 700 |
| GCAGTGGCGA GCTGTGGTGG CAGGCGGAGA GGGCTTCCTC CTCCAAGTCT | 750 |
| TGGATCACCT TTGACCTGAA GAACAAGGAA GTGTCTGTAA AACGGGTTAC | 800 |
| CCAGGACCCT AAGCTCCAGA TGGGCAAGAA GCTCCCGCTC CACCTCACCC | 850 |
| TGCCCCAGGC CTTGCCTCAG TATGCTGGCT CTGGAAACCT CACCCTGGCC | 900 |
| CTTGAAGCGA AAACAGGAAA GTTGCATCAG GAAGTGAACC TGGTGGTGAT | 950 |
| GAGAGCCACT CAGCTCCAGA AAAATTTGAC CTGTGAGGTG TGGGGACCCA | 1000 |
| CCTCCCCTAA GCTGATGCTG AGCTTGAAAC TGGAGAACAA GGAGGCAAAG | 1050 |
| GTCTCGAAGC GGGAGAAGCC GGTGTGGGTG CTGAACCCTG AGGCGGGGAT | 1100 |
| GTGGCAGTGT CTGCTGAGTG ACTCGGGACA GGTCCTGCTG GAATCCAACA | 1150 |
| TCAAGGTTCT GCCCACATGG TCCACCCCGG TGCACGCGGA TCCCAAACTC | 1200 |
| TGCTACCTGC TGGATGGAAT CCTCTTCATC TATGGTGTCA TTCTCACTGC | 1250 |
| CTTGTTCCTG AGAGTGAAGT TCAGCAGGAG CGCAGAGCCC CCCGCGTACC | 1300 |
| AGCAGGGCCA GAACCAGCTC TATAACGAGC TCAATCTAGG ACGAAGAGAG | 1350 |

-continued

```
GAGTACGATG TTTTGGACAA GAGACGTGGC CGGGACCCTG AGATGGGGGG        1400

AAAGCCGAGA AGGAAGAACC CTCAGGAAGG CCTGTACAAT GAACTGCAGA        1450

AAGATAAGAT GGCGGAGGCC TACAGTGAGA TTGGGATGAA AGGCGAGCGC        1500

CGGAGGGGCA AGGGGCACGA TGGCCTTTAC CAGGGTCTCA GTACAGCCAC        1550

CAAGGACACC TACGACGCCC TTCACATGCA GGCCCTGCCC CCTCGCTAA         1599
```

(2) INFORMATION FOR SEQ ID NO: 4:

(i) SEQUENCE CHARACTERISTICS:
        (A) LENGTH: 575 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Asn Arg Gly Val Pro Phe Arg His Leu Leu Leu Val Leu Gln Leu
 1               5                  10                  15

Ala Leu Leu Pro Ala Ala Thr Gln Gly Asn Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300
```

```
Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Pro Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val His Ala Asp Pro Lys Leu
385                 390                 395                 400

Cys Tyr Leu Leu Asp Gly Ile Leu Phe Ile Tyr Gly Val Ile Ile Thr
                405                 410                 415

Ala Leu Tyr Leu Arg Ala Lys Phe Ser Arg Ser Ala Glu Thr Ala Ala
            420                 425                 430

Asn Leu Gln Asp Pro Asn Gln Leu Tyr Asn Glu Leu Asn Leu Gly Arg
        435                 440                 445

Arg Glu Glu Tyr Asp Val Leu Glu Lys Lys Arg Ala Arg Asp Pro Glu
    450                 455                 460

Met Gly Gly Lys Gln Gln Arg Arg Arg Asn Pro Gln Glu Gly Val Tyr
465                 470                 475                 480

Asn Ala Leu Gln Lys Asp Lys Met Pro Glu Ala Tyr Ser Glu Ile Gly
                485                 490                 495

Thr Lys Gly Glu Arg Arg Arg Gly Lys Gly His Asp Gly Leu Tyr Gln
            500                 505                 510

Asp Ser His Phe Gln Ala Val Gln Phe Gly Asn Arg Arg Glu Arg Glu
        515                 520                 525

Gly Ser Glu Leu Thr Arg Thr Leu Gly Leu Arg Ala Arg Pro Lys Gly
    530                 535                 540

Glu Ser Thr Gln Gln Ser Ser Gln Ser Cys Ala Ser Val Phe Ser Ile
545                 550                 555                 560

Pro Thr Leu Trp Ser Pro Trp Pro Pro Ser Ser Ser Ser Gln Leu
                565                 570                 575

(2) INFORMATION FOR SEQ ID NO: 5:

(i) SEQUENCE CHARACTERISTICS:
        (A) LENGTH: 462 amino acids
        (B) TYPE: amino acid
        (D) TOPOLOGY: linear (ii) MOLECULE TYPE: protein (xi) SEQUENCE DESCRIPTION: SEQ ID NO: 5:

Met Asn Arg Gly Val Pro Phe Arg His Leu Leu Leu Val Leu Gln Leu
1               5                   10                  15

Ala Leu Leu Pro Ala Ala Thr Gln Gly Asn Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
65                  70                  75                  80
```

-continued

```
Asp Ser Arg Arg Ser Leu Trp Asp Gln Gly Asn Phe Pro Leu Ile Ile
                85                  90                  95
Lys Asn Leu Lys Ile Glu Asp Ser Asp Thr Tyr Ile Cys Glu Val Glu
            100                 105                 110
Asp Gln Lys Glu Val Gln Leu Leu Val Phe Gly Leu Thr Ala Asn
        115                 120                 125
Ser Asp Thr His Leu Leu Gln Gly Gln Ser Leu Thr Leu Thr Leu Glu
    130                 135                 140
Ser Pro Pro Gly Ser Ser Pro Ser Val Gln Cys Arg Ser Pro Arg Gly
145                 150                 155                 160
Lys Asn Ile Gln Gly Gly Lys Thr Leu Ser Val Ser Gln Leu Glu Leu
                165                 170                 175
Gln Asp Ser Gly Thr Trp Thr Cys Thr Val Leu Gln Asn Gln Lys Lys
            180                 185                 190
Val Glu Phe Lys Ile Asp Ile Val Leu Ala Phe Gln Lys Ala Ser
        195                 200                 205
Ser Ile Val Tyr Lys Lys Glu Gly Glu Gln Val Glu Phe Ser Phe Pro
    210                 215                 220
Leu Ala Phe Thr Val Glu Lys Leu Thr Gly Ser Gly Glu Leu Trp Trp
225                 230                 235                 240
Gln Ala Glu Arg Ala Ser Ser Ser Lys Ser Trp Ile Thr Phe Asp Leu
                245                 250                 255
Lys Asn Lys Glu Val Ser Val Lys Arg Val Thr Gln Asp Pro Lys Leu
            260                 265                 270
Gln Met Gly Lys Lys Leu Pro Leu His Leu Thr Leu Pro Gln Ala Leu
        275                 280                 285
Pro Gln Tyr Ala Gly Ser Gly Asn Leu Thr Leu Ala Leu Glu Ala Lys
    290                 295                 300
Thr Gly Lys Leu His Gln Glu Val Asn Leu Val Val Met Arg Ala Thr
305                 310                 315                 320
Gln Leu Gln Lys Asn Leu Thr Cys Glu Val Trp Gly Pro Thr Ser Pro
                325                 330                 335
Lys Leu Met Leu Ser Leu Lys Leu Glu Asn Lys Glu Ala Lys Val Ser
            340                 345                 350
Lys Arg Glu Lys Pro Val Trp Val Leu Asn Pro Glu Ala Gly Met Trp
        355                 360                 365
Gln Cys Leu Leu Ser Asp Ser Gly Gln Val Leu Leu Glu Ser Asn Ile
    370                 375                 380
Lys Val Leu Pro Thr Trp Ser Thr Pro Val His Ala Asp Pro Gln Leu
385                 390                 395                 400
Cys Tyr Ile Leu Asp Ala Ile Leu Phe Leu Tyr Gly Ile Val Leu Thr
                405                 410                 415
Leu Leu Tyr Cys Arg Leu Lys Ile Gln Val Arg Lys Ala Asp Ile Ala
            420                 425                 430
Ser Arg Glu Lys Ser Asp Ala Val Tyr Thr Gly Leu Asn Thr Arg Asn
        435                 440                 445
Gln Glu Thr Tyr Glu Thr Leu Lys His Glu Lys Pro Pro Gln
    450                 455                 460 462
```

(2) INFORMATION FOR SEQ ID NO: 6:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Asn Arg Gly Val Pro Phe Arg His Leu Leu Val Leu Gln Leu
 1               5                  10                  15

Ala Leu Leu Pro Ala Ala Thr Gln Gly Asn Lys Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
 65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
                115                 120                 125

Ser Asp Thr His Leu Leu Gln Gly Gln Ser Leu Thr Leu Thr Leu Glu
130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
                180                 185                 190

Val Glu Phe Lys Ile Asp Ile Val Val Leu Ala Phe Gln Lys Ala Ser
                195                 200                 205

Ser Ile Val Tyr Lys Lys Glu Gly Glu Gln Val Glu Phe Ser Phe Pro
                210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
                275                 280                 285

Pro Gln Tyr Ala Gly Ser Gly Asn Leu Thr Leu Ala Leu Glu Ala Lys
                290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
                340                 345                 350

Lys Arg Glu Lys Pro Val Trp Val Leu Asn Pro Glu Ala Gly Met Trp
                355                 360                 365

Gln Cys Leu Leu Ser Asp Ser Gly Gln Val Leu Leu Glu Ser Asn Ile
                370                 375                 380
```

```
Lys Val Leu Pro Thr Trp Ser Thr Pro Val His Ala Asp Pro Lys Leu
385                 390                 395                 400

Cys Tyr Leu Leu Asp Gly Ile Leu Phe Ile Tyr Gly Val Ile Leu Thr
                405                 410                 415

Ala Leu Phe Leu Arg Val Lys Phe Ser Arg Ser Ala Glu Pro Pro Ala
            420                 425                 430

Tyr Gln Gln Gly Gln Asn Gln Leu Tyr Asn Glu Leu Asn Leu Gly Arg
            435                 440                 445

Arg Glu Glu Tyr Asp Val Leu Asp Lys Arg Arg Gly Arg Asp Pro Glu
        450                 455                 460

Met Gly Gly Lys Pro Arg Arg Lys Asn Pro Gln Glu Gly Leu Tyr Asn
465                 470                 475                 480

Glu Leu Gln Lys Asp Lys Met Ala Glu Ala Tyr Ser Glu Ile Gly Met
                485                 490                 495

Lys Gly Glu Arg Arg Arg Gly Lys Gly His Asp Gly Leu Tyr Gln Gly
                500                 505                 510

Leu Ser Thr Ala Thr Lys Asp Thr Tyr Asp Ala Leu His Met Gln Ala
            515                 520                 525

Leu Pro Pro Arg
    530
```

(2) INFORMATION FOR SEQ ID NO: 7:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 7:

```
CGCGGGGTGA CCGTGCCCTC CAGCAGCTTG GGC                                   33
```

(2) INFORMATION FOR SEQ ID NO: 8:

(i) SEQUENCE CHARACTERISTICS:
        (A) LENGTH: 50 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 8:

```
CGCGGGATC CGTCGTCCAG AGCCCGTCCA GCTCCCCGTC CTGGGCCTCA                  50
```

(2) INFORMATION FOR SEQ ID NO: 9:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 9:

```
CGCGGGCGGC CGCGACGCCG GCCAAGACAG CAC                                   33
```

(2) INFORMATION FOR SEQ ID NO: 10:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 10:

CGCGTTGACG AGCAGCCAGT TGGGCAGCAG CAG     33

(2) INFORMATION FOR SEQ ID NO: 11:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 11:

CGCGGGCGGC CGCTA     15

(2) INFORMATION FOR SEQ ID NO: 12:

(i) SEQUENCE CHARACTERISTICS:
        (A) LENGTH: 42 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 12:

CGCGGGCTCG TTATAGAGCT GGTTCTGGCG CTGCTTCTTC TG     42

(2) INFORMATION FOR SEQ ID NO: 13:

(i) SEQUENCE CHARACTERISTICS:
        (A) LENGTH: 48 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 13:

CGCGGGGAGC TCGTTATAGA GCTGGTTTGC CGCCGAATTC TTATCCCG     48

(2) INFORMATION FOR SEQ ID NO: 14:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 14:

CGCGGGGCGG CCACGCGTCC TCGCCAGCAC ACA     33

(2) INFORMATION FOR SEQ ID NO: 15:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 15:

CGCGGGACGC GTTTCAGCCG TCCTCGCCAG CACACA                            36

(2) INFORMATION FOR SEQ ID NO: 16:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 16:

CGCGGGACGC GTGACCCTGA GATGGGGGA AAG                                33

(2) INFORMATION FOR SEQ ID NO: 17:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 17:

CGCGGGACGC GTATTGGGAT GAAAGGCGAG CGC                                33

(2) INFORMATION FOR SEQ ID NO: 18:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 18:

CCGGATCCC AGCATGGGCA GCTCTT                                          26

(2) INFORMATION FOR SEQ ID NO: 19:

(i) SEQUENCE CHARACTERISTICS:
        (A) LENGTH: 42 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 19:

GCGGGGCGG CCGCTTTAGT TATTACTGTT GACATGGTCG TT                      42

```
(2) INFORMATION FOR SEQ ID NO: 20:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 20:

CGGGGGGAT CCCACTGTCC AAGCTCCCAG CTCTTCACCG                           40

(2) INFORMATION FOR SEQ ID NO: 21:

(i) SEQUENCE CHARACTERISTICS:
        (A) LENGTH: 32 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 21:

CGGGGGCGG CCGCCTAAAT ACGGTTCTGG TC                                   32

(2) INFORMATION FOR SEQ ID NO: 22:

(i) SEQUENCE CHARACTERISTICS:
        (A) LENGTH: 31 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 22:

CAGAAAGAG ACAACCTGAA GAAACCAACA A                                    31

(2) INFORMATION FOR SEQ ID NO: 23:

(i) SEQUENCE CHARACTERISTICS:
        (A) LENGTH: 31 bases
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 23:

TGTTGGTTT CTTCAGGTTG TGTCTTTCTG A                                    31

(2) INFORMATION FOR SEQ ID NO: 24:

(i) SEQUENCE CHARACTERISTICS:
        (A) LENGTH: 171 amino acids
        (B) TYPE: amino acid
        (D) TOPOLOGY: linear (ii) MOLECULE TYPE: amino acid (xi) SEQUENCE DESCRIPTION: SEQ ID NO: 24:

Met Glu His Ser Thr Phe Leu Ser Gly Leu Val Leu Ala Thr Leu Leu
                 5                  10                  15

Ser Gln Val Ser Pro Phe Lys Ile Pro Ile Glu Glu Leu Glu Asp Arg
             20                  25                  30

Val Phe Val Asn Cys Asn Thr Ser Ile Thr Trp Val Glu Gly Thr Val
         35                  40                  45
```

```
Gly Thr Leu Leu Ser Asp Ile Thr Arg Leu Asp Leu Gly Lys Arg Ile
             50                  55                  60

Leu Asp Pro Arg Gly Ile Tyr Arg Cys Asn Gly Thr Asp Ile Tyr Lys
 65                  70                  75                  80

Asp Lys Glu Ser Thr Val Gln Val His Tyr Arg Met Cys Gln Ser Cys
                 85                  90                  95

Val Glu Leu Asp Pro Ala Thr Val Ala Gly Ile Ile Val Thr Asp Val
            100                 105                 110

Ala Ile Thr Leu Leu Ala Leu Gly Val Phe Cys Phe Ala Gly His
            115                 120                 125

Glu Thr Gly Arg Leu Ser Gly Ala Ala Asp Thr Gln Ala Leu Leu Arg
            130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

(2) INFORMATION FOR SEQ ID NO: 25:

(i) SEQUENCE CHARACTERISTICS:
        (A) LENGTH: 182 amino acids
        (B) TYPE: amino acid
        (D) TOPOLOGY: linear (ii) MOLECULE TYPE: amino acid (xi) SEQUENCE DESCRIPTION: SEQ ID NO: 25:

```
Met Glu Gln Gly Lys Gly Leu Ala Val Leu Ile Leu Ala Ile Ile Leu
                  5                  10                  15

Leu Gln Gly Thr Leu Ala Gln Ser Ile Lys Gly Asn His Leu Val Lys
             20                  25                  30

Val Tyr Asp Tyr Gln Glu Asp Gly Ser Val Leu Leu Thr Cys Asp Ala
             35                  40                  45

Glu Ala Lys Asn Ile Thr Trp Phe Lys Asp Gly Lys Met Ile Gly Phe
 50                  55                  60

Leu Thr Glu Asp Lys Lys Lys Trp Asn Leu Gly Ser Asn Ala Lys Asp
 65                  70                  75                  80

Pro Arg Gly Met Tyr Gln Cys Lys Gly Ser Gln Asn Lys Ser Lys Pro
                 85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
            115                 120                 125

Leu Ala Val Gly Val Tyr Phe Ile Ala Gly Gln Asp Gly Val Arg Gln
            130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180
```

(2) INFORMATION FOR SEQ ID NO: 26:

(i) SEQUENCE CHARACTERISTICS:
        (A) LENGTH: 220 amino acids
        (B) TYPE: amino acid
        (D) TOPOLOGY: linear (ii) MOLECULE TYPE: amino acids (xi) SEQUENCE DESCRIPTION: SEQ ID NO: 26:

```
Met Pro Gly Gly Leu Glu Ala Leu Arg Ala Leu Pro Leu Leu Leu Phe
                 5                  10                 15
Leu Ser Tyr Ala Cys Leu Gly Pro Gly Cys Gln Ala Leu Arg Val Glu
             20                  25                  30
Gly Gly Pro Pro Ser Leu Thr Val Asn Leu Gly Glu Glu Ala Arg Leu
             35                  40                  45
Thr Cys Glu Asn Asn Gly Arg Asn Pro Asn Ile Thr Trp Trp Phe Ser
     50                  55                  60
Leu Gln Ser Asn Ile Thr Trp Pro Pro Val Pro Leu Gly Pro Gly Gln
65                  70                  75                  80
Gly Thr Thr Gly Gln Leu Phe Phe Pro Glu Val Asn Lys Asn Thr Gly
                 85                  90                  95
Ala Cys Thr Gly Cys Gln Val Ile Glu Asn Asn Ile Leu Lys Arg Ser
                100                 105                 110
Cys Gly Thr Tyr Leu Arg Val Arg Asn Pro Val Pro Arg Pro Phe Leu
                115                 120                 125
Asp Met Gly Glu Gly Thr Lys Asn Arg Ile Ile Thr Ala Glu Gly Ile
    130                 135                 140
Ile Leu Leu Phe Cys Ala Val Val Pro Gly Thr Leu Leu Leu Phe Arg
145                 150                 155                 160
Lys Arg Trp Gln Asn Glu Lys Phe Gly Val Asp Met Pro Asp Asp Tyr
                165                 170                 175
Glu Asp Glu Asn Leu Tyr Glu Gly Leu Asn Leu Asp Asp Cys Ser Met
                180                 185                 190
Tyr Glu Asp Ile Ser Arg Gly Leu Gln Gly Thr Tyr Gln Asp Val Gly
                195                 200                 205
Asn Leu His Ile Gly Asp Ala Gln Leu Glu Lys Pro
                210                 215                 220
```

(2) INFORMATION FOR SEQ ID NO: 27:

(i) SEQUENCE CHARACTERISTICS:
    (A) LENGTH: 228 amino acids
    (B) TYPE: amino acid
    (D) TOPOLOGY: linear (ii) MOLECULE TYPE: amino acid (xi) SEQUENCE DESCRIPTION: SEQ ID NO: 27:

```
Met Ala Thr Leu Val Leu Ser Ser Met Pro Cys His Trp Leu Leu Phe
                 5                  10                 15
Leu Leu Leu Leu Phe Ser Gly Glu Pro Val Pro Ala Met Thr Ser Ser
             20                  25                  30
Asp Leu Pro Leu Asn Phe Gln Gly Ser Pro Cys Ser Gln Ile Trp Gln
         35                  40                  45
His Pro Arg Phe Ala Ala Lys Lys Arg Ser Ser Met Val Lys Phe His
     50                  55                  60
Cys Tyr Thr Asn His Ser Gly Ala Leu Thr Trp Phe Arg Lys Arg Gly
65                  70                  75                  80
Ser Gln Gln Pro Gln Glu Leu Val Ser Glu Glu Gly Arg Ile Val Gln
                 85                  90                  95
```

```
Thr Gln Asn Gly Ser Val Tyr Thr Leu Thr Ile Gln Asn Ile Gln Tyr
            100                 105                 110

Glu Asp Asn Gly Ile Tyr Phe Cys Lys Gln Lys Cys Asp Ser Ala Asn
            115                 120                 125

His Asn Val Thr Asp Ser Cys Gly Thr Glu Leu Leu Val Leu Gly Phe
            130                 135                 140

Ser Thr Leu Asp Gln Leu Lys Arg Arg Asn Thr Leu Lys Asp Gly Ile
145                 150                 155                 160

Ile Leu Ile Gln Thr Leu Leu Ile Ile Leu Phe Ile Ile Val Pro Ile
                165                 170                 175

Phe Leu Leu Leu Asp Lys Asp Asp Gly Lys Ala Gly Met Glu Glu Asp
            180                 185                 190

His Thr Tyr Glu Gly Leu Asn Ile Asp Gln Thr Ala Thr Tyr Glu Asp
            195                 200                 205

Ile Val Thr Leu Arg Thr Gly Glu Val Lys Trp Ser Val Gly Glu His
210                 215                 220

Pro Gly Gln Glu
225
```

(2) INFORMATION FOR SEQ ID NO: 28:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 28:

```
Gln Ser Phe Gly Leu Leu Asp Pro Lys Leu Cys Tyr Leu Leu Asp Gly
1               5                   10                  15
```

(2) INFORMATION FOR SEQ ID NO: 29:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 29:

```
Pro Thr Trp Ser Thr Pro Val His Ala Asp Pro Lys Leu Cys Tyr Leu
1               5                   10                  15

Leu Asp Gly
```

(2) INFORMATION FOR SEQ ID NO: 30:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 30:

```
Leu Gly Glu Pro Gln Leu Cys Tyr Ile Leu Asp Ala
1               5                   10
```

-continued (2) INFORMATION FOR SEQ ID NO: 31:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 31:

```
Pro Thr Trp Ser Thr Pro Val His Ala Asp Pro Gln Leu Cys Tyr Ile
1               5                   10                  15
Leu Asp Ala
```

(2) INFORMATION FOR SEQ ID NO: 32:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 32:

```
Gln Ser Phe Gly Leu Leu Asp Pro Lys Leu Cys Tyr Leu Leu Asp Gly
1               5                   10                  15
```

(2) INFORMATION FOR SEQ ID NO: 33:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 33:

```
Phe Ser Pro Pro Gly Ala Asp Pro Lys Leu Cys Tyr Leu Leu Asp Gly
1               5                   10                  15
```

(2) INFORMATION FOR SEQ ID NO: 34:

(i) SEQUENCE CHARACTERISTICS:
        (A) LENGTH: 142 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 34:

```
Gln Ser Phe Gly Leu Leu Asp Pro Lys Leu Cys Tyr Leu Leu Asp Gly
1               5                   10                  15
Ile Leu Phe Ile Tyr Gly Val Ile Leu Thr Ala Leu Phe Leu Arg Val
                20                  25                  30
Lys Phe Ser Arg Ser Ala Glu Pro Pro Ala Tyr Gln Gln Gly Gln Asn
                35                  40                  45
Gln Leu Tyr Asn Glu Leu Asn Leu Gly Arg Arg Glu Glu Tyr Asp Val
                50                  55                  60
Leu Asp Lys Arg Arg Gly Arg Asp Pro Glu Met Gly Gly Lys Pro Arg
65                  70                  75                  80
```

```
Arg Lys Asn Pro Gln Glu Gly Leu Tyr Asn Glu Leu Gln Lys Asp Lys
                85                  90                  95
Met Ala Glu Ala Tyr Ser Glu Ile Gly Met Lys Gly Glu Arg Arg Arg
            100                 105                 110
Gly Lys Gly His Asp Gly Leu Tyr Gln Gly Leu Ser Thr Ala Thr Lys
        115                 120                 125
Asp Thr Tyr Asp Ala Leu His Met Gln Ala Leu Pro Pro Arg
    130                 135                 140
```

(2) INFORMATION FOR SEQ ID NO: 35:

(i) SEQUENCE CHARACTERISTICS:
        (A) LENGTH: 35 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 35:

```
Arg Val Lys Phe Ser Arg Ser Ala Glu Pro Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu
        35
```

(2) INFORMATION FOR SEQ ID NO: 36:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 36:

```
Lys Lys Leu Val Lys Lys Phe Arg Gln Lys Lys Gln Arg Gln Asn Gln
1               5                   10                  15
Leu Tyr Asn Glu Leu Asn Leu Gly Arg Arg Glu Glu Tyr Asp Val Leu
            20                  25                  30
```

(2) INFORMATION FOR SEQ ID NO: 37:

(i) SEQUENCE CHARACTERISTICS:
        (A) LENGTH: 35 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 37:

```
Arg Thr Gln Ile Lys Lys Leu Cys Ser Trp Arg Asp Lys Asn Ser Ala
1               5                   10                  15
Ala Asn Gln Leu Tyr Asn Glu Leu Asn Leu Gly Arg Arg Glu Glu Tyr
            20                  25                  30
Asp Val Leu
        35
```

```
(2) INFORMATION FOR SEQ ID NO: 38:

(i) SEQUENCE CHARACTERISTICS:
        (A) LENGTH: 35 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 38:

Arg Thr Arg Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu
        35

(2) INFORMATION FOR SEQ ID NO: 39:

(i) SEQUENCE CHARACTERISTICS:
        (A) LENGTH: 36 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 39:

Arg Thr Arg Asp Pro Glu Met Gly Gly Lys Pro Arg Arg Lys Asn Pro
1               5                   10                  15

Gln Glu Gly Leu Tyr Asn Glu Leu Gln Lys Asp Lys Met Ala Glu Ala
                20                  25                  30

Tyr Ser Glu Ile
        35

(2) INFORMATION FOR SEQ ID NO: 40:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 40:

Arg Thr Arg Ile Gly Met Lys Gly Glu Arg Arg Arg Gly Lys Gly His
1               5                   10                  15

Asp Gly Leu Tyr Gln Gly Leu Ser Thr Ala Thr Lys Asp Thr Tyr Asp
                20                  25                  30

Ala Leu His Met Gln Ala
        35
```